(12) United States Patent
Kadoma et al.

(10) Patent No.: US 9,309,223 B2
(45) Date of Patent: Apr. 12, 2016

(54) HETEROCYCLIC COMPOUND, LIGHT-EMITTING ELEMENT, LIGHT-EMITTING DEVICE, ELECTRONIC DEVICE, AND LIGHTING DEVICE

(75) Inventors: Hiroshi Kadoma, Kanagawa (JP); Kaori Ogita, Kanagawa (JP); Satoko Shitagaki, Kanagawa (JP); Nobuharu Ohsawa, Tochigi (JP); Satoshi Seo, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 602 days.

(21) Appl. No.: 13/537,763

(22) Filed: Jun. 29, 2012

(65) Prior Publication Data

US 2013/0009543 A1    Jan. 10, 2013

(30) Foreign Application Priority Data

Jul. 8, 2011    (JP) ................. 2011-151717

(51) Int. Cl.
| | | |
|---|---|---|
| H01L 51/54 | (2006.01) | |
| C09K 11/06 | (2006.01) | |
| C07D 401/10 | (2006.01) | |
| C07D 405/10 | (2006.01) | |
| C07D 409/10 | (2006.01) | |
| H01L 51/00 | (2006.01) | |
| H05B 33/20 | (2006.01) | |
| H01L 51/50 | (2006.01) | |

(52) U.S. Cl.
CPC ............ *C07D 401/10* (2013.01); *C07D 405/10* (2013.01); *C07D 409/10* (2013.01); *C09K 11/06* (2013.01); *H01L 51/0072* (2013.01); *H05B 33/20* (2013.01); *C09K 2211/1029* (2013.01); *C09K 2211/1088* (2013.01); *C09K 2211/1092* (2013.01); *H01L 51/5012* (2013.01)

(58) Field of Classification Search
None
See application file for complete search history.

(56) References Cited

U.S. PATENT DOCUMENTS

| | | |
|---|---|---|
| 6,723,445 B2 | 4/2004 | Li et al. |
| 7,355,340 B2 | 4/2008 | Shitagaki et al. |
| 7,858,724 B2 | 12/2010 | Kanitz et al. |
| 8,007,927 B2 | 8/2011 | Lin et al. |
| 8,221,905 B2 | 7/2012 | Lin et al. |
| 8,367,850 B2 | 2/2013 | Ma et al. |
| 8,580,402 B2 | 11/2013 | Lin et al. |
| 8,586,204 B2 | 11/2013 | Xia et al. |
| 8,652,652 B2 | 2/2014 | Brooks et al. |
| 8,822,708 B2 | 9/2014 | Ma et al. |
| 8,866,377 B2 | 10/2014 | Adamovich et al. |
| 9,005,771 B2 | 4/2015 | Ma et al. |
| 9,123,903 B2 | 9/2015 | Lin et al. |
| 9,153,786 B2 | 10/2015 | Ma et al. |
| 2004/0067387 A1* | 4/2004 | Kim et al. ............... 428/690 |
| 2004/0076853 A1 | 4/2004 | Jarikov |
| 2008/0314965 A1 | 12/2008 | Roberts et al. |
| 2009/0072718 A1 | 3/2009 | Nomura et al. |
| 2009/0140641 A1 | 6/2009 | Nomura et al. |
| 2009/0140642 A1 | 6/2009 | Kadoma et al. |
| 2009/0153034 A1 | 6/2009 | Lin et al. |
| 2009/0153041 A1 | 6/2009 | Kawakami et al. |
| 2009/0184633 A1 | 7/2009 | Kadoma et al. |
| 2009/0203704 A1 | 8/2009 | Kadoma et al. |

(Continued)

FOREIGN PATENT DOCUMENTS

| | | |
|---|---|---|
| EP | 2511254 A | 10/2012 |
| EP | 2520571 A | 11/2012 |

(Continued)

OTHER PUBLICATIONS

Machine translation of JP2007-189001. Date of publication: Jul. 26, 2007.*

(Continued)

*Primary Examiner* — Andrew K Bohaty
(74) *Attorney, Agent, or Firm* — Fish & Richardson P.C.

(57) ABSTRACT

Provided is a novel heterocyclic compound which can be used as a host material for dispersing a light-emitting material in a light-emitting layer of a light-emitting element. Further provided is a light-emitting element which is driven at a low voltage and has high current efficiency. By including the light-emitting element, a light-emitting device, an electronic device, and a lighting device each with reduced power consumption are provided. The light-emitting element contains a compound in which a dibenzo[f,h]quinoline ring and a hole-transport skeleton are bonded through an arylene group. The light-emitting device, the electronic device, and the lighting device each including the light-emitting element are provided. The light-emitting element contains a heterocyclic compound having a structure represented by the following general formula (G1).

(G1)

[Chemical structure showing a fused polycyclic compound with substituents $R^{11}$, $R^{12}$, $R^{13}$, $R^{14}$, $R^{15}$, $R^{16}$, $R^{17}$, $R^{18}$, $R^{19}$, $R^{20}$, and an Ar—A group attached to a nitrogen-containing ring]

17 Claims, 22 Drawing Sheets

(56) References Cited

U.S. PATENT DOCUMENTS

| | | |
|---|---|---|
| 2010/0039024 A1 | 2/2010 | Wendeborn et al. |
| 2010/0249349 A1 | 9/2010 | Chebotareva et al. |
| 2011/0089407 A1 | 4/2011 | Schmidhalter et al. |
| 2011/0210316 A1 | 9/2011 | Kadoma et al. |
| 2014/0042413 A1 | 2/2014 | Xia et al. |
| 2014/0103327 A1 | 4/2014 | Brooks et al. |
| 2015/0001524 A1 | 1/2015 | Brooks et al. |

FOREIGN PATENT DOCUMENTS

| | | |
|---|---|---|
| JP | 2007-180148 | 7/2007 |
| JP | 2007-189001 | 7/2007 |
| JP | 2007-189001 A | 7/2007 |
| JP | 2008-239613 A | 10/2008 |
| JP | 2010-535806 A | 11/2010 |
| JP | 2010-535809 | 11/2010 |
| TW | 201111347 | 4/2011 |
| WO | 03/058667 A1 | 7/2003 |
| WO | 2004/043937 A1 | 5/2004 |
| WO | 2007/090773 A1 | 8/2007 |
| WO | 2008/031743 A1 | 3/2008 |
| WO | WO-2009/021107 | 2/2009 |
| WO | WO-2009/021126 | 2/2009 |
| WO | WO-2009/030981 | 3/2009 |
| WO | WO-2009/085344 | 7/2009 |
| WO | WO-2009/086028 | 7/2009 |
| WO | 2009/100991 A1 | 8/2009 |
| WO | 2010/132524 A1 | 11/2010 |
| WO | WO-2011/081423 | 7/2011 |

OTHER PUBLICATIONS

Taiwanese Office Action (Application No. 101124030) Dated Jan. 18, 2016.

* cited by examiner

HETEROCYCLIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Present Invention

The present invention relates to a heterocyclic compound, a light-emitting element, a light-emitting device, an electronic device, and a lighting device.

2. Description of the Related Art

In recent years, research and development have been extensively conducted on light-emitting elements using electroluminescence (EL). In a basic structure of such a light-emitting element, a layer containing a light-emitting material is interposed between a pair of electrodes. By applying voltage to this element, light emission from the light-emitting material can be obtained.

Since such a light-emitting element is of self-light-emitting type, it is considered that the light-emitting element has advantages over a liquid crystal display in that visibility of pixels is high, backlight is not required, and so on and is therefore suitable as flat panel display elements. Another major advantage of such a light-emitting element is that it can be manufactured to be thin and lightweight. A further advantage is a quite fast response speed.

Furthermore, since such a light-emitting element can be formed in a film form, planar light emission can be easily obtained; therefore, a large-area element using planar light emission can be formed. This feature is difficult to obtain by point light sources typified by an incandescent lamp and an LED or linear light sources typified by a fluorescent lamp. Accordingly, the light-emitting element is extremely effective for use as a surface light source applicable to illumination and the like.

Such light-emitting elements utilizing electroluminescence can be broadly classified according to whether a light-emitting material is an organic compound or an inorganic compound. In the case of an organic EL element in which a layer containing an organic compound used as a light-emitting material is provided between a pair of electrodes, application of voltage to the light-emitting element causes injection of electrons from a cathode and holes from an anode into the layer containing the organic compound having a light-emitting property and thus a current flows. The injected electrons and holes then lead the organic compound having a light-emitting property to its excited state, whereby light emission is obtained from the excited organic compound having a light-emitting property.

Note that excited states of the organic compound include a singlet excited state and a triplet excited state. Light emission from the singlet excited state ($S^*$) is referred to as fluorescence, and light emission from the triplet excited state ($T^*$) is referred to as phosphorescence. In addition, the statistical generation ratio in a light-emitting element is considered to be $S^*:T^*=1:3$.

With a compound that can convert energy of a singlet excited state into light emission (hereinafter called fluorescent compound), only light emission from the singlet excited state (fluorescence) is observed and that from the triplet excited state (phosphorescence) is not observed, at room temperature. Accordingly, the internal quantum efficiency (the ratio of generated photons to injected carriers) in a light-emitting element using a fluorescent compound is assumed to have a theoretical limit of 25% based on $S^*:T^*=1:3$.

In contrast, with a compound that can convert energy of a triplet excited state into light emission (hereinafter called phosphorescent compound), light emission from the triplet excited state (phosphorescence) is observed. Further, since intersystem crossing (i.e., transition from a singlet excited state to a triplet excited state) easily occurs in a phosphorescent compound, the internal quantum efficiency can be theoretically increased to 100%. In other words, the emission efficiency can be 4 times as much as that of the fluorescence compound. For this reason, light-emitting elements using a phosphorescent compound have been under active development recently so that high-efficiency light-emitting elements can be achieved.

When a light-emitting layer of a light-emitting element is formed using the phosphorescent compound described above, in order to suppress concentration quenching or quenching due to triplet-triplet annihilation in the phosphorescent compound, the light-emitting layer is often formed such that the phosphorescent compound is dispersed in a matrix of another compound. Here, the compound serving as the matrix is called host material, and the compound dispersed in the matrix like the phosphorescent compound is called guest material.

When the phosphorescent compound is used as the guest material, the host material is required to have higher triplet excitation energy (larger difference in energy between the ground state and the triplet excited state) than the phosphorescent compound.

Since the singlet excitation energy (the difference in energy between the ground state and the singlet excited state) is greater than the triplet excitation energy, a material that has high triplet excitation energy also has high singlet excitation energy. Therefore, the above material that has high triplet excitation energy is also effective in a light-emitting element using a fluorescent compound as a light-emitting material.

Studies have been conducted on a variety of compounds which can be used as the host material when a phosphorescent compound is used as the guest material. For example, studies have been conducted on compounds having triphenylene rings or having dibenzo[f,h]quinoxaline rings (e.g., see Patent Documents 1 and 2).

REFERENCE

Patent Document

[Patent Document 1] Published Translation of PCT International Application No. 2010-535806
[Patent Document 2] Japanese Published Patent Application No. 2007-189001

SUMMARY OF THE INVENTION

As reported in Patent Document 1 or 2, although host materials of phosphorescent compounds have been developed, there is room for improvement in terms of emission efficiency, reliability, light-emitting characteristics, synthesis efficiency, cost, or the like, and further development is required for obtaining more excellent phosphorescent compounds.

In view of the above problem, an object of one embodiment of the present invention is to provide a novel heterocyclic compound which can be used as a host material for dispersing a light-emitting material in a light-emitting layer of a light-emitting element, in particular, a novel heterocyclic compound which can be suitably used as a host material when a phosphorescent compound is used as a light-emitting material.

Another object of one embodiment of the present invention is to provide a light-emitting element which is driven at a low voltage and has high current efficiency. Another object of one embodiment of the present invention is to provide a light-emitting device, an electronic device, and a lighting device in each of which power consumption is reduced by use of the above light-emitting element.

One embodiment of the present invention is a compound in which a dibenzo[f,h]quinoline ring and a hole-transport skeleton are bonded through an arylene group.

The compound according to one embodiment of the present invention has a hole-transport skeleton in addition to a dibenzo[f,h]quinoline ring, making it easy to accept holes. Therefore, by using the compound according to one embodiment of the present invention as a host material in a light-emitting layer, electrons and holes can be easily recombined in a light-emitting layer. Moreover, since a dibenzo[f,h]quinoline ring and a hole-transport skeleton are bonded through an arylene group, decreases in band gap and triplet excitation energy of this compound can be smaller than those of a compound in which a dibenzo[f,h]quinoline ring and a hole-transport skeleton are directly bonded. By using the compound, in which the dibenzo[f,h]quinoline ring and the hole-transport skeleton are bonded through the arylene group, for a light-emitting element, the element can have high current efficiency.

As the hole-transport skeleton, a π-electron rich heteroaromatic ring is preferable. As the π-electron rich heteroaromatic ring, a carbazole ring, a dibenzofuran ring, or a dibenzothiophene ring is preferable. As the arylene group, any of a substituted or unsubstituted phenylene group and a substituted or unsubstituted biphenyldiyl group is preferable.

As the compound in which a dibenzo[f,h]quinoline ring and a hole-transport skeleton are bonded through an arylene group, a heterocyclic compound having any of the following structures can be given.

One embodiment of the present invention is a heterocyclic compound having a structure represented by the following general formula (G0).

E—Ar—A (G0)

In the general formula (G0), A represents any of a substituted or unsubstituted carbazolyl group, a substituted or unsubstituted dibenzothiophenyl group, and a substituted or unsubstituted dibenzofuranyl group; E represents a substituted or unsubstituted dibenzo[f,h]quinoline ring; and Ar represents an arylene group having 6 to 13 carbon atoms. The arylene group may have one or more substituents that may be bonded to form a ring.

Another embodiment of the present invention is a heterocyclic compound having a structure represented by the following general formula (G1).

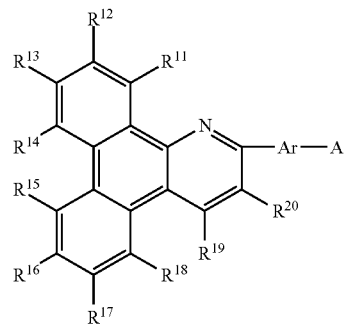

(G1)

In the general formula (G1), A represents any of a substituted or unsubstituted carbazolyl group, a substituted or unsubstituted dibenzothiophenyl group, and a substituted or unsubstituted dibenzofuranyl group; $R^{11}$ to $R^{20}$ separately represent any of hydrogen, an alkyl group having 1 to 4 carbon atoms, and a substituted or unsubstituted aryl group having 6 to 13 carbon atoms; and Ar represents an arylene group having 6 to 13 carbon atoms. The arylene group may have one or more substituents that may be bonded to form a ring.

Another embodiment of the present invention is a heterocyclic compound having a structure represented by the following general formula (G2-1).

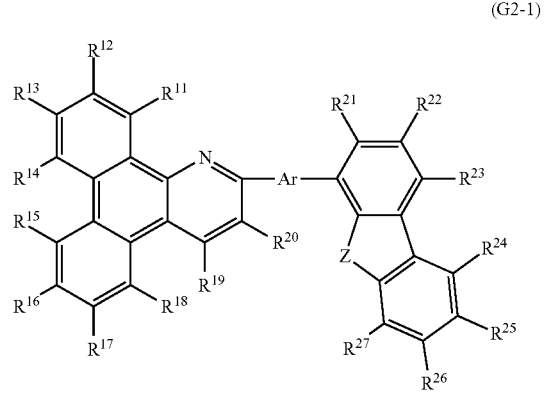

(G2-1)

In the general formula (G2-1), Z represents oxygen or sulfur; $R^{11}$ to $R^{27}$ separately represent any of hydrogen, an alkyl group having 1 to 4 carbon atoms, and a substituted or unsubstituted aryl group having 6 to 13 carbon atoms; and Ar represents an arylene group having 6 to 13 carbon atoms. The arylene group may have a substituents or substituents that may be bonded to form a ring.

Another embodiment of the present invention is a heterocyclic compound having a structure represented by the following general formula (G2-2).

(G2-2)

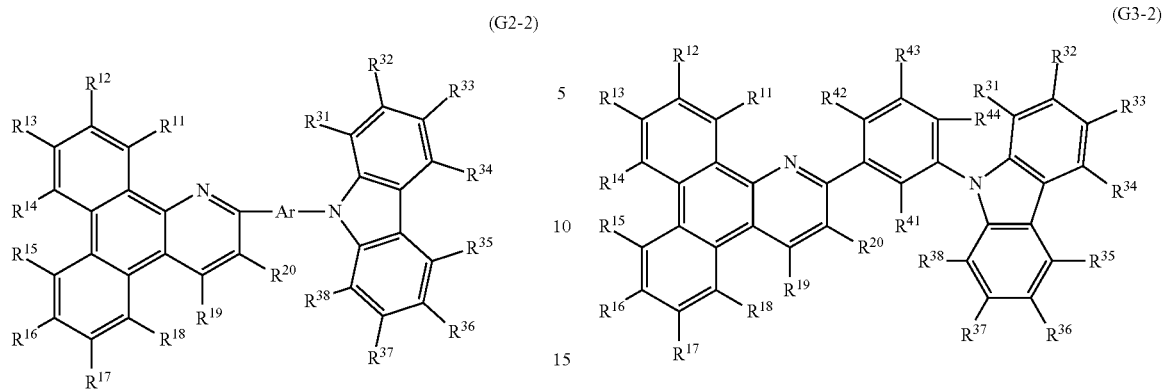

In the general formula (G2-2), $R^{11}$ to $R^{20}$ and $R^{31}$ to $R^{38}$ separately represent any of hydrogen, an alkyl group having 1 to 4 carbon atoms, and a substituted or unsubstituted aryl group having 6 to 13 carbon atoms; and Ar represents an arylene group having 6 to 13 carbon atoms. The arylene group may have one or more substituents that may be bonded to form a ring.

In the general formulas (G2-1) and (G2-2), Ar is preferably either a substituted or unsubstituted phenylene group or a substituted or unsubstituted biphenyldiyl group. In particular, Ar is preferably a substituted or unsubstituted phenylene group. For a high triplet excitation energy level, Ar is preferably a substituted or unsubstituted m-phenylene group.

Another embodiment of the present invention is a heterocyclic compound having a structure represented by the following general formula (G3-1).

(G3-1)

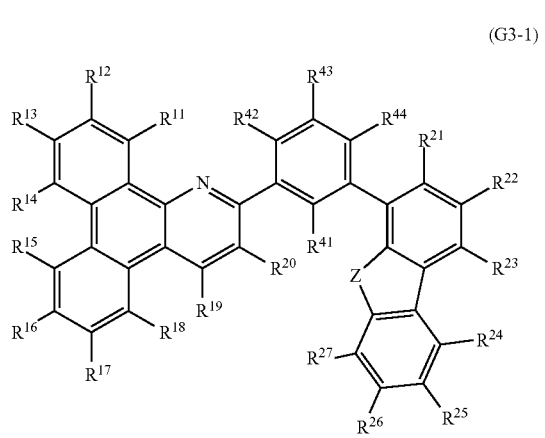

In the general formula (G3-1), Z represents oxygen or sulfur; and $R^{11}$ to $R^{27}$ and $R^{41}$ to $R^{44}$ separately represent any of hydrogen, an alkyl group having 1 to 4 carbon atoms, and a substituted or unsubstituted aryl group having 6 to 13 carbon atoms.

Another embodiment of the present invention is a heterocyclic compound having a structure represented by the following general formula (G3-2).

(G3-2)

In the general formula (G3-2), $R^{11}$ to $R^{20}$, $R^{31}$ to $R^{38}$, and $R^{41}$ to $R^{44}$ separately represent any of hydrogen, an alkyl group having 1 to 4 carbon atoms, and a substituted or unsubstituted aryl group having 6 to 13 carbon atoms.

Another embodiment of the present invention is a light-emitting element containing the above heterocyclic compound between a pair of electrodes. In particular, a light-emitting layer preferably contains the heterocyclic compound.

A light-emitting device, an electronic device, and a lighting device each using the above light-emitting element also belong to the category of the present invention. Note that the light-emitting device in this specification includes an image display device, illumination device, and a light source. In addition, the light-emitting device includes, in its category, all of a module in which a connector such as a flexible printed circuit (FPC), a tape automated bonding (TAB) tape or a tape carrier package (TCP) is connected to a panel, a module in which a printed wiring board is provided on the tip of a TAB tape or a TCP, and a module in which an integrated circuit (IC) is directly mounted on a light-emitting element by a chip on glass (COG) method.

One embodiment of the present invention can provide a novel heterocyclic compound which can be used as a host material for dispersing a light-emitting material in a light-emitting layer of a light-emitting element. Another embodiment of the present invention can provide a light-emitting element which is driven at a low voltage and has high current efficiency. By using the light-emitting element, another embodiment of the present invention can provide a light-emitting device, an electronic device, and a lighting device each with reduced power consumption.

DETAILED DESCRIPTION OF THE INVENTION

Figure 1A:
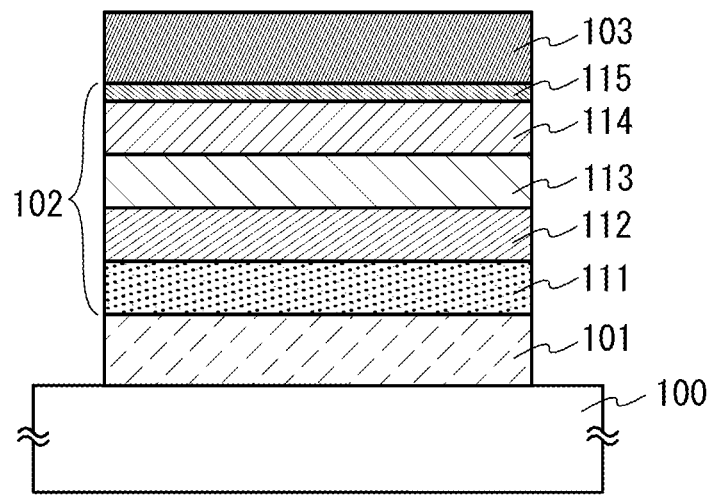
FIGS. 1A and 1B illustrate light emitting elements according to embodiments of the present invention.

Hereinafter, embodiments of the present invention will be described with reference to the drawings. Note that the present invention is not limited to the following description, and it will be easily understood by those skilled in the art that various changes and modifications can be made without departing from the spirit and scope of the present invention. Therefore, the present invention should not be construed as being limited to the description in the following embodiments.

Embodiment 1

Embodiment 1 will show a heterocyclic compound according to one embodiment of the present invention.

One embodiment of the present invention is a heterocyclic compound represented by the general formula (G0).

$$E\text{-}Ar\text{-}A \quad (G0)$$

In the general formula (G0), A represents any of a substituted or unsubstituted carbazolyl group, a substituted or unsubstituted dibenzothiophenyl group, and a substituted or unsubstituted dibenzofuranyl group; E represents a substituted or unsubstituted dibenzo[f,h]quinoline ring; and Ar represents an arylene group having 6 to 13 carbon atoms. The arylene group may have one or more substituents that may be bonded to form a ring. Note that the number of carbon atoms of an aryl group and an arylene group given in this specification refers to the number of carbon atoms which form a ring in the main skeleton and does not include the number of carbon atoms in a substituent which is bonded to the main skeleton.

Another embodiment of the present invention is a heterocyclic compound represented by the general formula (G1).

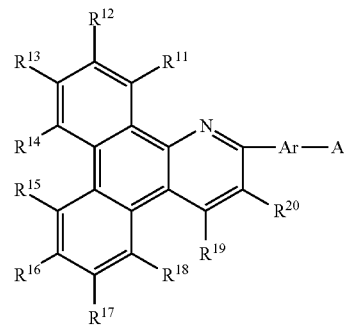

(G1)

In the general formula (G1), A represents any of a substituted or unsubstituted carbazolyl group, a substituted or unsubstituted dibenzothiophenyl group, and a substituted or unsubstituted dibenzofuranyl group; $R^{11}$ to $R^{20}$ separately represent any of hydrogen, an alkyl group having 1 to 4 carbon atoms, and a substituted or unsubstituted aryl group having 6 to 13 carbon atoms; and Ar represents an arylene group having 6 to 13 carbon atoms. The arylene group may have one or more substituents that may be bonded to form a ring.

Another embodiment of the present invention is a heterocyclic compound having a structure represented by the following general formula (G2-1).

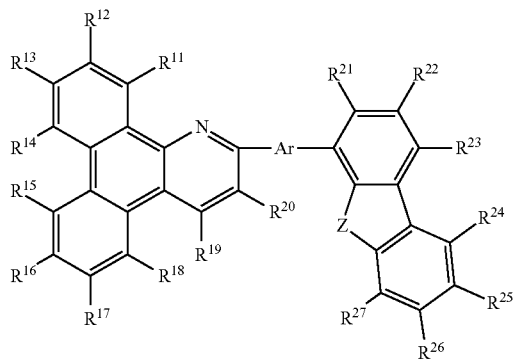

(G2-1)

In the general formula (G2-1), Z represents oxygen or sulfur; $R^{11}$ to $R^{27}$ separately represent any of hydrogen, an alkyl group having 1 to 4 carbon atoms, and a substituted or unsubstituted aryl group having 6 to 13 carbon atoms; and Ar represents an arylene group having 6 to 13 carbon atoms. The arylene group may have one or more substituents that may be bonded to form a ring.

Another embodiment of the present invention is a heterocyclic compound having a structure represented by the following general formula (G2-2).

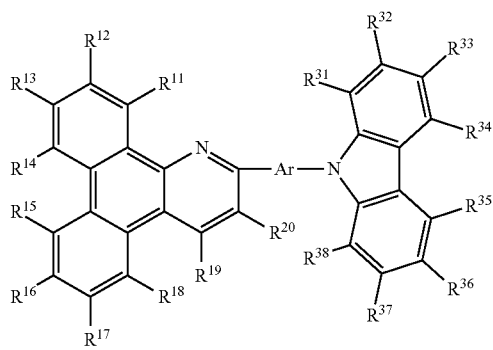

(G2-2)

In the general formula (G2-2), $R^{11}$ to $R^{20}$ and $R^{31}$ to $R^{38}$ separately represent any of hydrogen, an alkyl group having 1 to 4 carbon atoms, and a substituted or unsubstituted aryl group having 6 to 13 carbon atoms; and Ar represents an arylene group having 6 to 13 carbon atoms. The arylene group may have one or more substituents that may be bonded to form a ring.

In the general formulas (G2-1) and (G2-2), Ar is preferably either a substituted or unsubstituted phenylene group or a substituted or unsubstituted biphenyldiyl group. In particular, Ar is preferably a substituted or unsubstituted phenylene group. For a high triplet excitation energy level, Ar is preferably a substituted or unsubstituted m-phenylene group.

Another embodiment of the present invention is a heterocyclic compound having a structure represented by the following general formula (G3-1).

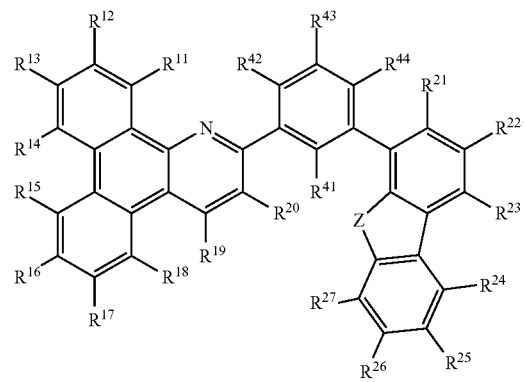

(G3-1)

In the general formula (G3-1), Z represents oxygen or sulfur; and $R^{11}$ to $R^{27}$ and $R^{41}$ to $R^{44}$ separately represent any of hydrogen, an alkyl group having 1 to 4 carbon atoms, and a substituted or unsubstituted aryl group having 6 to 13 carbon atoms.

Another embodiment of the present invention is a heterocyclic compound having a structure represented by the following general formula (G3-2).

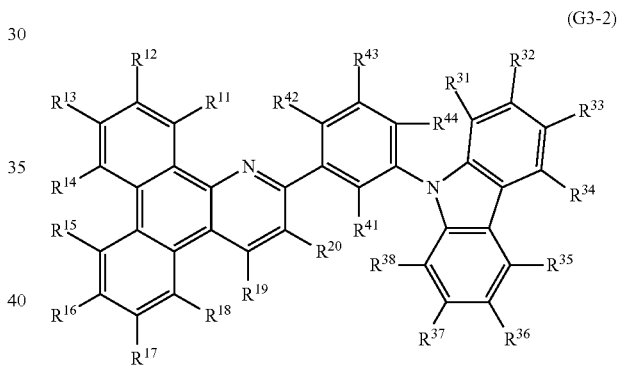

(G3-2)

In the general formula (G3-2), $R^{11}$ to $R^{20}$, $R^{31}$ to $R^{38}$, and $R^{41}$ to $R^{44}$ separately represent any of hydrogen, an alkyl group having 1 to 4 carbon atoms, and a substituted or unsubstituted aryl group having 6 to 13 carbon atoms.

Examples of specific structures of Ar in the general formulas (G0), (G1), (G2-1), and (G2-2) include substituents represented by structural formulas (1-1) to (1-15).

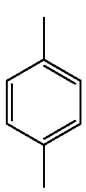

(1-1)

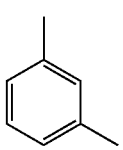

(1-2)

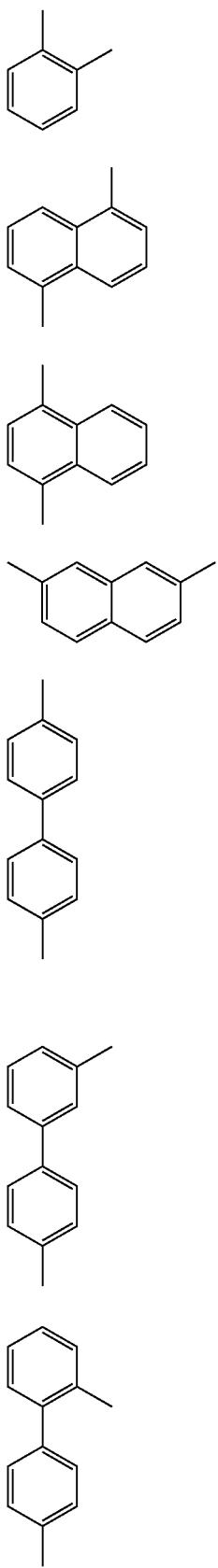
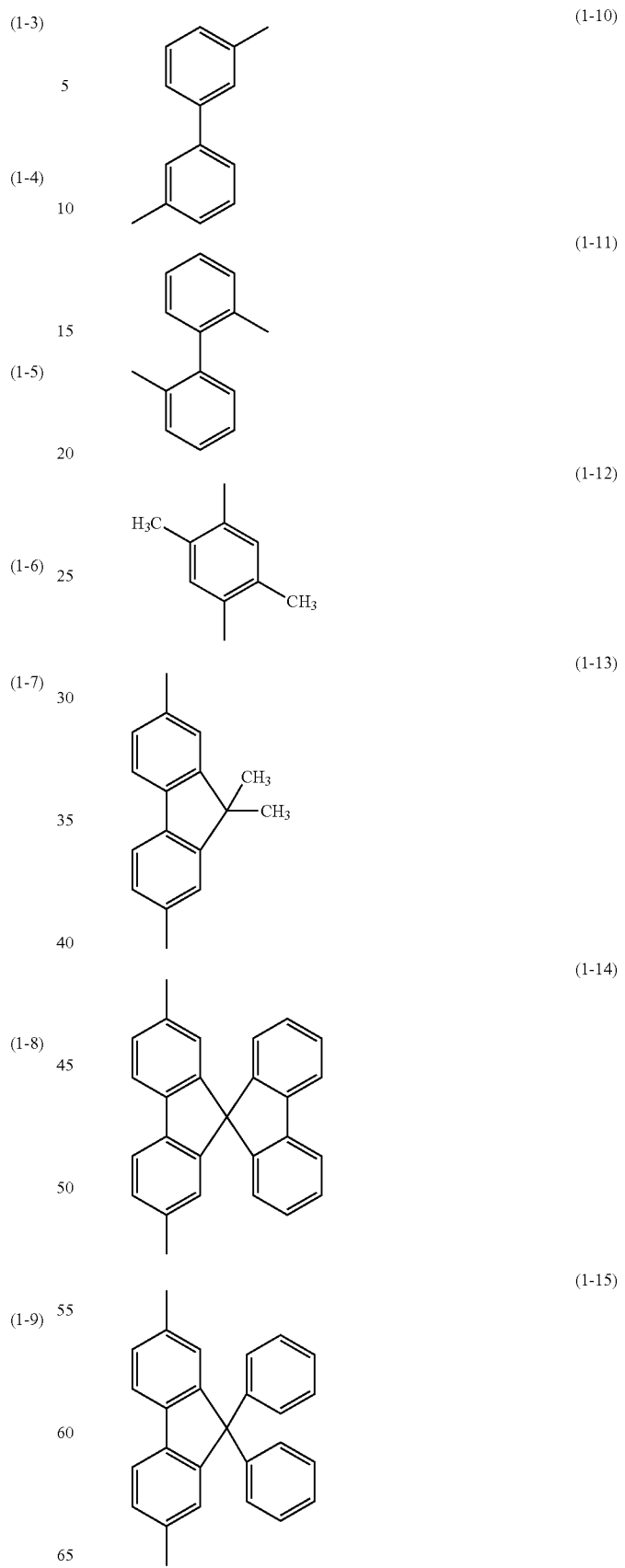

Examples of specific structures of $R^{11}$ to $R^{27}$, $R^{31}$ to $R^{38}$, and $R^{41}$ to $R^{44}$ in the general formulas (G1), (G2-1), (G2-2), (G3-1), and (G3-2) include substituents represented by structural formulas (2-1) to (2-23).
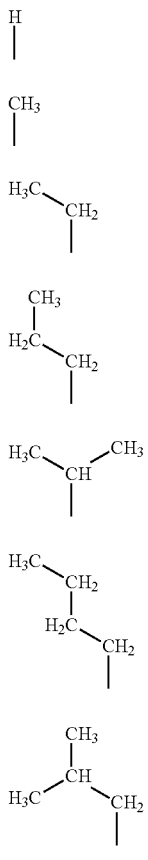
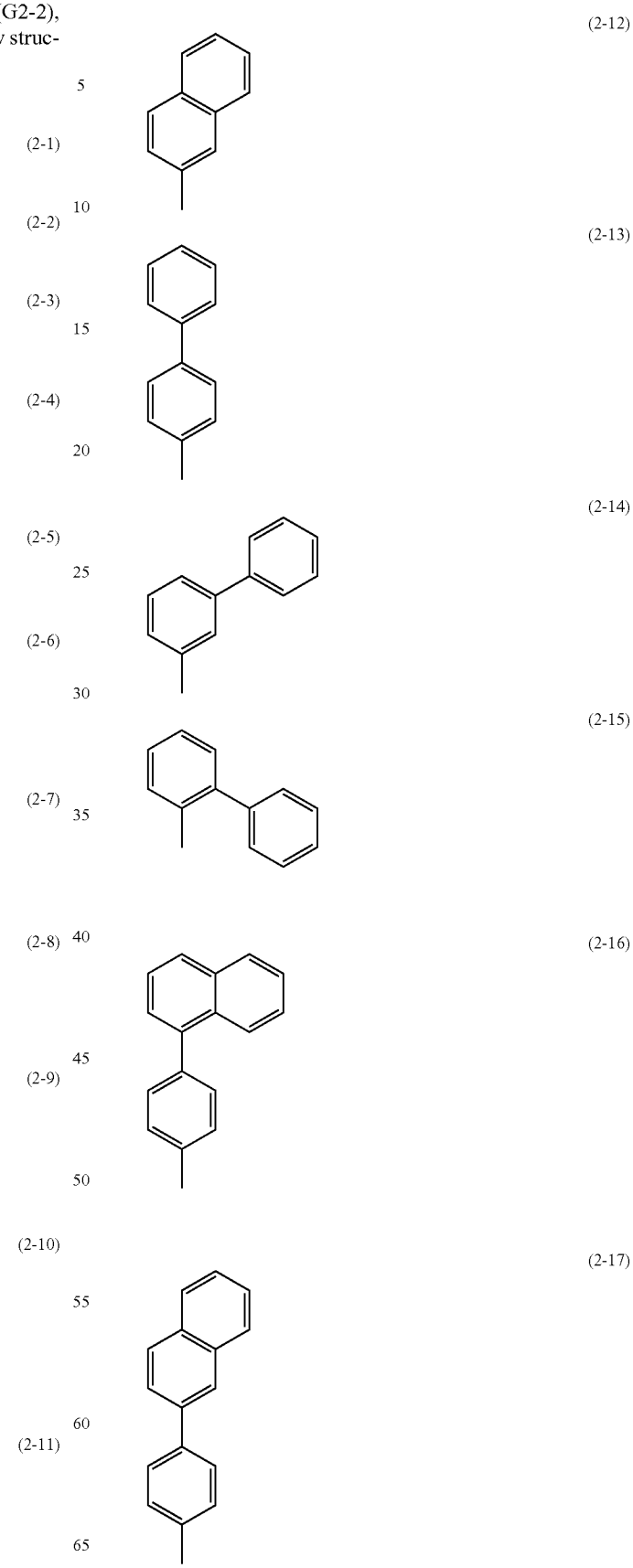

(2-18)
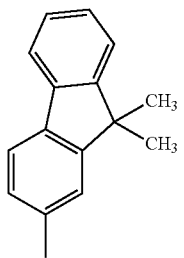
(2-19)
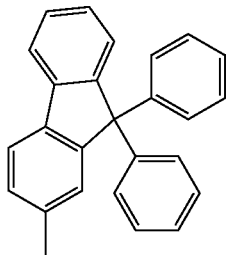
(2-20)
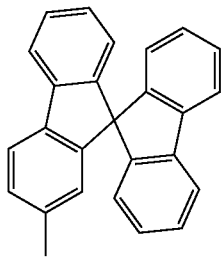
(2-21)
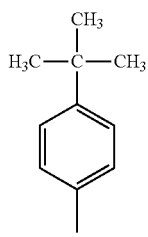
(2-22)
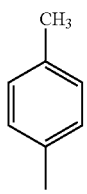
(2-23)
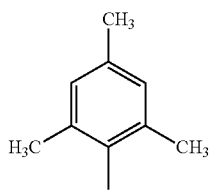
(100)
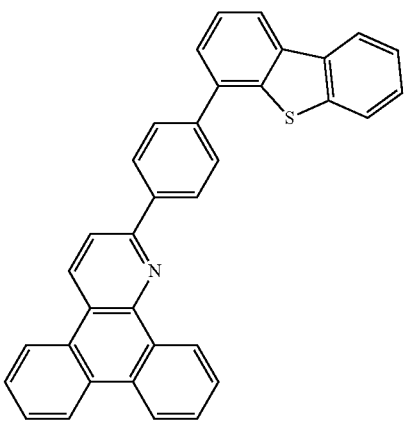
(101)
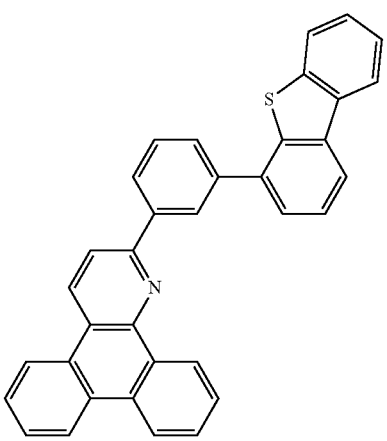
(102)
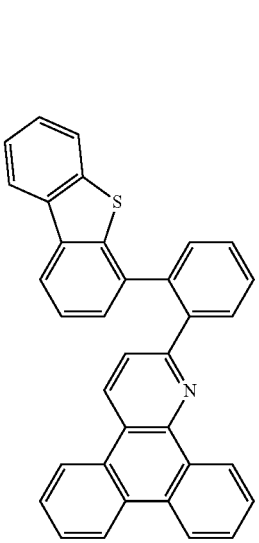
Examples of the heterocyclic compound represented by the general formula (G1) specifically include, but are not limited to, heterocyclic compounds represented by structural formulas (100) to (154), (200) to (254), and (300) to (354).

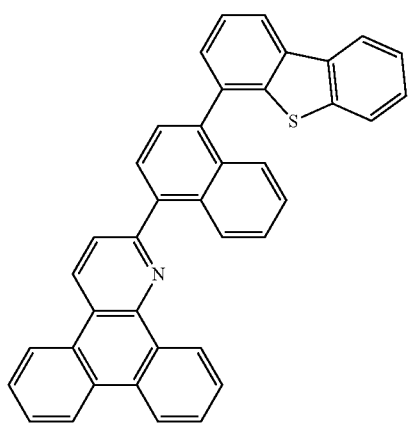
(103)
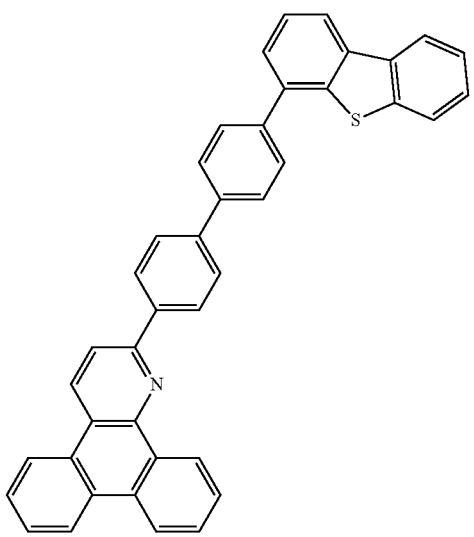
(106)
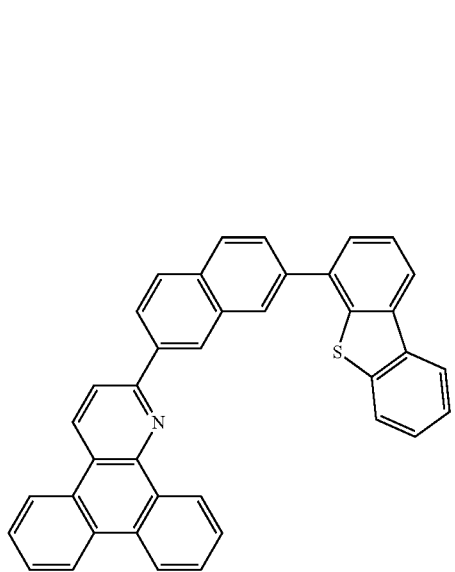
(104)
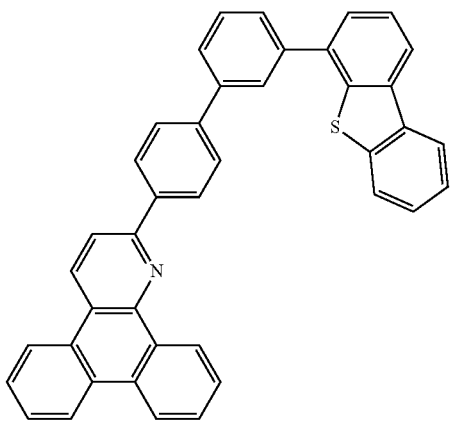
(107)
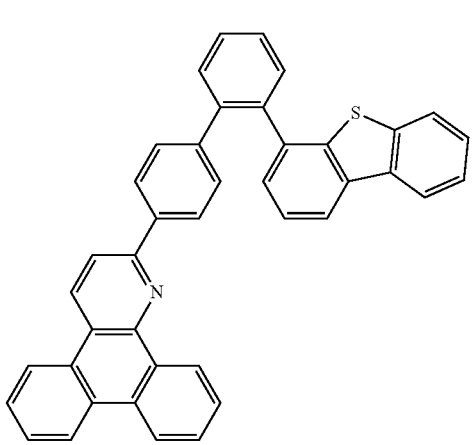
(105)
(108)

(109)
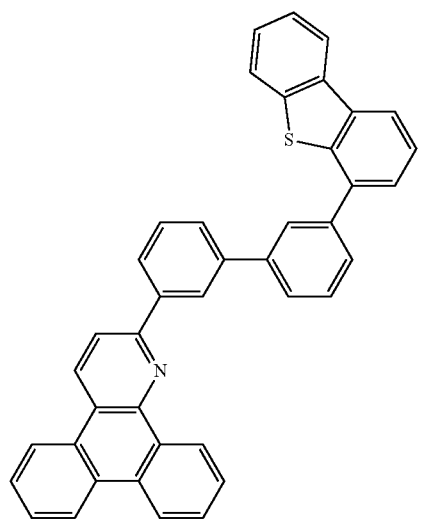
(110)
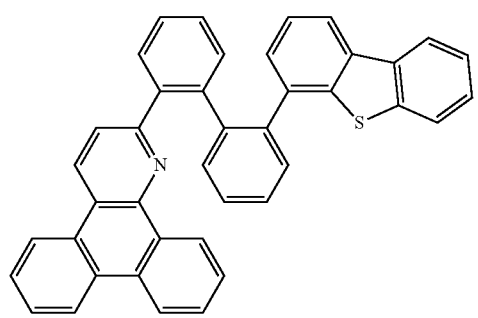
(111)
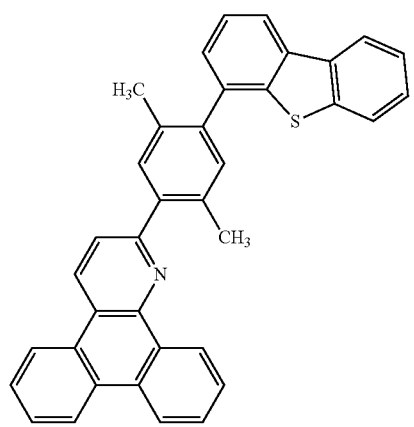
(112)
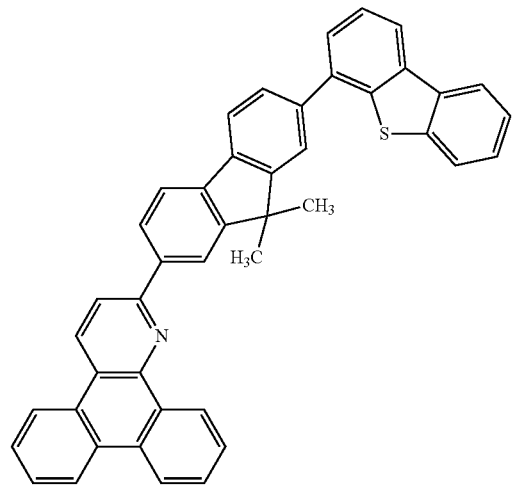
(113)
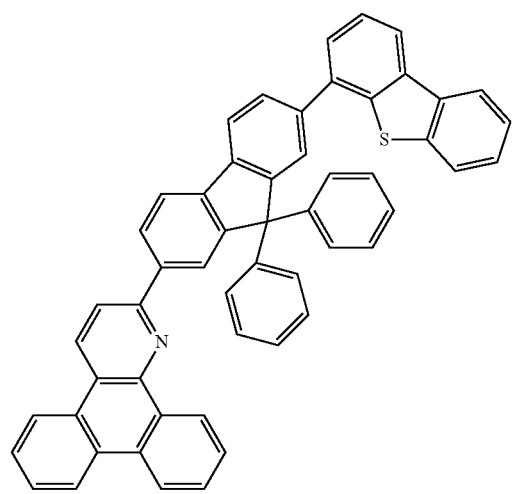
(114)
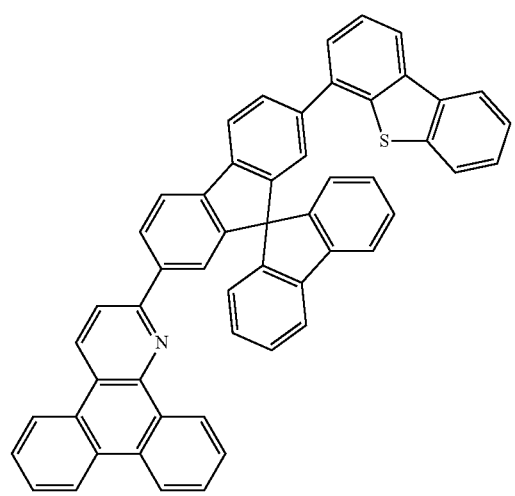

(115)
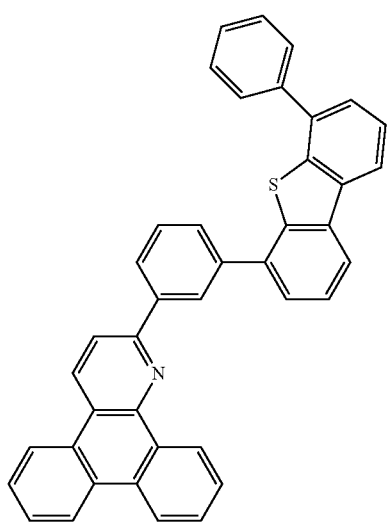
(116)
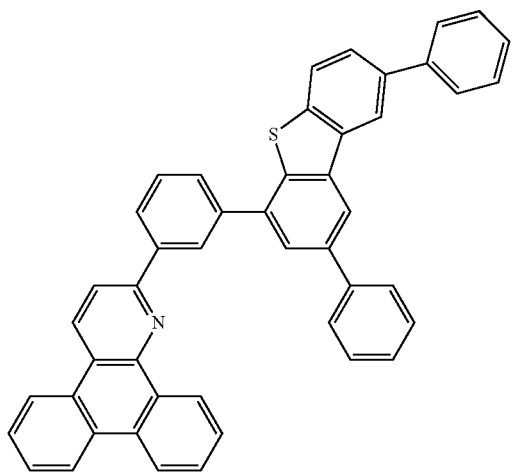
(117)
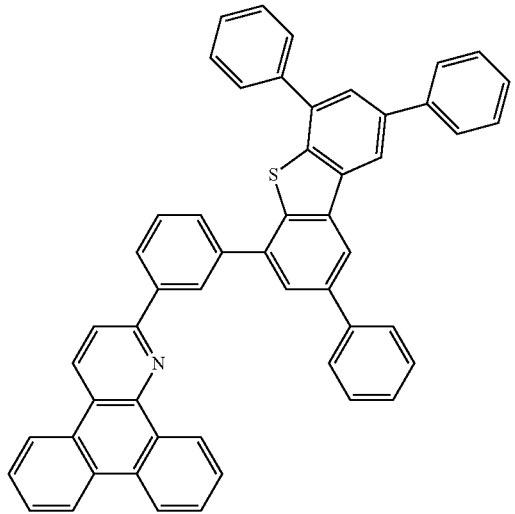
(118)
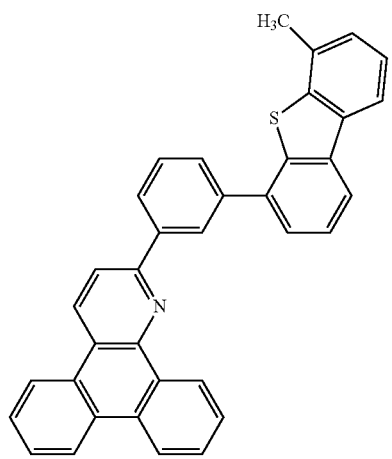
(119)
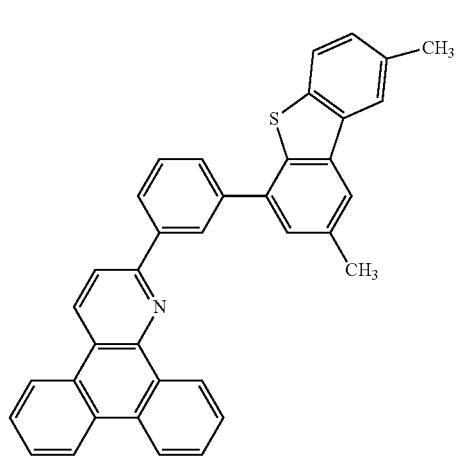
(120)
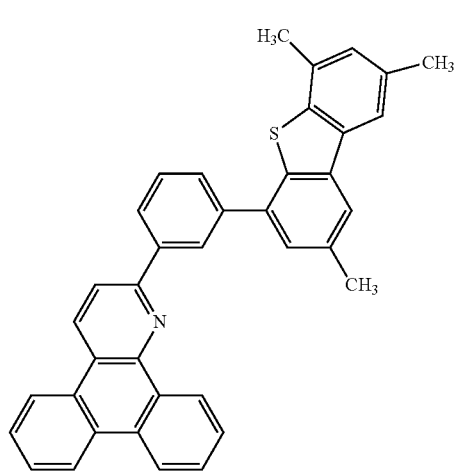

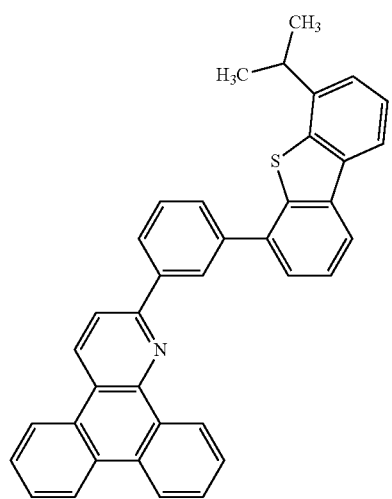
(121)
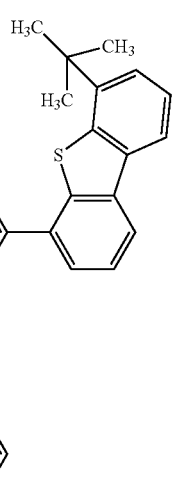
(122)
(123)
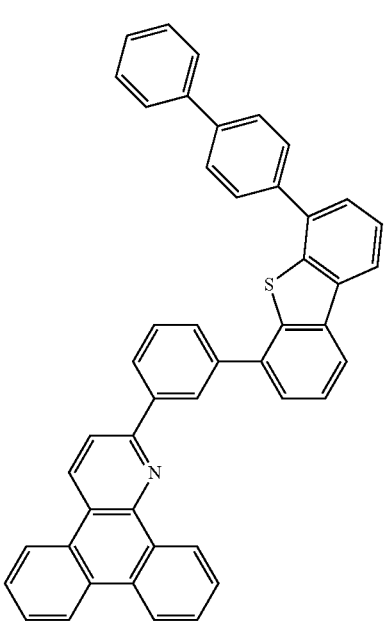
(124)
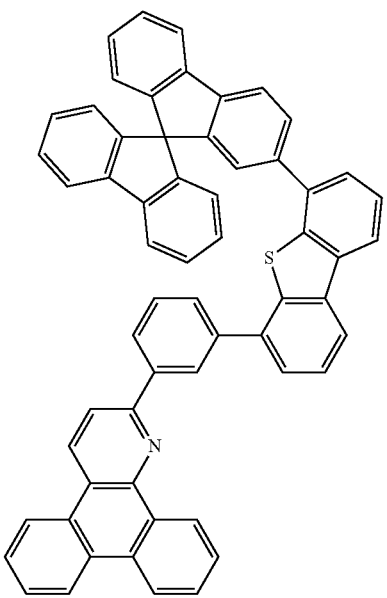
(125)

(126)
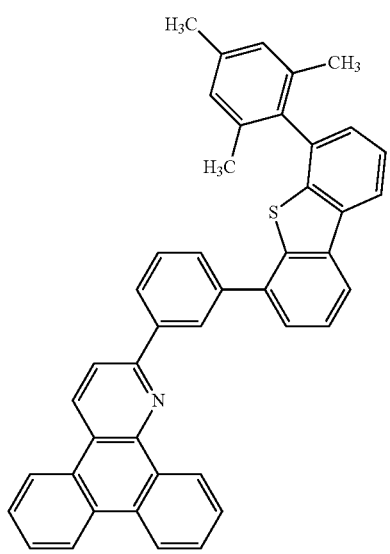
(127)
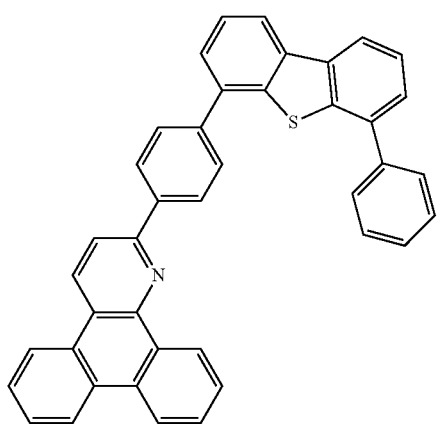
(128)
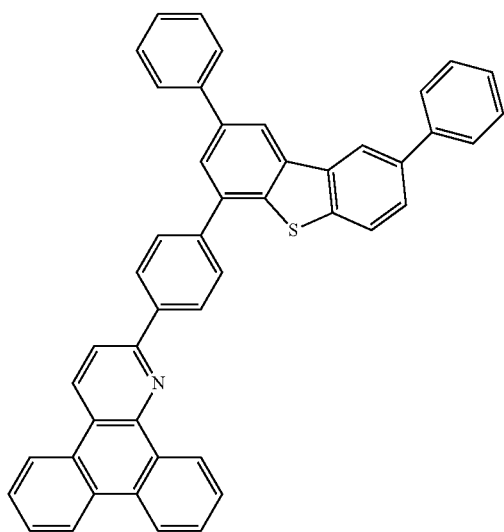
(129)
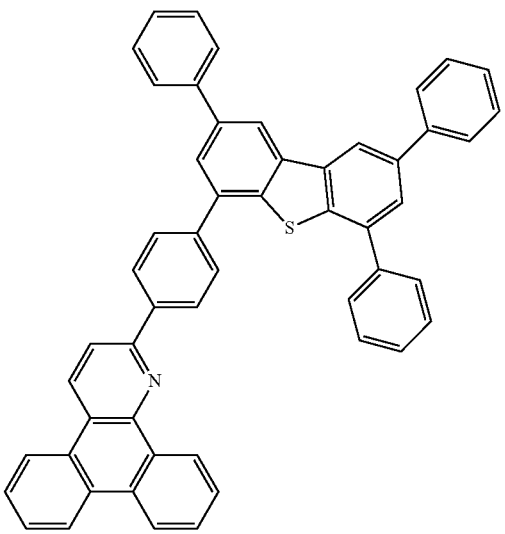
(130)
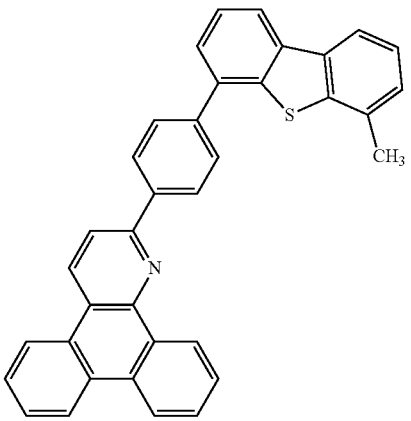
(131)
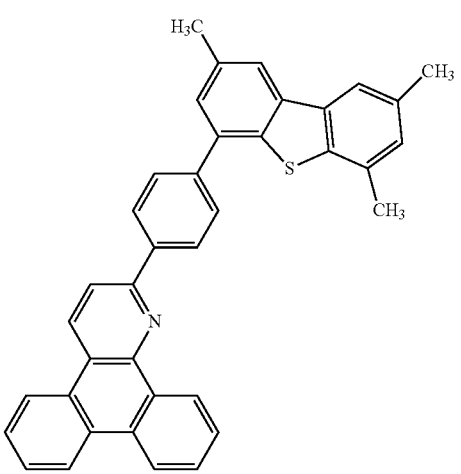

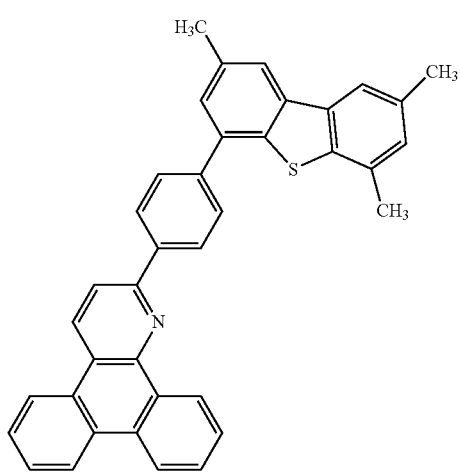 (132)
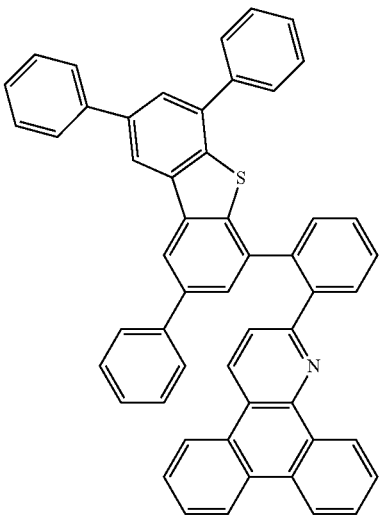 (135)
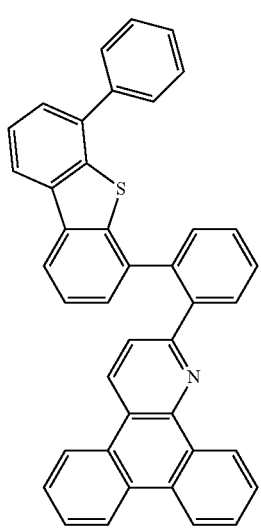 (133)
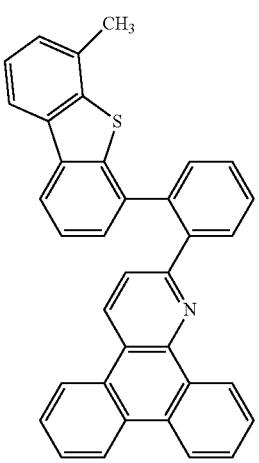 (136)
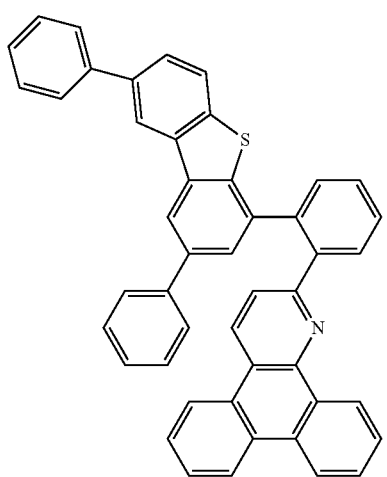 (134)
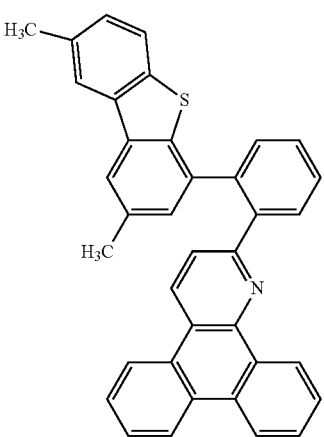 (137)

(138) 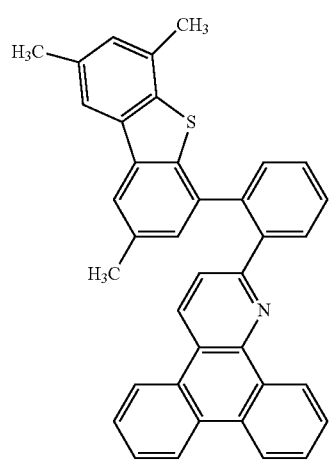
(139) 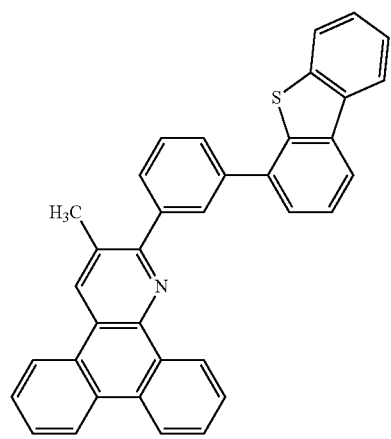
(140) 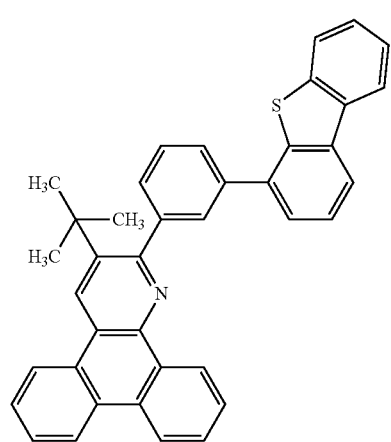
(141) 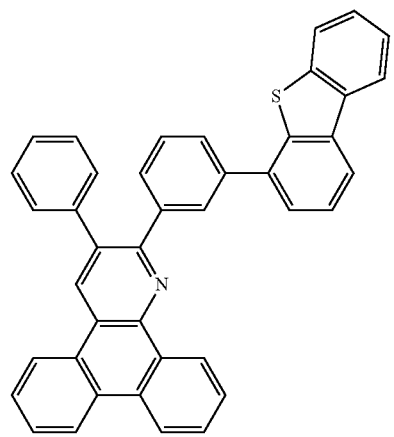
(142) 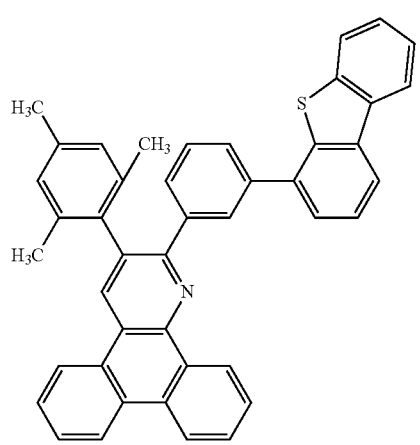
(143) 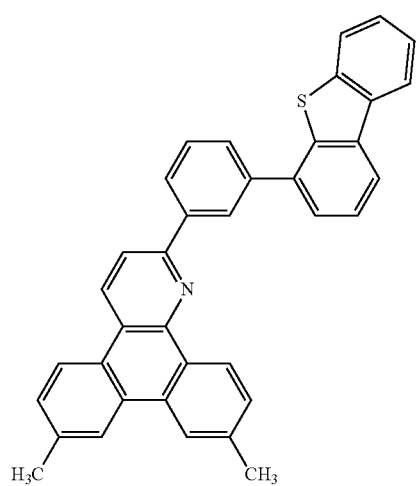

-continued
(144)
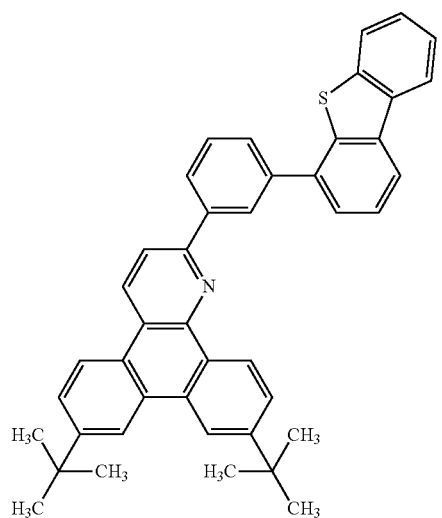
(145)
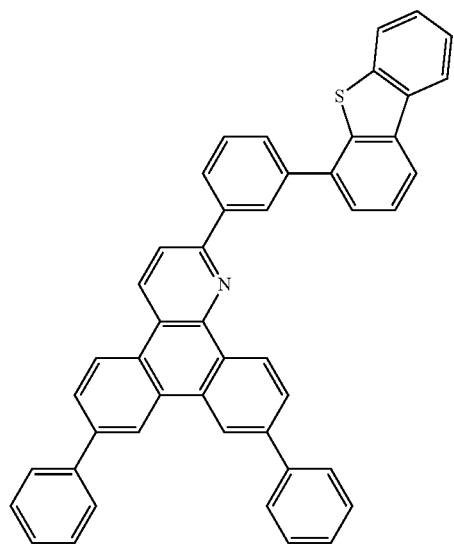
(146)
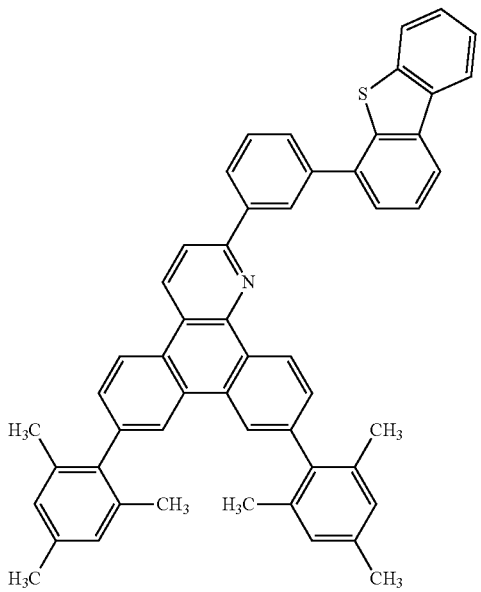
(147)
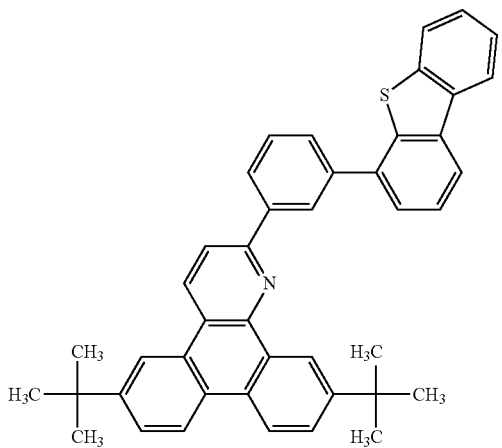
(148)
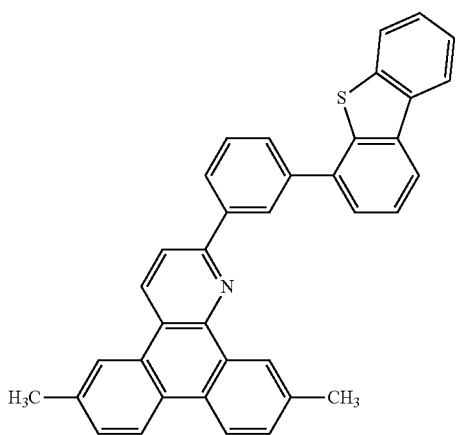

-continued
(149)
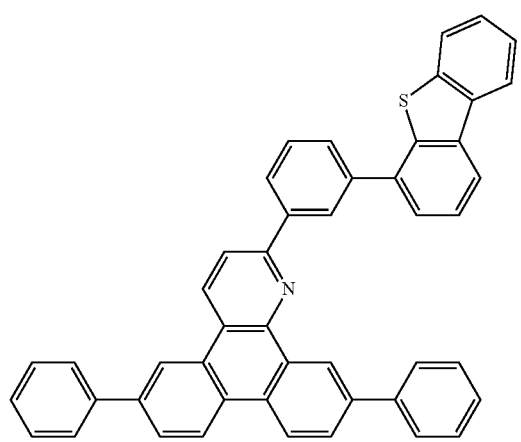
(150)
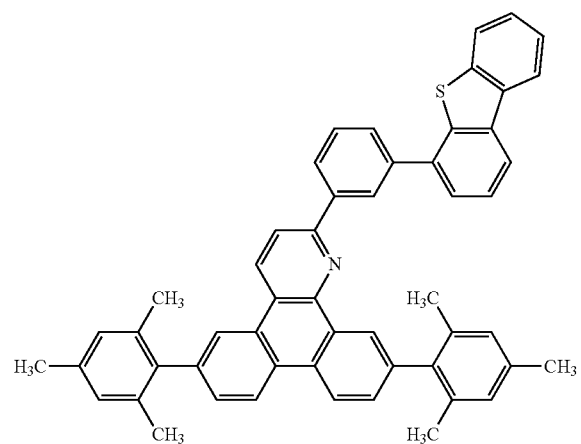
(151)
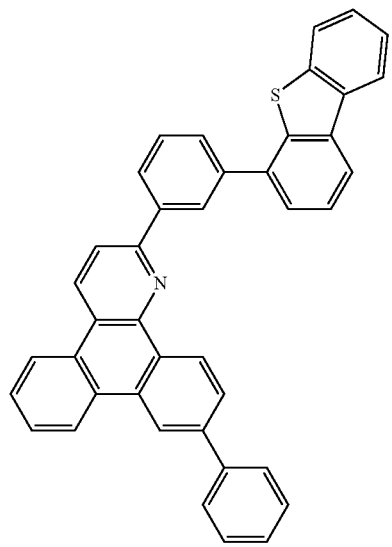
-continued
(152)
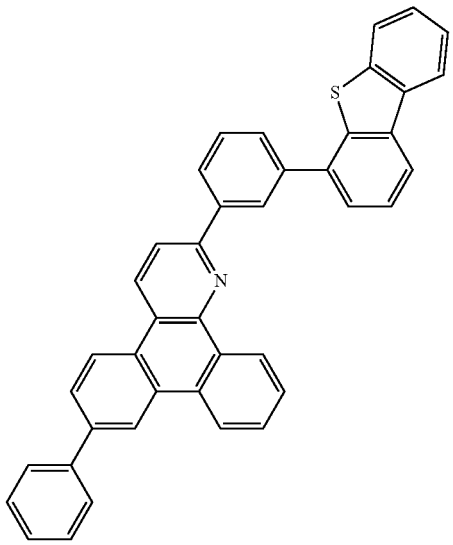
(153)
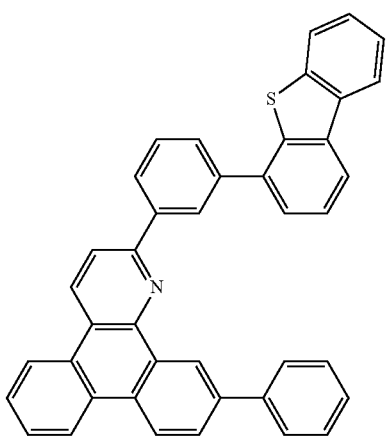
(154)
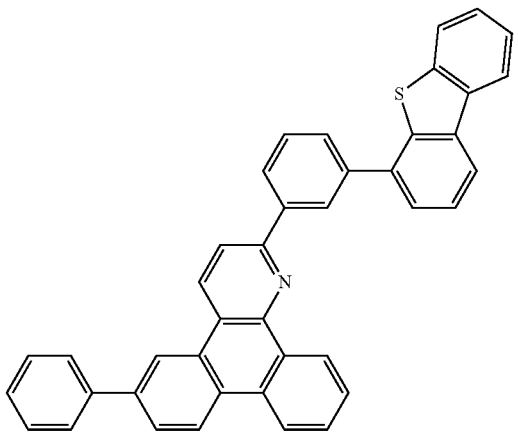

(200) 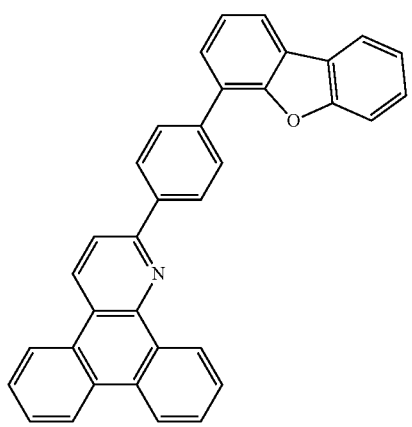
(201) 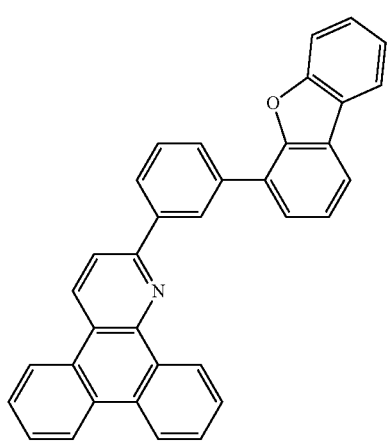
(202) 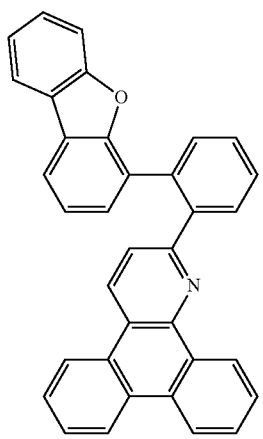
(203) 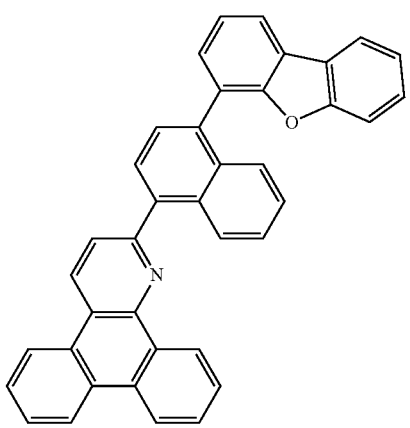
(204) 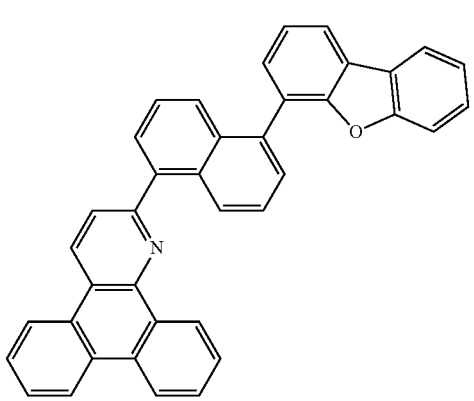
(205) 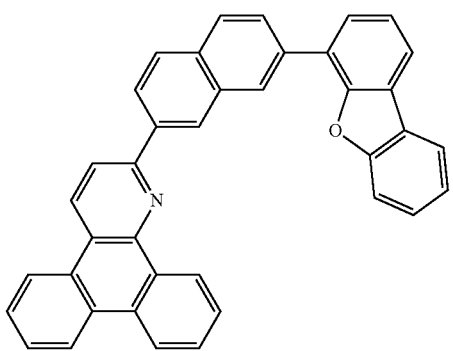

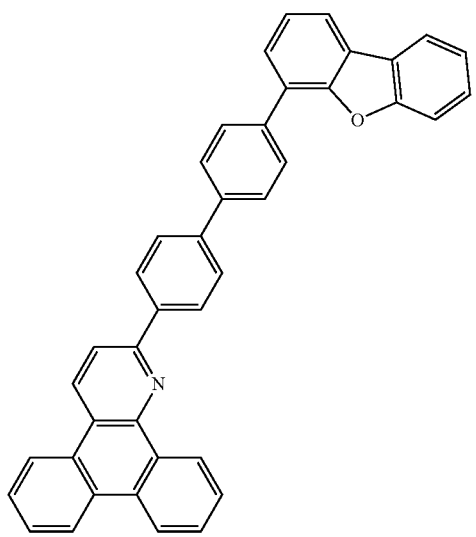
(206)
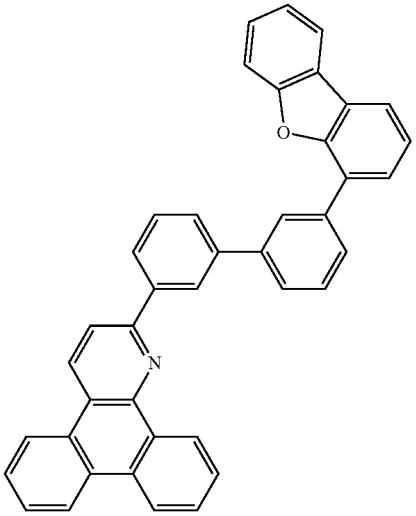
(209)
(207)
(210)
(208)
(211)

(212)
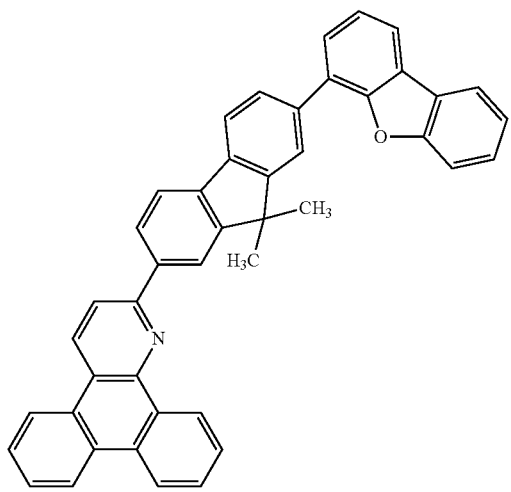
(213)
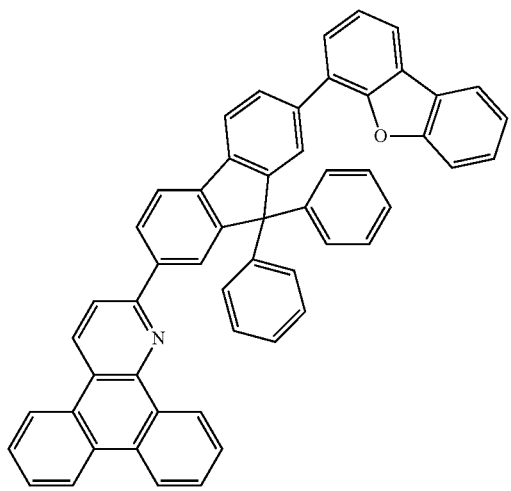
(214)
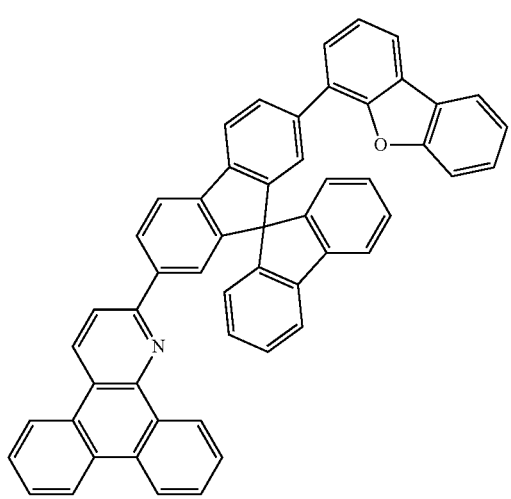
(215)
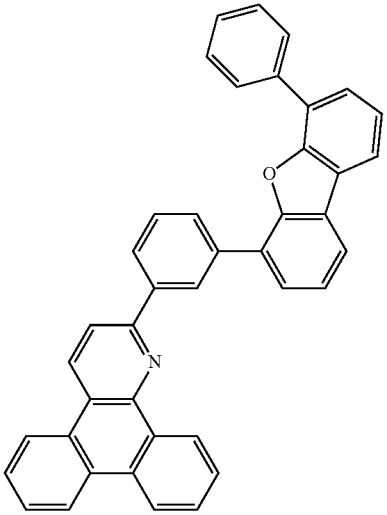
(216)
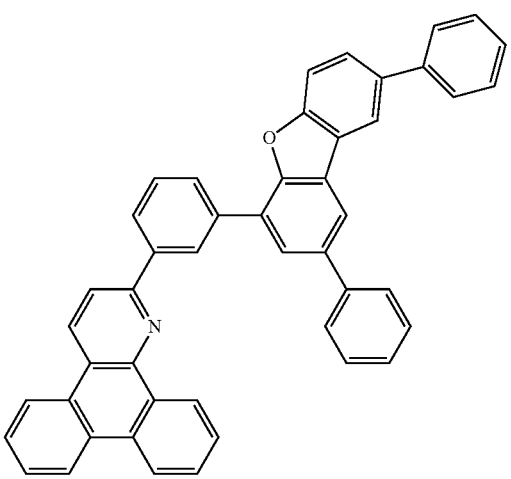
(217)
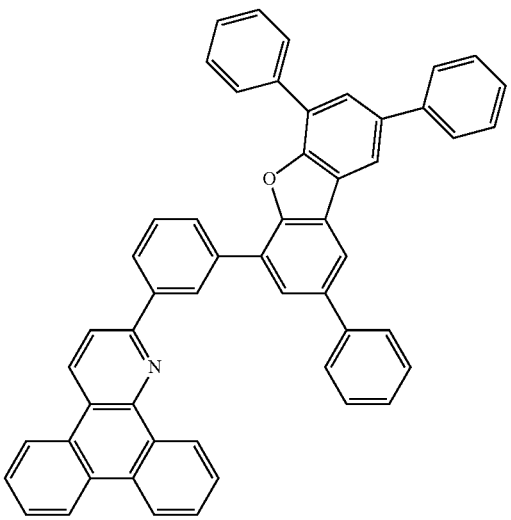

(218)
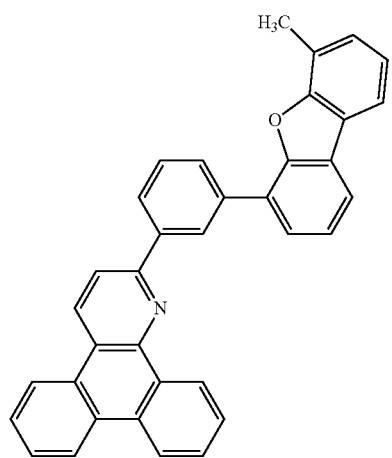
(219)
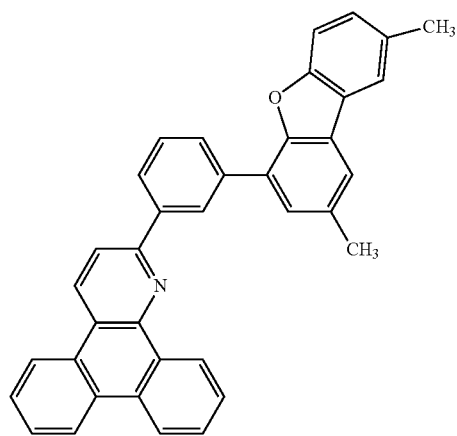
(220)
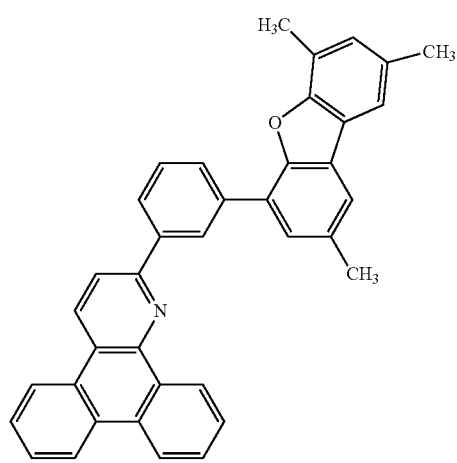
(221)
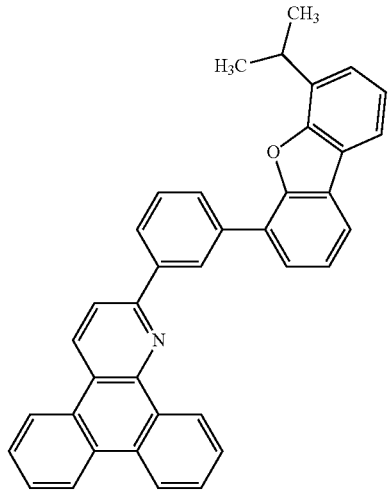
(222)
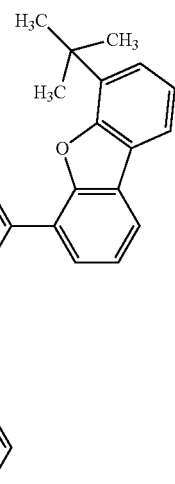
(223)
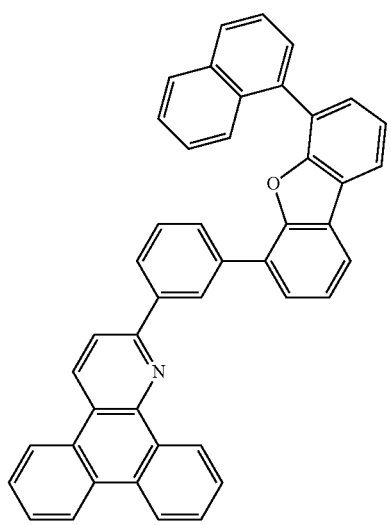

(224)
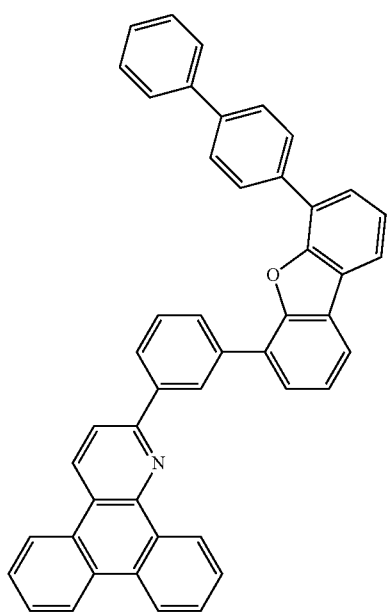
(225)
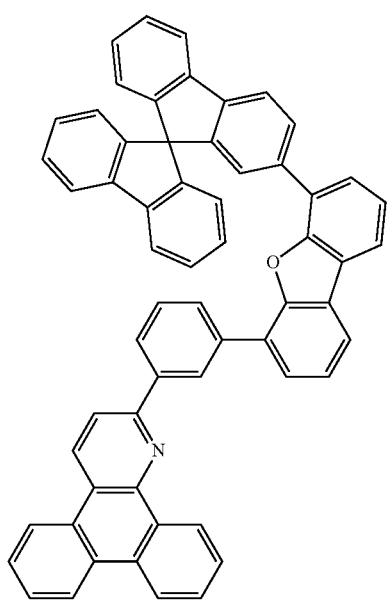
(226)
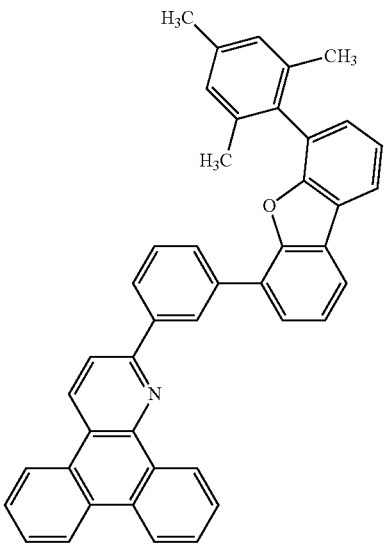
(227)
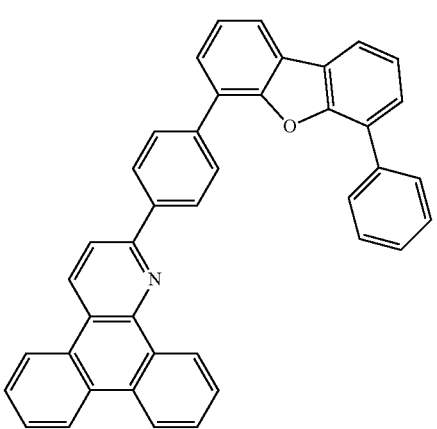
(228)
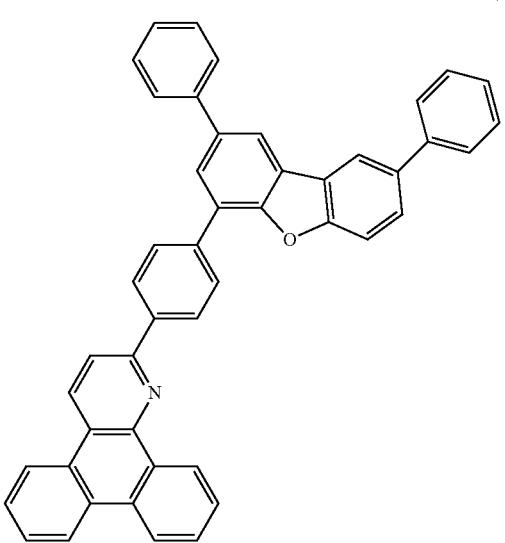

(229)
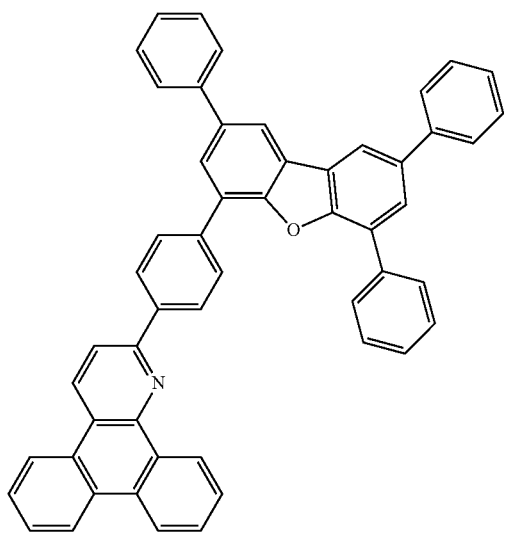
(230)
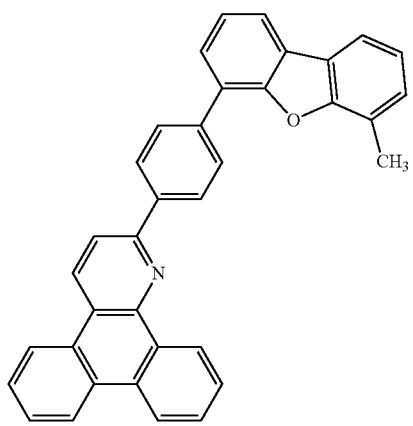
(231)
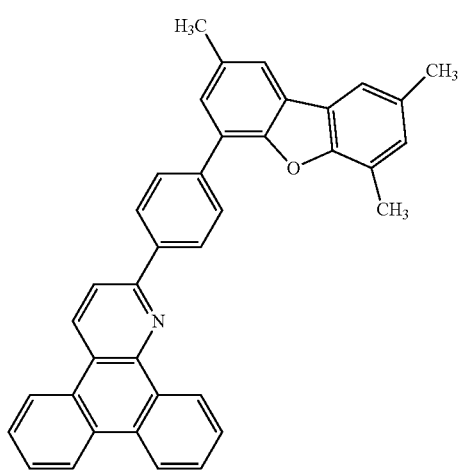
(232)
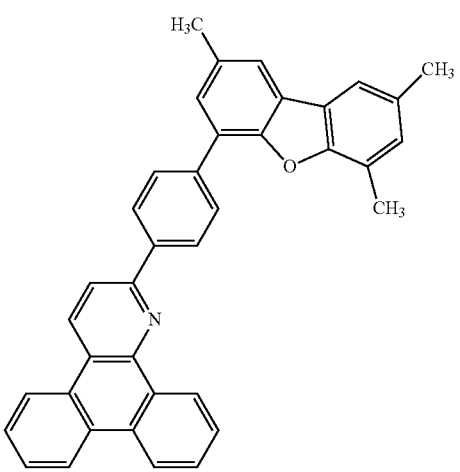
(233)
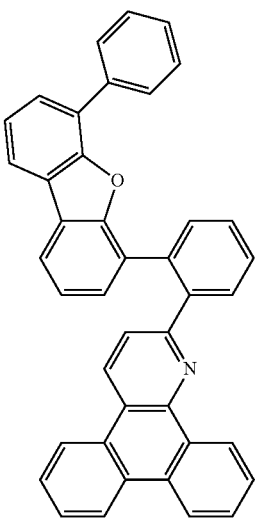
(234)
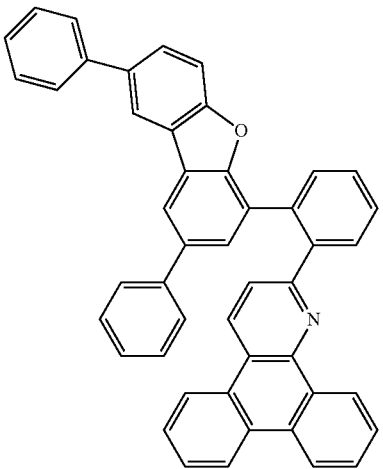

-continued
(235)
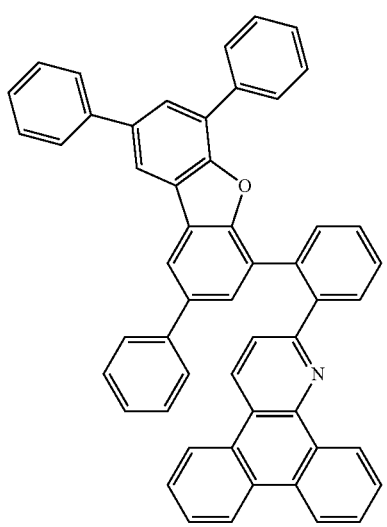
(236)
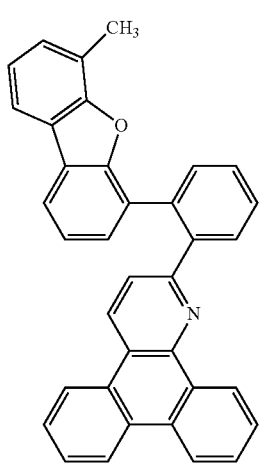
(237)
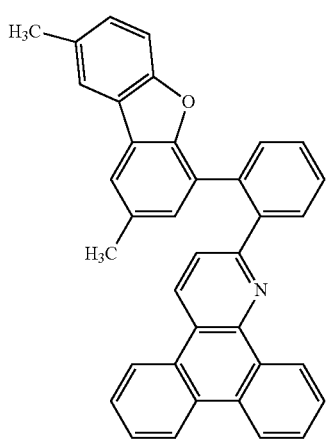
(238)
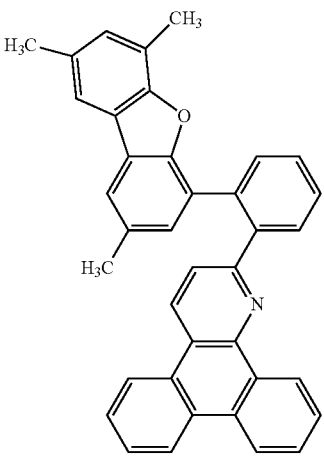
(239)
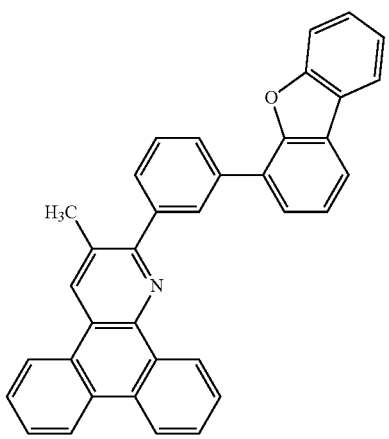
(240)
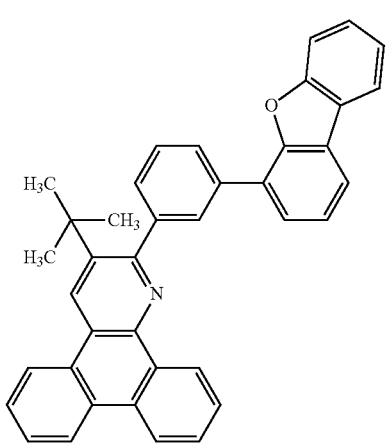

(241)
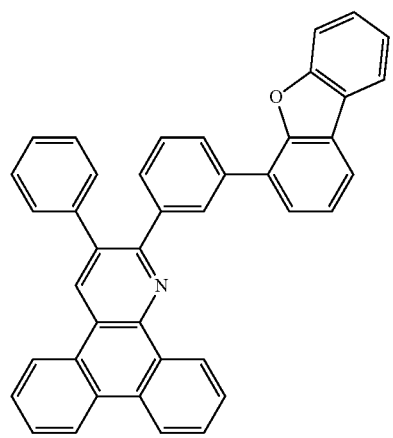
(242)
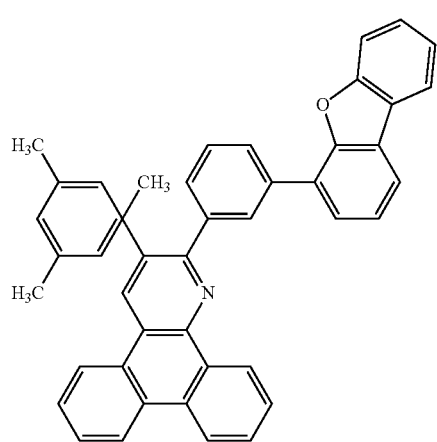
(243)
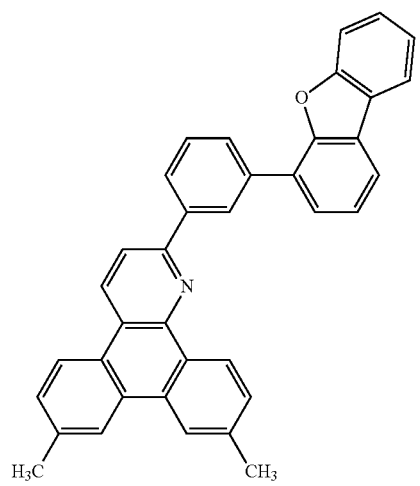
(244)
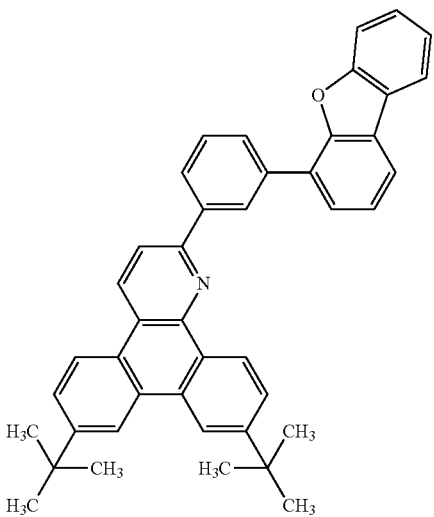
(245)
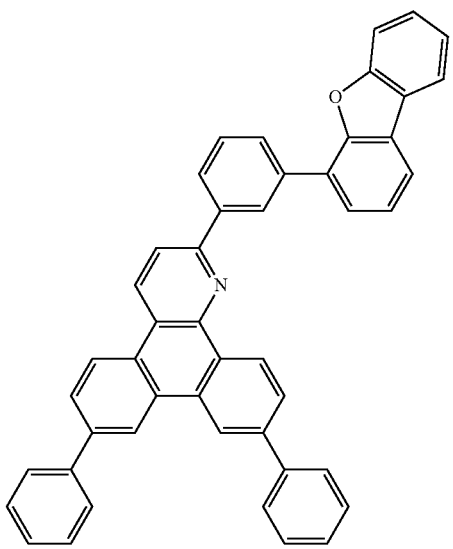
(246)
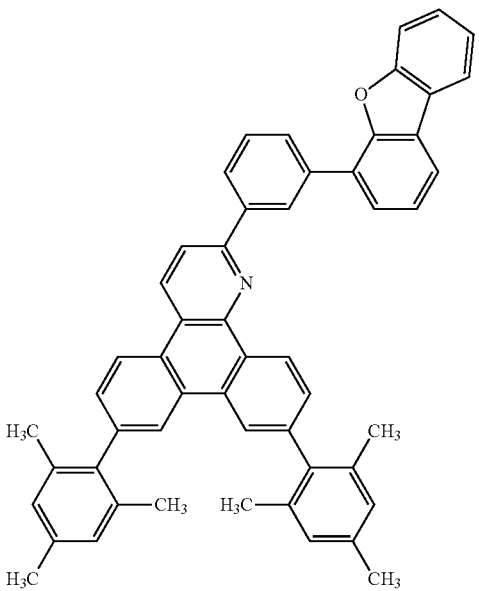

(247)
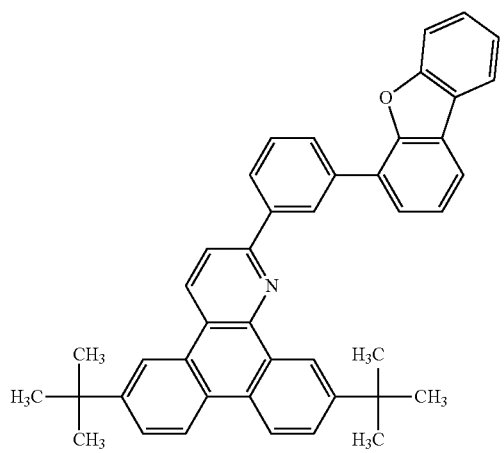
(248)
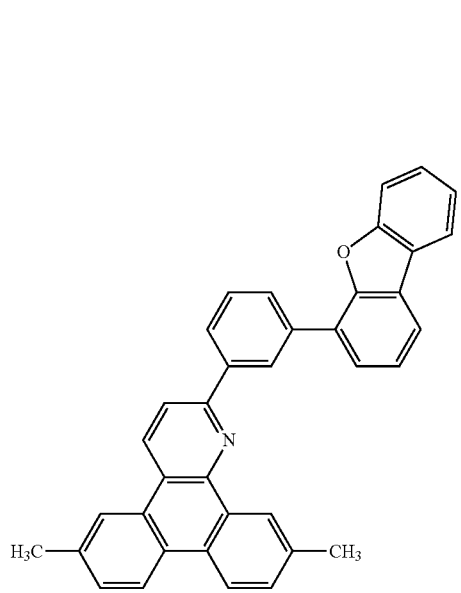
(249)
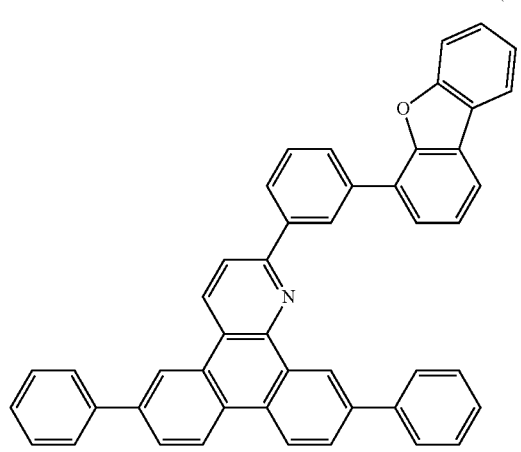
(250)
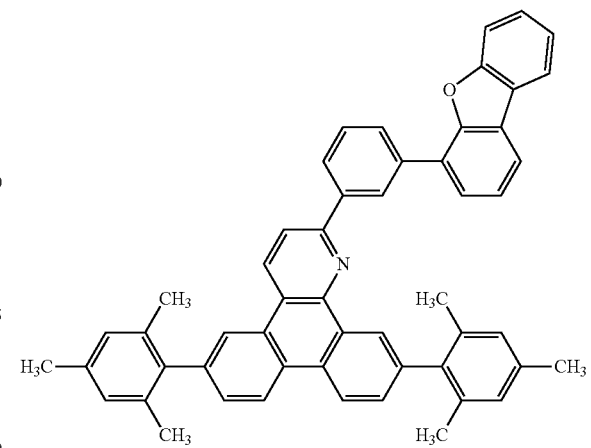
(251)
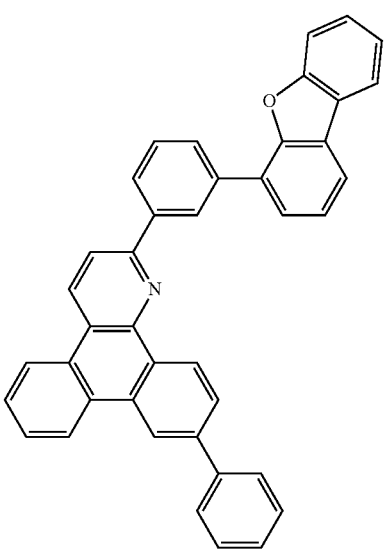
(252)

(253)
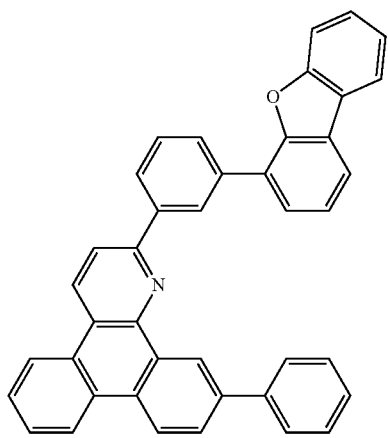
(254)
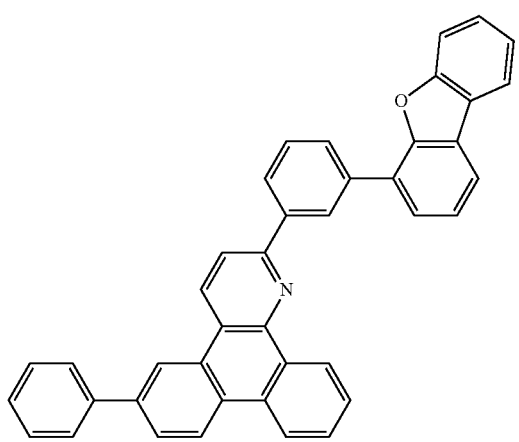
(300)
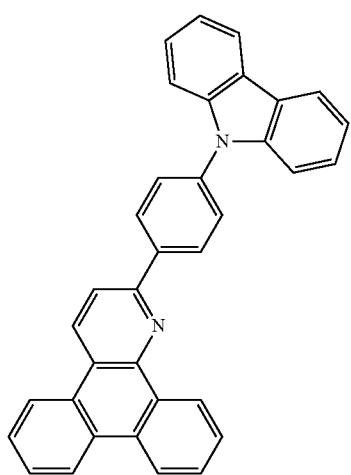
(301)
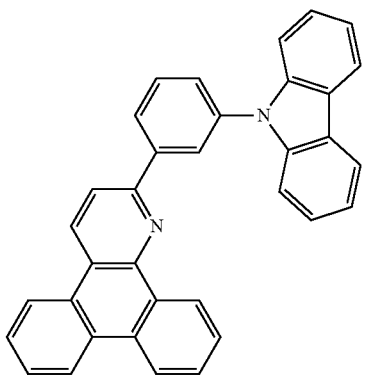
(302)
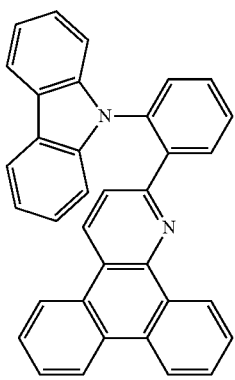
(303)
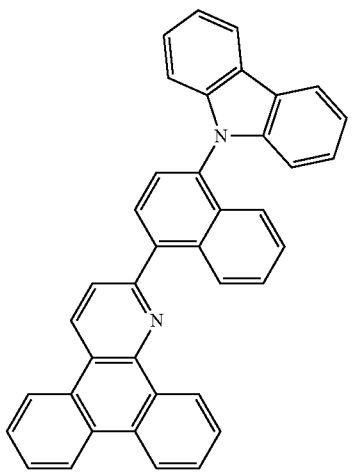

(304)
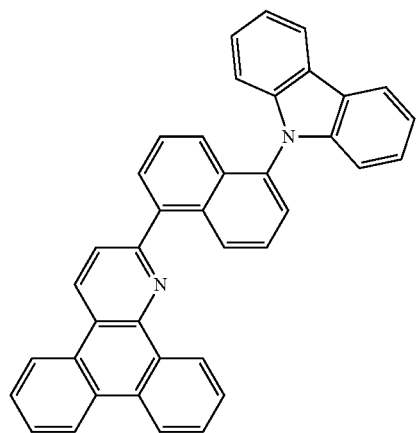
(305)
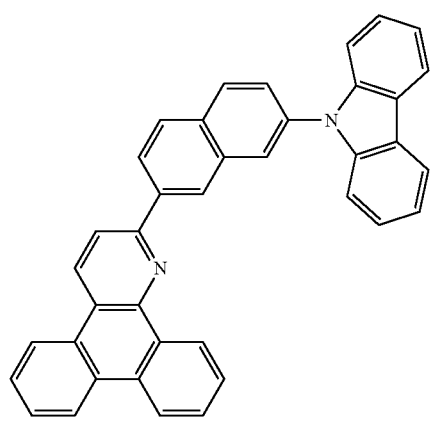
(306)
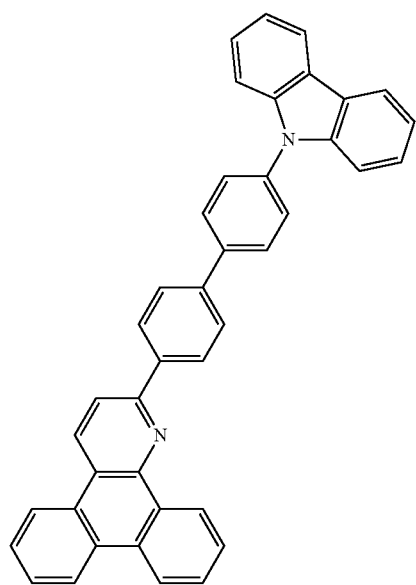
(307)
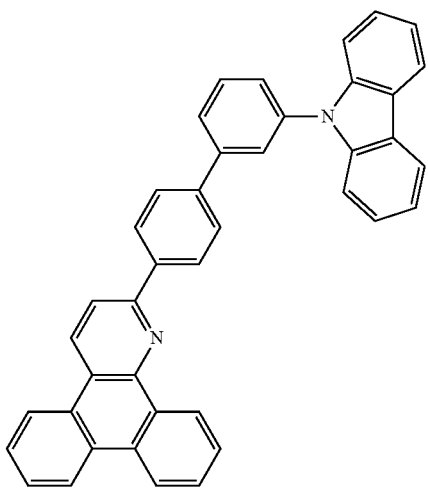
(308)
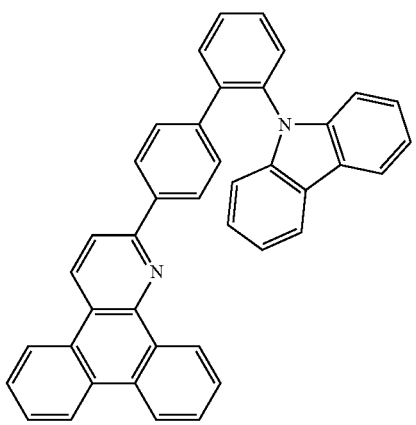
(309)
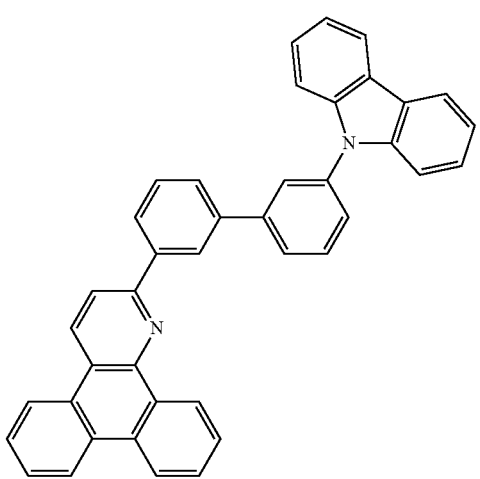

(310) 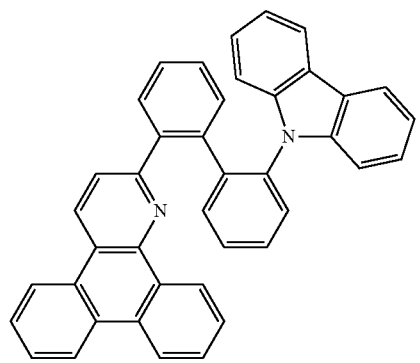
(311) 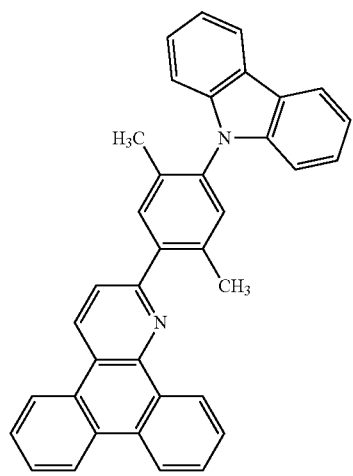
(312) 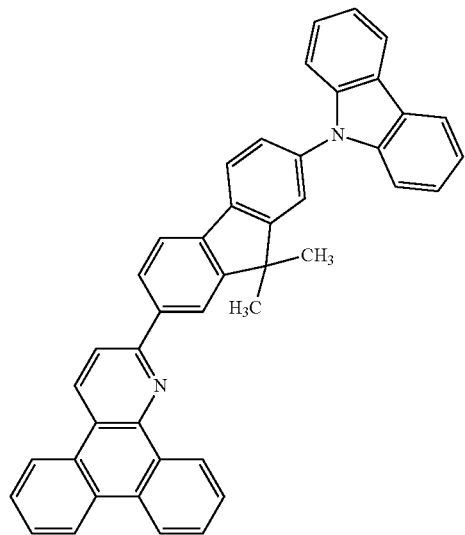
(313) 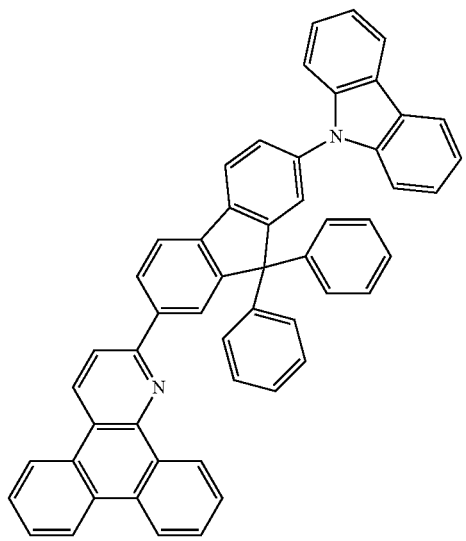
(314) 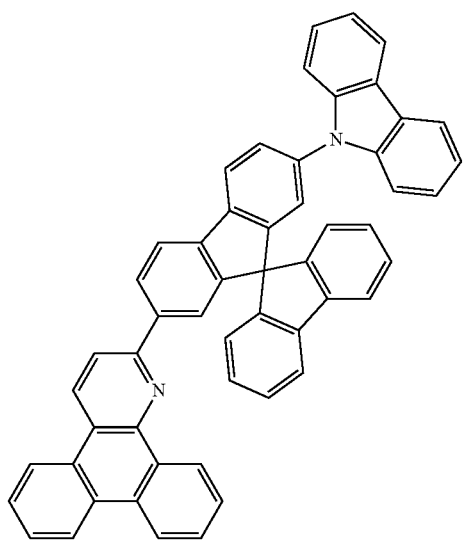
(315) 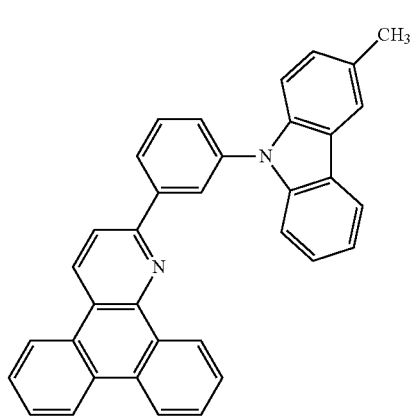

-continued
(316)
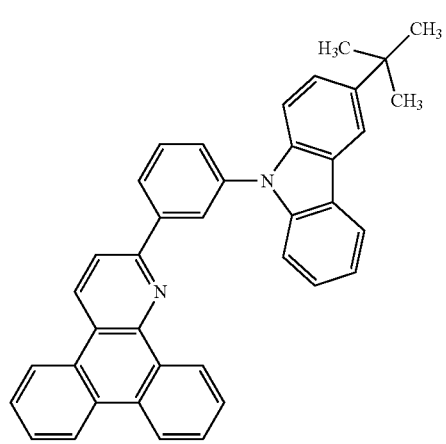
(317)
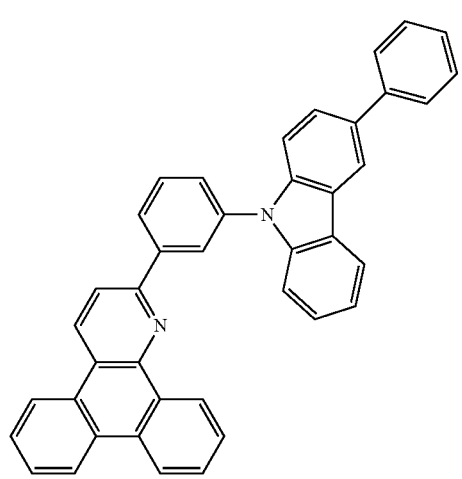
(318)
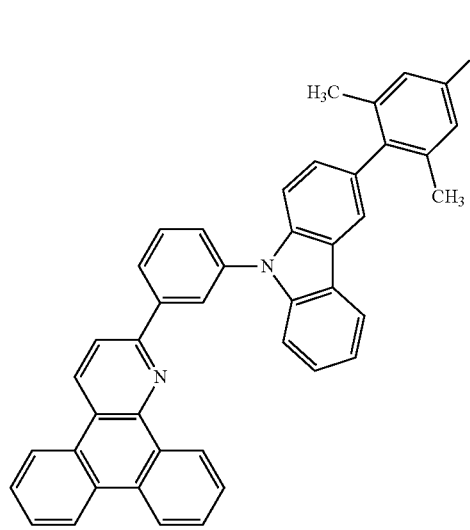
-continued
(319)
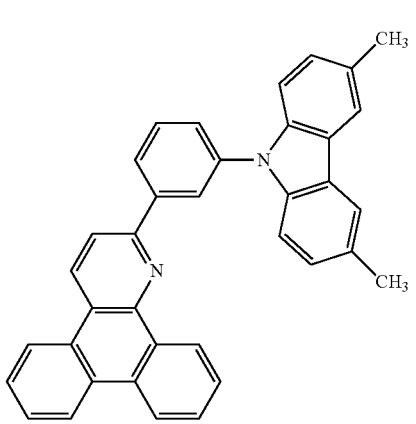
(320)
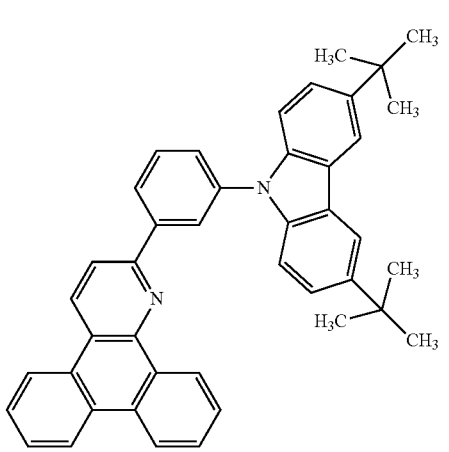
(321)
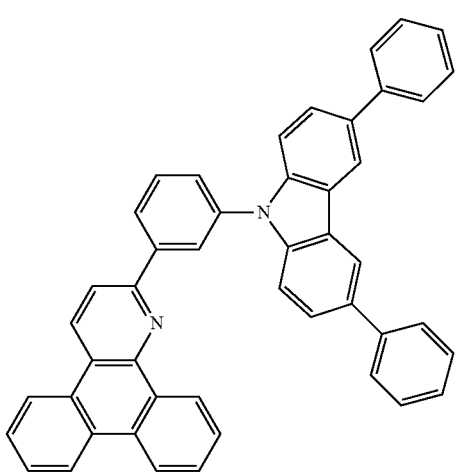

(322)
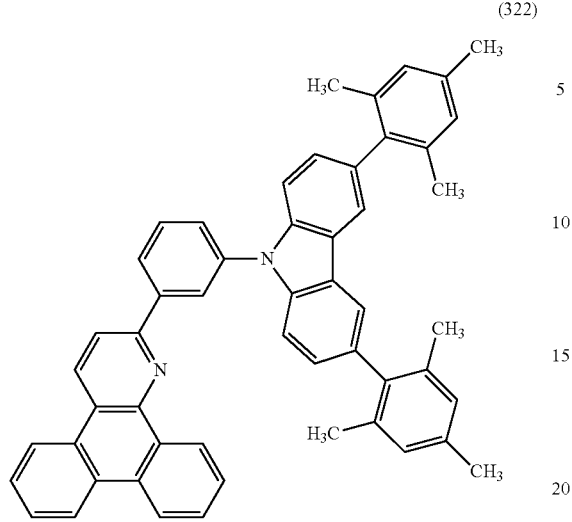
(323)
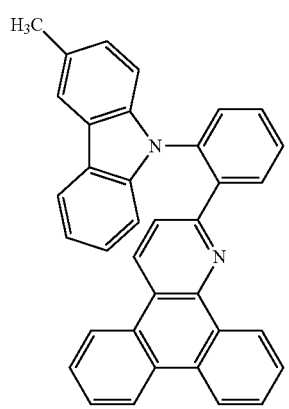
(324)
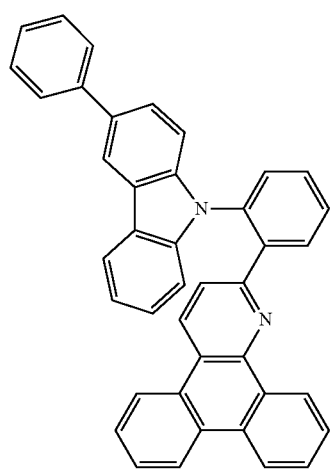
(325)
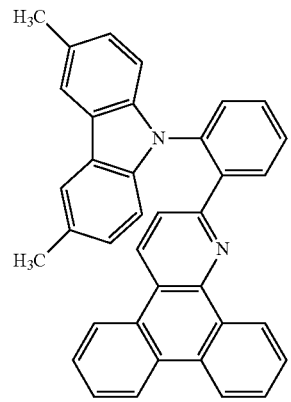
(326)
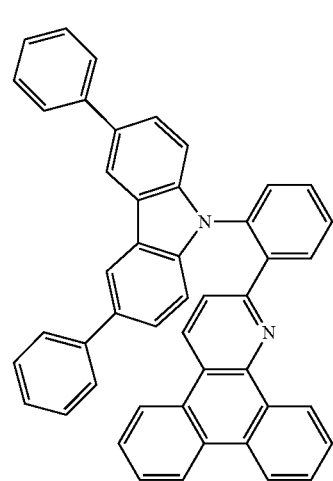
(327)
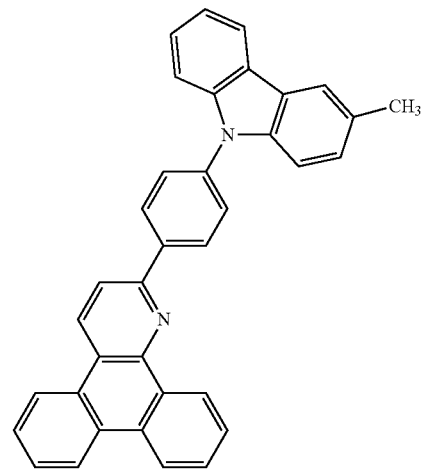

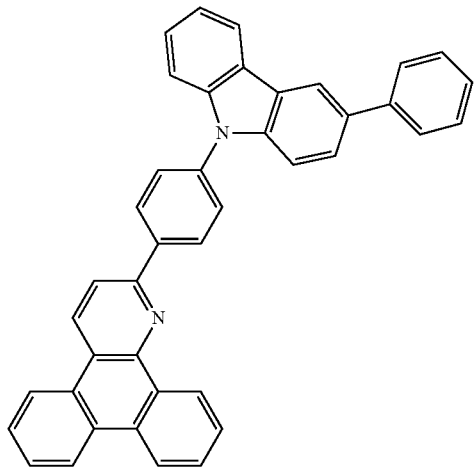
(328)
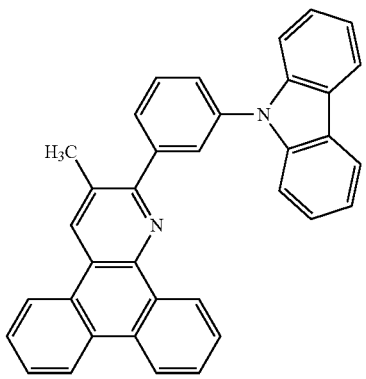
(331)
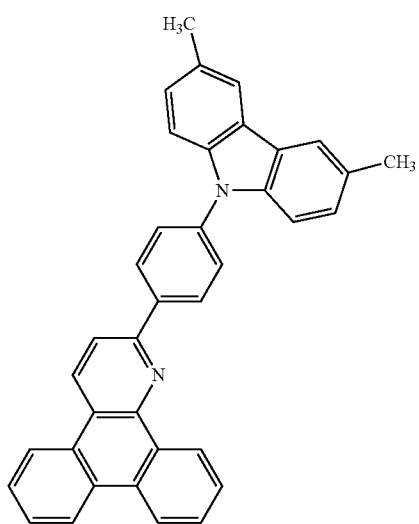
(329)
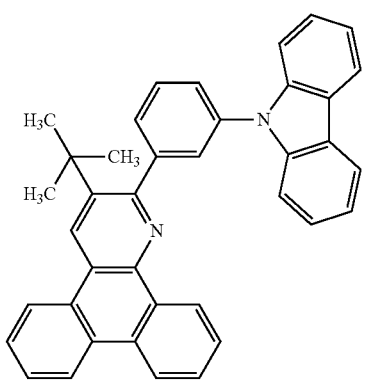
(332)
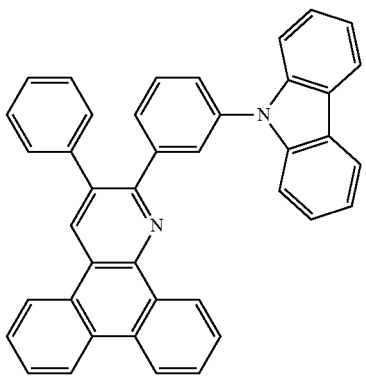
(333)
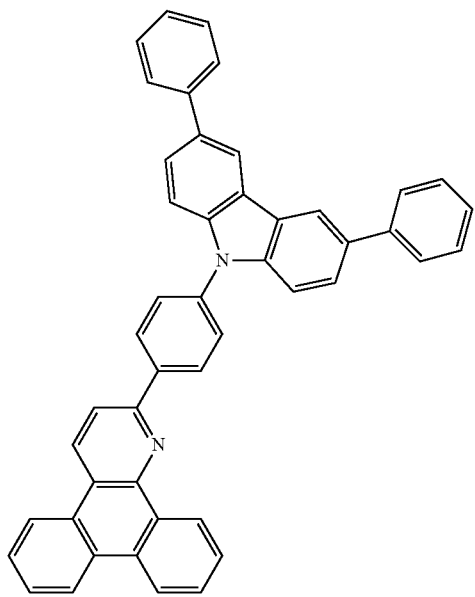
(330)
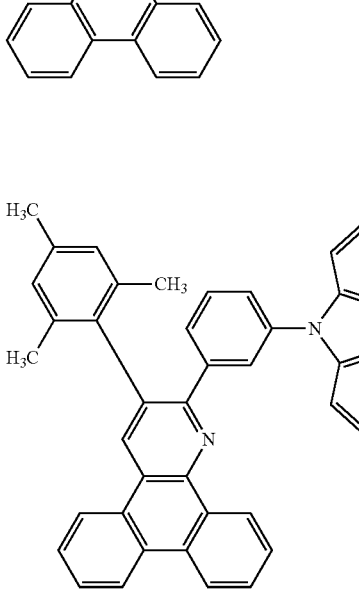
(334)

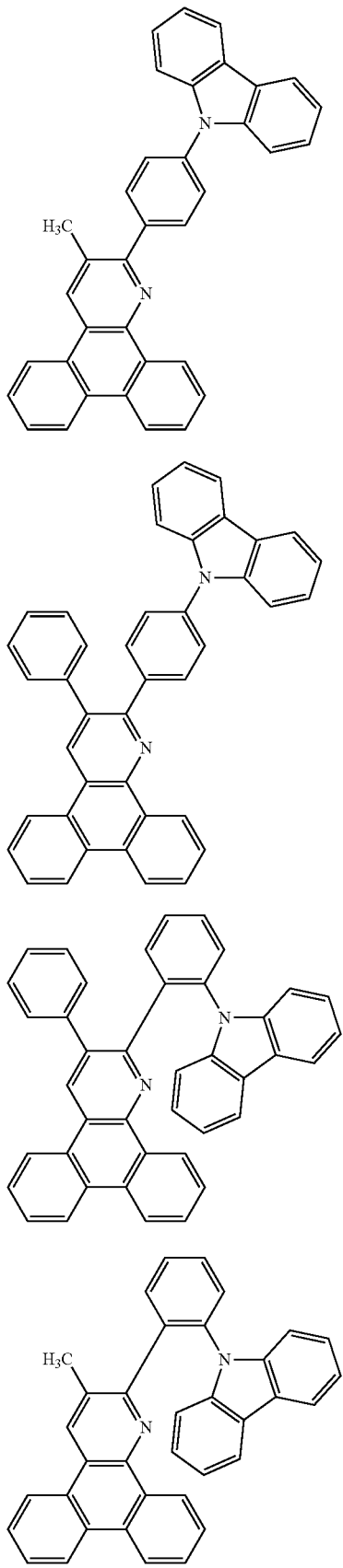
(335)
(336)
(337)
(338)
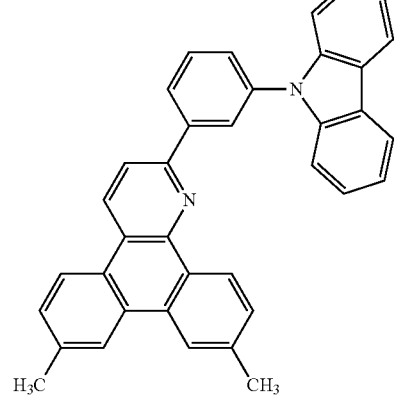
(339)
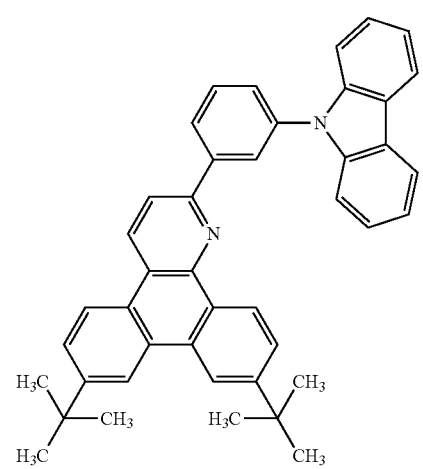
(340)
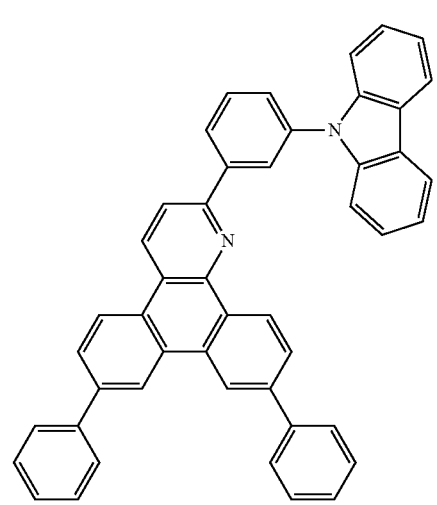
(341)

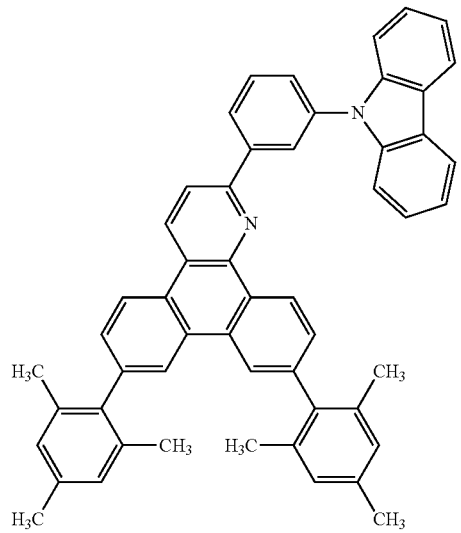
(342)
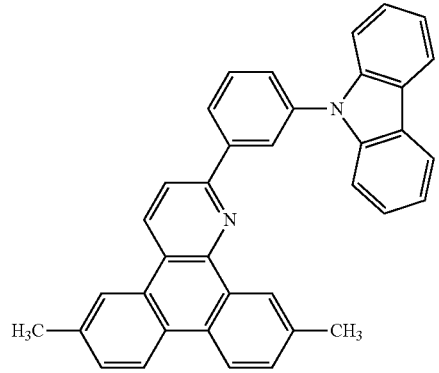
(343)
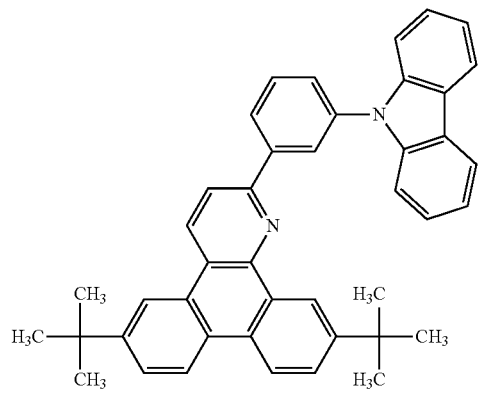
(344)
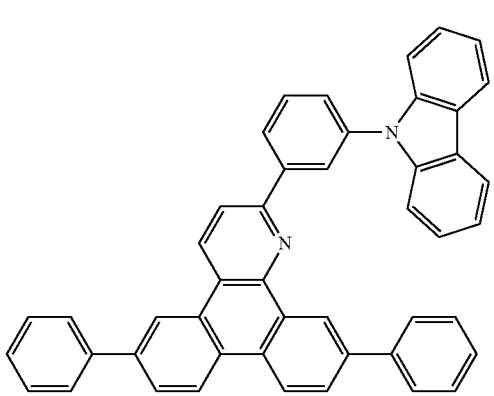
(345)
(346)
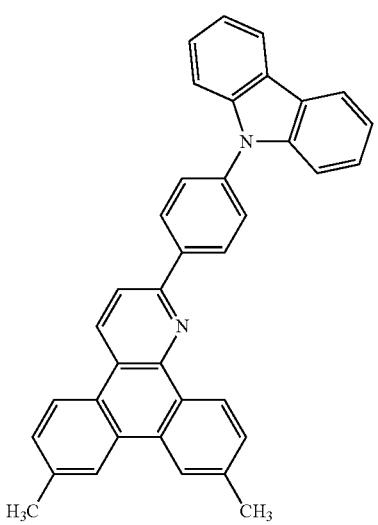
(347)

(348)
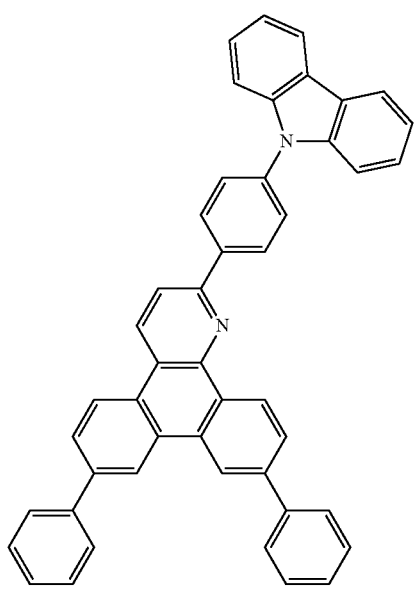
(349)
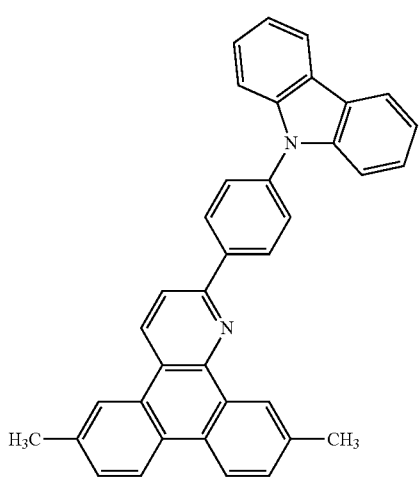
(350)
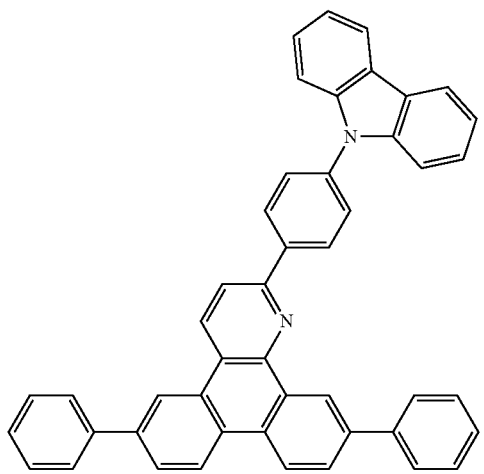
(351)
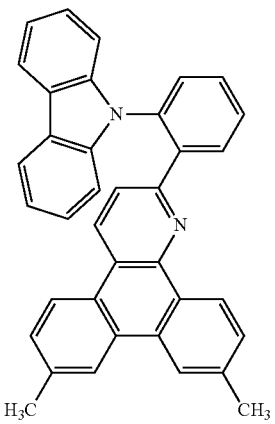
(352)
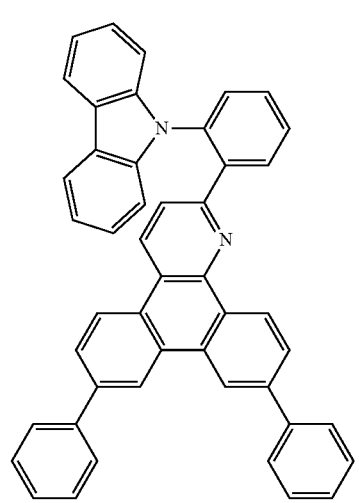
(353)
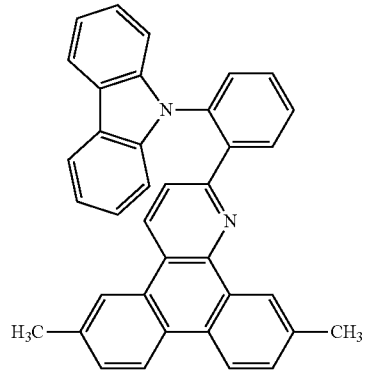

-continued (354)

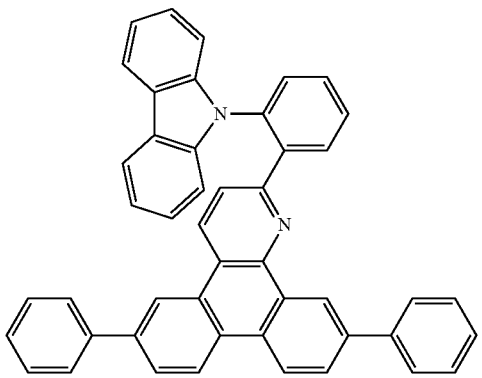

A variety of reactions can be applied to a method of synthesizing the heterocyclic compounds according to embodiments of the present invention. For example, synthesis reactions described below enable the synthesis of the heterocyclic compound according to one embodiment of the present invention represented by the general formula (G1). Note that the methods of synthesizing the heterocyclic compound according to one embodiment of the present invention are not limited to the synthesis methods below.

[Method 1 of Synthesizing a Heterocyclic Compound Represented by the General Formula (G1)]

First, a synthesis scheme (A-1) is illustrated below.

(A-1)

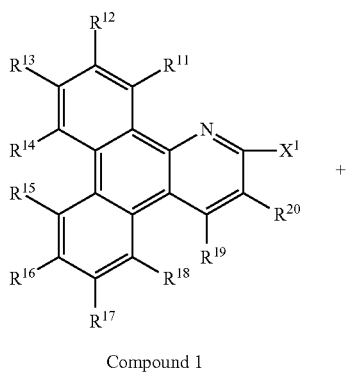

Compound 1

+

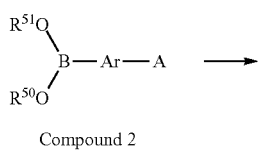

Compound 2

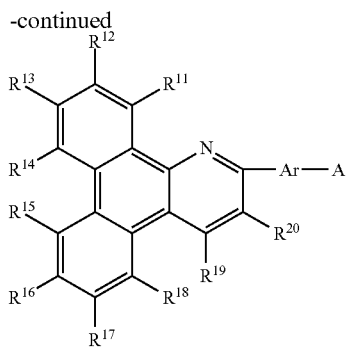

(G1)

The heterocyclic compound (G1) according to one embodiment of the present invention can be synthesized as illustrated in the synthesis scheme (A-1). Specifically, a halide of a dibenzo[f,h]quinoline derivative (Compound 1) is coupled with an organoboron compound or boronic acid of a carbazole derivative, a dibenzofuran derivative, or a dibenzothiophene derivative (Compound 2) by the Suzuki-Miyaura reaction, whereby the heterocyclic compound (G1) described in this embodiment can be obtained.

In the synthesis scheme (A-1), A represents any of a carbazolyl group, a dibenzothiophenyl group, and a dibenzofuranyl group; and $R^{11}$ to $R^{20}$ separately represent any of hydrogen, an alkyl group having 1 to 4 carbon atoms, and a substituted or unsubstituted aryl group having 6 to 13 carbon atoms. $R^{50}$ and $R^{51}$ separately represent either hydrogen or an alkyl group having 1 to 6 carbon atoms. In the synthesis scheme (A-1), $R^{50}$ and $R^{51}$ may be bonded to each other to form a ring. Further, $X^1$ represents a halogen.

Examples of a palladium catalyst that can be used in the synthesis scheme (A-1) include, but are not limited to, palladium(II) acetate, tetrakis(triphenylphosphine)palladium(0), bis(triphenylphosphine)palladium(II) dichloride, and the like.

Examples of a ligand of the palladium catalyst that can be used in the synthesis scheme (A-1) include tri(ortho-tolyl)phosphine, triphenylphosphine, tricyclohexylphosphine, and the like. Note that the ligand of the palladium catalyst that can be used is not limited to these ligands.

Examples of a base that can be used in the synthesis scheme (A-1) include, but are not limited to, an organic base such as sodium tert-butoxide, inorganic bases such as potassium carbonate and sodium carbonate, and the like.

Examples of a solvent that can be used in the synthesis scheme (A-1) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; and the like. However, the solvent that can be used is not limited to these solvents. Further, a mixed solvent of toluene and water; a mixed solvent of toluene, ethanol, and water; or a mixed solvent of an ether such as ethylene glycol dimethyl ether and water is preferable.

In the Suzuki-Miyaura reaction shown in the synthesis scheme (A-1), cross coupling using an organoaluminum compound, an organozirconium compound, an organozinc compound, an organotin compound may be used instead of using the organoboron compound or boronic acid represented by Compound 2. However, the present invention is not limited to these reactions.

Further, in the Suzuki-Miyaura reaction illustrated in the synthesis scheme (A-1), an organoboron compound or boronic acid of a dibenzo[f,h]quinoline derivative may be coupled with a halide of a carbazole derivative, a halide of a dibenzofuran derivative, a halide of a dibenzothiophene derivative, a carbazole derivative having a triflate group as a substituent, a dibenzofuran derivative having a triflate group as a substituent, or a dibenzothiophene derivative having a triflate group as a substituent, by the Suzuki-Miyaura reaction.

Thus, the heterocyclic compound of this embodiment can be synthesized.

[Method 2 of Synthesizing the Heterocyclic Compound Represented by the General Formula (G1)]

The following will show another method of synthesizing the heterocyclic compound represented by the general formula (G1). First, a synthesis scheme (B-1) in which a boron compound of A is used as a material is illustrated below.

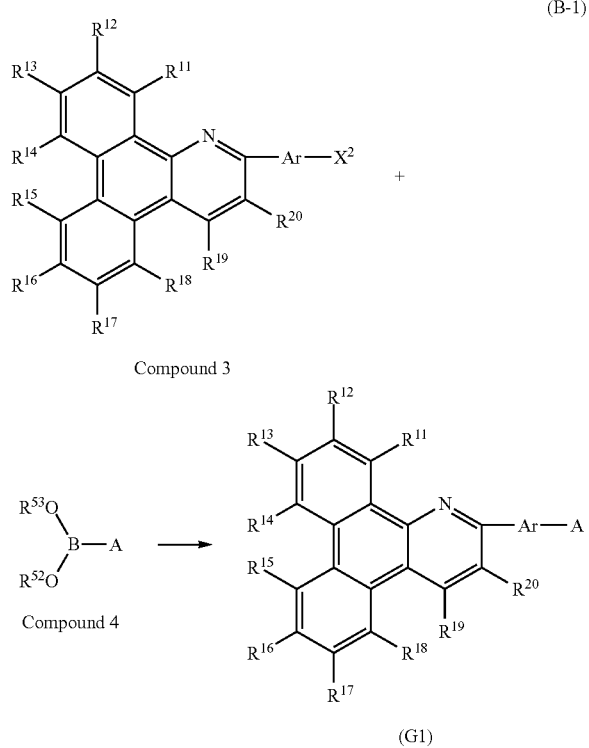

As illustrated in the synthesis scheme (B-1), a halide of a dibenzo[f,h]quinoline derivative (Compound 3) is coupled with boronic acid or an organoboron compound of a carbazole derivative, a dibenzofuran derivative, or a dibenzothiophene derivative (Compound 4) by Suzuki-Miyaura reaction, whereby the heterocyclic compound (G1) described in this embodiment can be obtained.

In the synthesis scheme (B-1), A represents any of a carbazolyl group, a dibenzothiophenyl group, and a dibenzofuranyl group; and $R^{11}$ to $R^{20}$ separately represent any of hydrogen, an alkyl group having 1 to 4 carbon atoms, and a substituted or unsubstituted aryl group having 6 to 13 carbon atoms. Ar represents an arylene group having 6 to 13 carbon atoms. The arylene group may have one or more substituents that may be bonded to form a ring. $R^{52}$ and $R^{53}$ separately represent either hydrogen or an alkyl group having 1 to 6 carbon atoms. In the synthesis scheme (B-1), $R^{52}$ and $R^{53}$ may be bonded to each other to form a ring. Further, $X^2$ represents a halogen or a triflate group, and the halogen is preferably iodine or bromine.

Examples of a palladium catalyst that can be used in the synthesis scheme (B-1) include, but are not limited to, palladium(II) acetate, tetrakis(triphenylphosphine)palladium(0), bis(triphenylphosphine)palladium(II) dichloride, and the like.

Examples of a ligand of the palladium catalyst which can be used in the synthesis scheme (B-1) include tri(ortho-tolyl)phosphine, triphenylphosphine, tricyclohexylphosphine, and the like. Note that the ligand of the palladium catalyst which can be used is not limited to these ligands.

Examples of a base that can be used in the synthesis scheme (B-1) include, but are not limited to, an organic base such as sodium tert-butoxide, inorganic bases such as potassium carbonate and sodium carbonate, and the like.

Examples of a solvent that can be used in the synthesis scheme (B-1) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; and the like. However, the solvent that can be used is not limited to these solvents. Further, a mixed solvent of toluene and water; a mixed solvent of toluene, ethanol, and water; or a mixed solvent of an ether such as ethylene glycol dimethyl ether and water is preferable.

In the Suzuki-Miyaura reaction shown in the synthesis scheme (B-1), cross coupling using an organoaluminum compound, an organozirconium compound, an organozinc compound, an organotin compound may be used instead of using the boronic acid or the organoboron compound represented by Compound 4. However, the present invention is not limited to these reactions. Further, in this coupling, a triflate group or the like may be used other than a halogen; however, the present invention is not limited thereto.

Further, in the Suzuki-Miyaura reaction illustrated in the synthesis scheme (B-1), boronic acid or an organoboron compound of a dibenzo[f,h]quinoline derivative may be coupled with a halide of a carbazole derivative, a halide of a dibenzofuran derivative, a halide of a dibenzothiophene derivative, a carbazole derivative having a triflate group as a substituent, a dibenzofuran derivative having a triflate group as a substituent, or a dibenzothiophene derivative having a triflate group as a substituent, by the Suzuki-Miyaura reaction.

In the synthesis scheme (B-1), only when A is an N-carbazolyl derivative the following synthesis scheme (B-2) allows the synthesis of a heterocyclic compound represented by the general formula (G2-2).

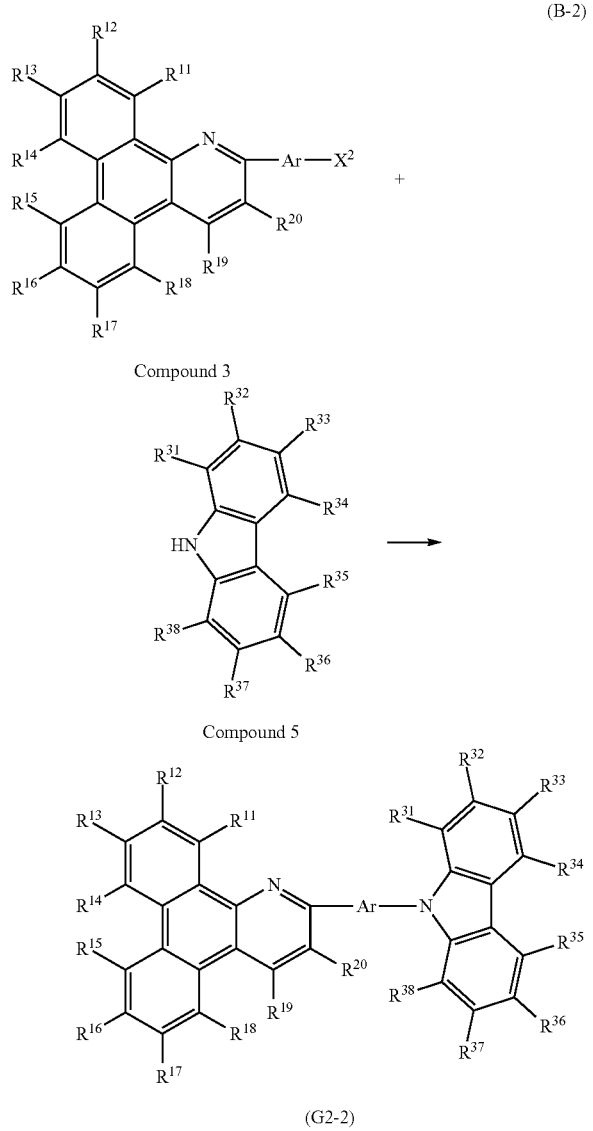

As illustrated in the synthesis scheme (B-2), the halide of a dibenzo[f,h]quinoline derivative (Compound 3) is coupled with a 9H-carbazole derivative (Compound 5) by using a metal catalyst, metal, or a metal compound in the presence of a base, whereby the heterocyclic compound (G2-2) described in this embodiment can be obtained.

In the synthesis scheme (B-2), $R^{11}$ to $R^{20}$ separately represent any of hydrogen, an alkyl group having 1 to 4 carbon atoms, and a substituted or unsubstituted aryl group having 6 to 13 carbon atoms. Ar represents an arylene group having 6 to 13 carbon atoms. The arylene group may have one or more substituents that may be bonded to form a ring. $R^{31}$ to $R^{38}$ separately represent any of hydrogen, an alkyl group having 1 to 4 carbon atoms, and a substituted or unsubstituted aryl group having 6 to 13 carbon atoms. Further, $X^3$ represents a halogen or a triflate group, and the halogen is preferably iodine or bromine.

In the case where the Hartwig-Buchwald reaction is performed in the synthesis scheme (B-2), examples of a palladium catalyst that can be used include bis(dibenzylideneacetone)palladium(0), palladium(II) acetate, and the like.

Examples of a ligand of the palladium catalyst that can be used in the synthesis scheme (B-2) include tri(tert-butyl)phosphine, tri(n-hexyl)phosphine, tricyclohexylphosphine, and the like.

Examples of a base that can be used in the synthesis scheme (B-2) include organic bases such as sodium tert-butoxide, inorganic bases such as potassium carbonate, and the like.

Examples of a solvent that can be used in the synthesis scheme (B-2) include toluene, xylene, benzene, tetrahydrofuran, and the like.

Other than the Hartwig-Buchwald reaction, the Ullmann reaction or the like may be used, and the reaction that can be used is not limited to these.

Thus, the heterocyclic compound of this embodiment can be synthesized.

Since the heterocyclic compound of this embodiment has a wide energy gap, high current efficiency can be obtained by using the heterocyclic compound as a host material for dispersing a light-emitting material in a light-emitting layer of a light-emitting element. In particular, the heterocyclic compound according to this embodiment is suitably used as a host material for dispersing a phosphorescent compound. Further, owing to a high electron-transport property, the heterocyclic compound of this embodiment can be suitably used as a material for an electron-transport layer in a light-emitting element. By using the heterocyclic compound of this embodiment, a light-emitting element that is driven at a low voltage and has high current efficiency can be achieved. Furthermore, by using this light-emitting element, a light-emitting device, an electronic device, and a lighting device each with reduced power consumption can be obtained.

Embodiment 2

In this embodiment, a light-emitting element in which the compound according to one embodiment of the present invention is used for a light-emitting layer will be described with reference to FIGS. 1A and 1B.

One embodiment of the present invention is a compound in which a dibenzo[f,h]quinoline ring and a hole-transport skeleton are bonded through an arylene group.

The above-described compound has a hole-transport skeleton in addition to a dibenzo[f,h]quinoline ring, making it easy to accept holes. Moreover, since a dibenzo[f,h]quinoline ring and a hole-transport skeleton are bonded through an arylene group, decreases in band gap and triplet excitation energy of this compound can be smaller than those of a compound in which a dibenzo[f,h]quinoline ring and a hole-transport skeleton are directly bonded. By using the compound, in which a dibenzo[f,h]quinoline ring and a hole-transport skeleton are bonded through an arylene group, for a light-emitting element, the element can have high current efficiency.

Thus, the compound described above can be suitably used as a material for an organic device such as a light-emitting element or an organic transistor.

As the hole-transport skeleton, a π-electron rich heteroaromatic ring is preferable. As the π-electron rich heteroaromatic ring, a carbazole ring, a dibenzofuran ring, or a dibenzothiophene ring is preferable. As the arylene group, any of a substituted or unsubstituted phenylene group and a substituted or unsubstituted biphenyldiyl group is preferable.

In Embodiment 2, light-emitting elements each including 2-[3-(dibenzothiophen-4-yl)phenyl]dibenzo[f,h]quinoline (abbreviation: 2mDBTPDBQu-II) represented by the structural formula (101) in Embodiment 1, which is an example of the above compounds, are described with reference to FIGS. 1A and 1B.

In the light-emitting element of this embodiment, the EL layer having at least a light-emitting layer is interposed between a pair of electrodes. The EL layer may also have a plurality of layers in addition to the light-emitting layer. The plurality of layers has a structure in which a layer containing a substance having a high carrier-injection property and a layer containing a substance having a high carrier-transport property are combined and stacked so that a light-emitting region is formed in a region away from the electrodes, that is, so that carriers recombine in a region away from the electrodes. In this specification, the layer containing a substance having a high carrier-injection or a high carrier-transport property is also called functional layer which functions, for instance, to inject or transport carriers. As the functional layer, a hole-injection layer, a hole-transport layer, an electron-injection layer, an electron-transport layer, or the like can be used.

In the light-emitting element of this embodiment illustrated in FIG. 1A, an EL layer 102 having a light-emitting layer 113 is provided between a pair of electrodes, a first electrode 101 and a second electrode 103. The EL layer 102 includes a hole-injection layer 111, a hole-transport layer 112, the light-emitting layer 113, an electron-transport layer 114, and an electron-injection layer 115. The light-emitting element in FIG. 1A includes the first electrode 101 formed over a substrate 100; the hole-injection layer 111, the hole-transport layer 112, the light-emitting layer 113, the electron-transport layer 114, and the electron-injection layer 115 which are stacked over the first electrode 101 in this order; and the second electrode 103 provided over the electron-injection layer 115. Note that, in the light-emitting element described in this embodiment, the first electrode 101 functions as an anode and the second electrode 103 functions as a cathode.

The substrate 100 is used as a support of the light-emitting element. For example, glass, quartz, plastic, or the like can be used for the substrate 100. Furthermore, a flexible substrate may be used. The flexible substrate is a substrate that can be bent (is flexible), such as a plastic substrate made of polycarbonate, polyarylate, or polyether sulfone, for example. Alternatively, a film (made of polypropylene, polyester, vinyl, polyvinyl fluoride, polyvinyl chloride, or the like), an inorganic film formed by evaporation, or the like can be used. Note that another substrate can be used as long as it can function as a support in a process of manufacturing the light-emitting element.

For the first electrode 101, a metal, an alloy, an electrically conductive compound, a mixture thereof, or the like which has a high work function (specifically, a work function of 4.0 eV or more) is preferably used. Specific examples include indium oxide-tin oxide (ITO: indium tin oxide), indium oxide-tin oxide containing silicon or silicon oxide, indium oxide-zinc oxide, indium oxide containing tungsten oxide and zinc oxide, and the like. Films of these conductive metal oxides are usually formed by sputtering; however, a sol-gel method or the like may also be used. For example, a film of indium oxide-zinc oxide can be formed by a sputtering method using a target obtained by adding 1 wt % to 20 wt % of zinc oxide to indium oxide. Further, a film of indium oxide containing tungsten oxide and zinc oxide can be formed by a sputtering method using a target obtained by addition of 0.5 wt % to 5 wt % of tungsten oxide and 0.1 wt % to 1 wt % of zinc oxide to indium oxide. Further, gold, platinum, nickel, tungsten, chromium, molybdenum, iron, cobalt, copper, palladium, nitrides of metal materials (e.g., titanium nitride), and the like can be given.

Note that, in the EL layer 102, when a layer in contact with the first electrode 101 is formed using a composite material of an organic compound and an electron acceptor (acceptor) described later, the first electrode 101 can be formed using any of a variety of metals, alloys, and electrically conductive compounds, a mixture thereof, and the like regardless of the work function. For example, aluminum (Al), silver (Ag), an alloy containing aluminum (e.g., Al—Si), or the like can be used.

The EL layer 102 formed over the first electrode 101 includes at least the light-emitting layer 113, and part of the EL layer 102 is formed using the heterocyclic compound according to one embodiment of the present invention. For the part of the EL layer 102, a known substance can be used, and either a low molecular compound or a high molecular compound can be used. Note that the substance used for forming the EL layer 102 may have not only a structure formed of only an organic compound but also a structure in which an inorganic compound is partially contained.

As illustrated in FIG. 1A, the EL layer 102 is formed by stacking as appropriate the hole-injection layer 111, the hole-transport layer 112, the electron-transport layer 114, the electron-injection layer 115, and the like in combination as well as the light-emitting layer 113.

The hole-injection layer 111 is a layer containing a substance with a high hole-injection property. As the substance with a high hole-injection property, for example, metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide can be used. A phthalocyanine-based compound such as phthalocyanine (abbreviation: $H_2Pc$), or copper(II) phthalocyanine (abbreviation: CuPc) can also be used.

Alternatively, any of the following aromatic amine compounds which are low molecular organic compounds can be used: 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Further alternatively, any of high molecular compounds (e.g., oligomers, dendrimers, or polymers) can be used. For example, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), or poly[N,N'-bis(4-butylphenyl)-N,N'-bis(phenyl)benzidine (abbreviation: poly-TPD) can be given. Further, a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS), can be used.

A composite material in which an organic compound and an electron acceptor (acceptor) are mixed may be used for the hole-injection layer 111. Such a composite material has excellent hole-injection and hole-transport properties because holes are generated in the organic compound by the electron acceptor. In this case, the organic compound is preferably a material excellent in transporting the generated holes (substance having a high hole-transport property).

As the organic compound for the composite material, various compounds such as an aromatic amine compound, carbazole derivatives, aromatic hydrocarbon, and a high molecular compound (such as oligomer, dendrimer, or polymer) can be used. The organic compound used for the composite material is preferably an organic compound having a high hole-transport property. Specifically, a substance having a hole mobility of $10^{-6}$ cm$^2$/V·s or higher is preferably used. However, other substances than the above described materials may also be used as long as the substances have higher hole-transport properties than electron-transport properties. The organic compounds which can be used for the composite material will be specifically shown below.

Examples of the organic compounds that can be used for the composite material include aromatic amine compounds such as TDATA, MTDATA, DPAB, DNTPD, DPA3B, PCzPCA1, PCzPCA2, PCzPCN1,4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl]-2,3,5,6-tetraphenylbenzene.

Alternatively, it is possible to use any of the following aromatic hydrocarbon compounds: 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl) anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, 2,3,6,7-tetramethyl-9,10-di(1-naphthyl) anthracene, and the like.

Further alternatively, it is possible to use any of the following aromatic hydrocarbon compounds: 2,3,6,7-tetramethyl-9,10-di(2-naphthyl) anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Further, as the electron acceptor, organic compounds such as 7,7,8,8-tetracyano-2,3,5,6-tetrafluoroquinodimethane (abbreviation: F$_4$TCNQ) and chloranil; and transition metal oxides can be given. In addition, oxides of metals belonging to Groups 4 to 8 in the periodic table can also be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable because it is stable in the air, has a low hygroscopic property, and is easily handled.

Note that the hole-injection layer 111 may be formed using a composite material of the above-described high molecular compound, such as PVK, PVTPA, PTPDMA, or Poly-TPD, and the above-described electron acceptor.

The hole-transport layer 112 is a layer containing a substance with a high hole-transport property. As the substance having a high hole-transport property, it is possible to use, for example, any of the following aromatic amine compounds: NPB, TPD, BPAFLP, 4,4'-bis[N-(9,9-dimethylfluoren-2-yl)-N-phenylamino]biphenyl (abbreviation: DFLDPBi), 4,4'-bis[N-(spiro-9,9'-bifluoren-2-yl)-N-phenylamino]biphenyl (abbreviation: BSPB), and the like. The substances mentioned here are mainly ones that have a hole mobility of $10^{-6}$ cm$^2$/V·s or higher. However, other substances than the above described materials may also be used as long as the substances have higher hole-transport properties than electron-transport properties. The layer containing a substance with a high hole-transport property is not limited to a single layer, and two or more layers containing the aforementioned substances may be stacked.

For the hole-transport layer 112, a carbazole derivative, such as CBP, CzPA, or PCzPA, or an anthracene derivative, such as t-BuDNA, DNA, or DPAnth, may be used.

For the hole-transport layer 112, a high molecular compound such as PVK, PVTPA, PTPDMA, or Poly-TPD can also be used.

The light-emitting layer 113 is a layer containing a light-emitting material. This embodiment will show a case where 2-[3-(dibenzothiophen-4-yl)phenyl]dibenzo[f,h]quinoline (abbreviation: 2mDBTPDBQu-II) described in Embodiment 1 is used for the light-emitting layer. For the light-emitting layer in which a light-emitting material (guest material) is dispersed in another material (host material), 2mDBTPDBQu-II (abbreviation) can be used as the host material. The guest material which is a light-emitting material is dispersed in 2mDBTPDBQu-II (abbreviation), whereby light emission can be obtained from the guest material. Thus, a compound according to one embodiment of the present invention, in which a dibenzo[f,h]quinoline ring and a hole-transport skeleton are bonded through an arylene group, is effective in its use as a host material in a light-emitting layer.

In addition, plural kinds of substances (host materials) in which the light-emitting material (guest material) is dispersed can be used. The light-emitting layer may thus include a second host material in addition to 2mDBTPDBQu-II (abbreviation).

As a light-emitting material, for example, a fluorescent compound which emits fluorescence or a phosphorescent compound which emits phosphorescence can be used. Examples of a material for blue light emission, which can be used for the light-emitting layer 113, include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl) triphenylamine (abbreviation: PCBAPA), and the like. Examples of a material for green light emission include N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis (1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Examples of a material for yellow light emission include rubrene, 5,12-bis(1,1'-biphenyl-4-yl)-6,11-diphenyltetracene (abbreviation: BPT), and the like. Examples of a material for red light emission include N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), and the like.

Further, examples of phosphorescent compounds that can be used for the light-emitting layer 113 are described. Examples of a material for green light emission include tris(2-phenylpyridinato-N,C$^{2'}$)iridium(III) (abbreviation: Ir(ppy)$_3$), bis(2-phenylpyridinato-N, C$^{2'}$)iridium(III)acetylacetonate (abbreviation: Ir(ppy)$_2$(acac)), bis(1,2-diphenyl-1H-benzimidazolato)iridium(III)acetylacetonate (abbreviation: Ir(pbi)$_2$(acac)), bis(benzo[h]quinolinato)iridium(III)acetylacetonate (abbreviation: Ir(bzq)$_2$(acac)), tris(benzo[h]quinolinato)iridium(III) (abbreviation: [Ir(bzq)$_3$]), and the like. Examples of a material for yellow light emission include bis(2,4-diphenyl-1,3-oxazolato-N,C$^{2'}$)iridium(III)acetylacetonate (abbreviation: Ir(dpo)$_2$(acac)), bis[2-(4'-(perfluorophenylphenyl)pyridinato]iridium(III)acetylacetonate (abbreviation: Ir(p-PF-ph)$_2$(acac)), bis(2-phenylbenzothiazolato-N,C$^{2'}$)iridium(III)acetylacetonate (abbreviation: Ir(bt)$_2$(acac)), (acetylacetonato)bis[2,3-bis(4-fluorophenyl)-5-methylpyrazinato]iridium(III) (abbreviation: Ir(Fdppr-Me)$_2$(acac)), (acetylacetonato)bis{2-(4-methoxyphenyl)-3,5-dimethylpyrazinato}iridium(III) (abbreviation: Ir(dmmoppr)$_2$(acac)), and the like. Examples of a material for orange light emission include tris(2-phenylquinolinato-N,C$^{2'}$)iridium(III) (abbreviation: Ir(pq)$_3$), bis(2-phenylquinolinato-N,C$^{2'}$)iridium(III)acetylacetonate (abbreviation: Ir(pq)$_2$(acac)), (acetylacetonato)bis(3,5-dimethyl-2-phenylpyrazinato)iridium(III) (abbreviation: Ir(mppr-Me)$_2$(acac)), (acetylacetonato)bis(5-isopropyl-3-methyl-2-phenylpyrazinato)iridium(III) (abbreviation: Ir(mppr-iPr)$_2$(acac)), and the like. Examples of a material for red light emission include the following organometallic complexes: bis[2-(2'-benzo[4,5-a]thienyl)pyridinato-N,C$^{3'}$)iridium(III)acetylacetonate (abbreviation: Ir(btp)$_2$(acac)), bis(1-phenylisoquinolinato-N, C$^{2'}$)iridium(III)acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), bis(2,3,5-triphenylpyrazinato)(dipivaloylmethanato)iridium(III) (abbreviation: Ir(tppr)$_2$(dpm)), 2,3,7,8,12,13,17,18-octaethyl-21H,23H-porphyrin platinum(II) (abbreviation: PtOEP), and the like. In addition, a rare earth metal complex such as tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), or tris[1-(2-thenoyl)-3,3,3-trifluoroacetonato](monophenanthroline)europium(III) (abbreviation: Eu(TTA)$_3$(Phen)) exhibits light emission from a rare earth metal ion (electron transition between different multiplicities); therefore, such a rare earth metal complex can be used as a phosphorescent compound.

As the light-emitting material, a high molecular compound can also be used. Specifically, as a light-emitting material which emits blue light, any of the following can be used: poly(9,9-dioctylfluorene-2,7-diyl) (abbreviation: PFO), poly[(9,9-dioctylfluorene-2,7-diyl-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]} (abbreviation: TAB-PFH), and the like. As a light-emitting material that emits green light, any of the following can be used: poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), poly[(9,9-dioctyl-2,7-divinylenfluorenylene)-alt-co-(2-methoxy-5-(2-ethylhexyloxy)-1,4-phenylene)], and the like. As a light-emitting material that emits orange to red light, any of the following can be used: poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-d]hexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD), and the like.

The electron-transport layer 114 is a layer containing a substance with a high electron-transport property. Examples of the substance with a high electron-transport property include a metal complex having a quinoline skeleton or a benzoquinoline skeleton such as tris(8-quinolinolato)aluminum (abbreviation: Alq), tris(4-methyl-8-quinolinolato)aluminum (abbreviation: Almq$_3$), bis(10-hydroxybenzo[h]-quinolinato)beryllium (abbreviation: BeBq$_2$), bis(2-methyl-8-quinolinolato)(4-phenylphenolato)aluminum (abbreviation: BAlq), and the like. Alternatively, it is possible to use a metal complex or the like including an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$). Besides the metal complexes, it is also possible to use 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like. The substances mentioned here are mainly ones that have an electron mobility of $10^{-6}$ cm$^2$/V·s or higher. Furthermore, the electron-transport layer is not limited to a single layer, and two or more layers containing the aforementioned substances may be stacked.

The electron-injection layer 115 is a layer containing a substance with a high electron-injection property. The electron-injection layer 115 can be formed using an alkali metal, an alkaline earth metal, or a compound thereof, such as lithium, cesium, calcium, lithium fluoride, cesium fluoride, calcium fluoride, or lithium oxide. A rare earth metal compound such as erbium fluoride can also be used. Alternatively, the above-mentioned substances for forming the electron-transport layer 114 can be used.

Alternatively, a composite material in which an organic compound and an electron donor (donor) are mixed may be used for the electron-injection layer 115. Such a composite material has excellent electron-injection and electron-transport properties because electrons are generated in the organic compound by the electron donor. The organic compound here is preferably a material excellent in transporting the generated electrons. Specifically, for example, the substances for forming the electron-transport layer 114 (e.g., a metal complex and a heteroaromatic compound), which are described above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like can be given. Further, an alkali metal oxide or an alkaline-earth metal oxide is preferable, and there are, for example, lithium oxide, calcium oxide, barium oxide, and the like. Alternatively, a Lewis base such as magnesium oxide can also be used. Further alternatively, an organic compound such as tetrathiafulvalene (abbreviation: TTF) can be used.

Note that each of the above-described hole-injection layer 111, hole-transport layer 112, light-emitting layer 113, electron-transport layer 114, and electron-injection layer 115 can be formed by a method such as an evaporation method (e.g., a vacuum evaporation method), an inkjet method, or a coating method.

When the second electrode 103 functions as a cathode, it can be formed using a metal, an alloy, an electrically conductive compound, a mixture thereof, or the like having a low work function (preferably, a work function of 3.8 eV or less). Specifically, any of the following can be used: aluminum or silver; an element belonging to Group 1 or Group 2 of the periodic table, that is, an alkali metal such as lithium or cesium, an alkaline earth metal such as calcium or strontium, or magnesium; an alloy of the above metals (e.g., Mg—Ag or Al—Li); a rare earth metal such as europium or ytterbium; an alloy of the above metals; or the like.

Note that, in the case where in the EL layer 102, a layer formed in contact with the second electrode 103 is formed using a composite material in which the organic compound and the electron donor (donor), which are described above, are mixed, a variety of conductive materials such as aluminum, silver, ITO, and indium tin oxide containing silicon or silicon oxide can be used regardless of the work function.

Note that the second electrode 103 can be formed by a vacuum evaporation method or a sputtering method. Alternatively, in the case of using a silver paste or the like, a coating method, an inkjet method, or the like can be used.

In the above-described light-emitting element, current flows due to a potential difference generated between the first electrode 101 and the second electrode 103 and holes and electrons recombine in the EL layer 102, whereby light is emitted. Then, this emitted light is extracted out through one or both of the first electrode 101 and the second electrode 103. Therefore, one of or both the first electrode 101 and the second electrode 103 is/are an electrode(s) having a property of transmitting visible light.

Further, a structure of a layer provided between the first electrode 101 and the second electrode 103 is not limited to the above described structure. A structure other than the above may alternatively be employed as long as a light-emitting region in which holes and electrons recombine is provided in a portion away from the first electrode 101 and the second electrode 103 in order to prevent quenching due to proximity of the light-emitting region to a metal.

In other words, there is no particular limitation on a stack structure of the layers. A layer containing a substance with a high electron-transport property, a substance with a high hole-transport property, a substance with a high electron-injection property, a substance with a high hole-injection property, a bipolar substance (substance having a high electron-transport property and a high hole-transport property), a hole-blocking material, or the like may freely be combined with a light-emitting layer containing 2mDBTPDBQu-II (abbreviation) as a host material.

Since 2mDBTPDBQu-II (abbreviation) is a substance with a high electron-transport property, 2mDBTPDBQu-II (abbreviation) can also be used for the electron-transport layer. In other words, a compound according to one embodiment of the present invention, in which a dibenzo[f,h]quinoline ring and a hole-transport skeleton are bonded through an arylene group, can be used for the electron-transport layer.

Furthermore, by using a compound according to one embodiment of the present invention, in which a dibenzo[f,h]quinoline ring and a hole-transport skeleton are bonded through an arylene group, for both the light-emitting layer (especially as a host material in the light-emitting layer) and the electron-transport layer, extremely low-voltage driving can be achieved.

Figure 1B:
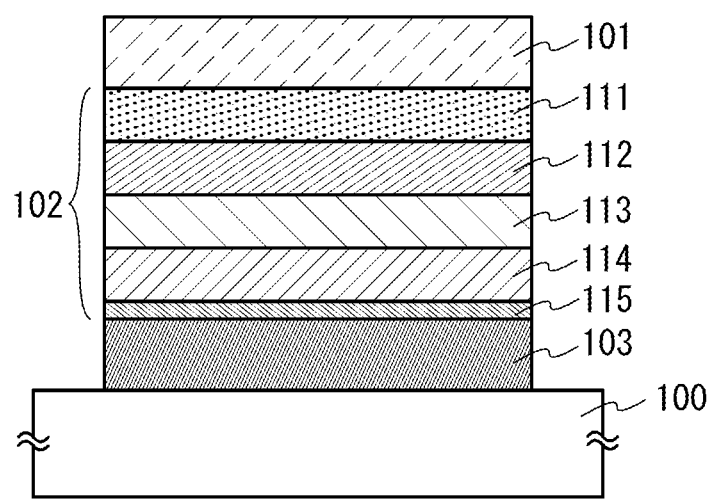

In a light-emitting element illustrated in FIG. 1B, the EL layer 102 is provided between the first electrode 101 and the second electrode 103 over the substrate 100. The EL layer 102 includes the hole-injection layer 111, the hole-transport layer 112, the light-emitting layer 113, the electron-transport layer 114, and the electron-injection layer 115. The light-emitting element in FIG. 1B includes the second electrode 103 serving as a cathode over the substrate 100; the electron-injection layer 115, the electron-transport layer 114, the light-emitting layer 113, the hole-transport layer 112, and the hole-injection layer 111 which are stacked over the second electrode 103 in this order; and the first electrode 101 serving as an anode over the hole-injection layer 111.

The following will show a specific method of forming a light emitting element.

The light-emitting element of Embodiment 2 has a structure in which an EL layer is interposed between a pair of electrodes. The EL layer has at least the light-emitting layer, and the light-emitting layer is formed using 2mDBTPDBQu-II (abbreviation) as a host material. Further, the EL layer may include a functional layer (e.g., a hole-injection layer, a hole-transport layer, an electron-transport layer, or an electron-injection layer) in addition to the light-emitting layer. The electrodes (the first electrode and the second electrode), the light-emitting layer, and each functional layer may be formed by any of wet processes such as a droplet discharging method (inkjet method), a spin coating method, and a printing method, or by a dry process such as a vacuum evaporation method, a CVD method, or a sputtering method. The use of a wet process enables the formation at atmospheric pressure using a simple device and process, thereby having the effects of simplifying the process and improving the productivity. In contrast, in a dry process, dissolution of a material is not needed, and thus, a material that has low solubility in a solution can be used to expand the range of material choices.

All the thin films included in the light-emitting element may be formed by a wet method. In this case, the light-emitting element can be manufactured with only facilities needed for a wet process. Alternatively, formation of the stacked layers up to formation of the light-emitting layer may be performed by a wet process whereas the functional layer, the first electrode, and the like which are stacked over the light-emitting layer may be formed by a dry process. Further alternatively, the second electrode and the functional layer may be formed by a dry process before the formation of the light-emitting layer whereas the light-emitting layer, the functional layer stacked thereover, and the first electrode may be formed by a wet process. Needless to say, this embodiment is not limited to this, and the light-emitting element can be formed by appropriate selection from a wet method and a dry method depending on a material to be used, necessary film thickness, and the interface state.

In this embodiment, the light-emitting element is formed over a substrate made of glass, plastic, or the like. A plurality of such light-emitting elements is formed over one substrate, thereby forming a passive matrix light-emitting device. In addition, for example, a thin film transistor (TFT) may be formed over a substrate formed of glass, plastic, or the like, and a light-emitting element may be manufactured over an electrode electrically connected to the TFT. In this manner, an active matrix light-emitting device in which the TFT controls the drive of the light-emitting element can be manufactured. Note that there is no particular limitation on the structure of the TFT. Either a staggered TFT or an inverted staggered TFT may be employed. In addition, the crystallinity of a semiconductor used for the TFT is not particularly limited either; an amorphous semiconductor or a crystalline semiconductor may be used. In addition, a driver circuit formed over a TFT substrate may be constructed from both n-channel and p-channel TFTs or from one of n-channel and p-channel TFTs.

Thus, a light-emitting element can be formed using 2mDBTPDBQu-II (abbreviation) described in Embodiment 1. By using a compound according to one embodiment of the present invention, in which a dibenzo[f,h]quinoline ring and a hole-transport skeleton are bonded through an arylene group, for a light-emitting element, the light-emitting element that is driven at a low voltage and has high current efficiency can be achieved.

Furthermore, a light-emitting device (such as an image display device) using this light-emitting element according to one embodiment of the present invention which is obtained as above can have low power consumption.

Note that by using the light-emitting element described in this embodiment, a passive matrix light-emitting device or an active matrix light-emitting device in which the driving of the light-emitting element is controlled by a thin film transistor (TFT) can be manufactured.

This embodiment can be implemented in appropriate combination with the other embodiments and examples below.

Embodiment 3

In this embodiment, a mode of a light-emitting element having a structure in which a plurality of light-emitting units is stacked (hereinafter, referred to as tandem element or stacked-type element) will be described with reference to FIGS. 2A and 2B. This light-emitting element is a light-emitting element including a plurality of light-emitting units between a first electrode and a second electrode.

Figure 2A:
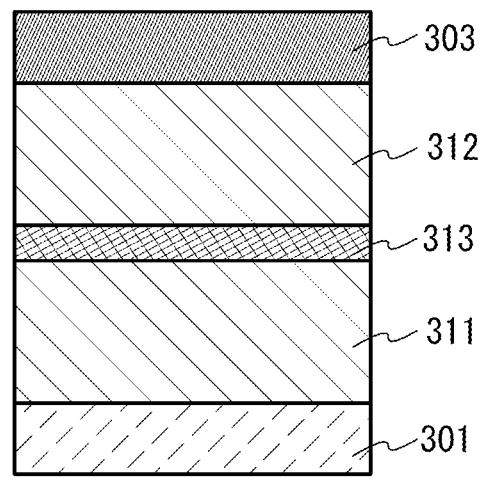
FIGS. 2A and 2B illustrate light-emitting elements according to embodiments of the present invention.

In FIG. 2A, a first light-emitting unit 311 and a second light-emitting unit 312 are stacked between a first electrode 301 and a second electrode 303. In this embodiment, the first electrode 301 functions as an anode and the second electrode 303 functions as a cathode. The first electrode 301 and the second electrode 303 can be the same as those in Embodiment 2. Further, the first light-emitting unit 311 and the second light-emitting unit 312 may have the same or different structures. The first light-emitting unit 311 and the second light-emitting unit 312 may have the same structure as in Embodiment 2, or either of the units may have a structure different from that in Embodiment 2.

Further, a charge generating layer 313 is provided between the first light-emitting unit 311 and the second light-emitting unit 312. The charge generating layer 313 functions such that electrons are injected into one light-emitting unit and holes are injected into the other light-emitting unit by application of voltage between the first electrode 301 and the second electrode 303. In this embodiment, when voltage is applied to the first electrode 301 such that the potential thereof is higher than that of the second electrode 303, the charge generating layer 313 injects electrons into the first light-emitting unit 311 and injects holes into the second light-emitting unit 312.

Note that the charge generating layer 313 preferably has the property of transmitting visible light in terms of light extraction efficiency. Further, the charge generating layer 313 functions even when it has lower conductivity than the first electrode 301 or the second electrode 303.

The charge generating layer 313 may have either a structure containing an organic compound with a high hole-transport property and an electron acceptor (accepter) or a structure containing an organic compound with a high electron-transport property and an electron donor (donor). Alternatively, these structures may be stacked.

In the case of the structure in which an electron acceptor is added to an organic compound with a high hole-transport property, any of the following substances can be used as the organic compound with a high hole-transport property, for example: the heterocyclic compounds according to embodiments of the present invention; aromatic amine compounds such as NPB, TPD, TDATA, MTDATA, and 4,4'-bis[N-(spiro-9,9'-bifluoren-2-yl)-N-phenylamino]biphenyl (abbreviation: BSPB); and the like. The substances mentioned here are mainly ones that have a hole mobility of $10^{-6}$ cm$^2$/V·s or higher. However, substances other than the above substances may be used as long as they are organic compounds with a hole-transport property higher than an electron-transport property.

Further, as the electron acceptor, 7,7,8,8-tetracyano-2,3,5,6-tetrafluoroquinodimethane (abbreviation: F$_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable because it is stable in the air, has a low hygroscopic property, and is easily handled.

In contrast, in the case of the structure in which an electron donor is added to an organic compound with a high electron-transport property, as the organic compound with a high electron-transport property, a metal complex having a quinoline skeleton or a benzoquinoline skeleton, such as Alq, Almq$_3$, BeBq$_2$, or BAlq, or the like can be used, for example. Alternatively, a metal complex having an oxazole-based ligand or a thiazole-based ligand, such as Zn(BOX)$_2$ or Zn(BTZ)$_2$ can be used. Alternatively, other than such a metal complex, PBD, OXD-7, TAZ, BPhen, BCP, or the like can be used. The substances mentioned here are mainly ones that have an electron mobility of $10^{-6}$ cm$^2$/V·s or higher. Note that substances other than the above substances may be used as long as they are organic compounds having an electron-transport property higher than a hole-transport property.

Further, as the electron donor, an alkali metal, an alkaline earth metal, a rare earth metal, a metal belonging to Group 2 or 13 of the periodic table, or an oxide or carbonate thereof can be used. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

Note that by formation of the charge generating layer 313 using any of the above materials, it is possible to suppress an increase in drive voltage caused by stacking the EL layers.

Figure 2B:
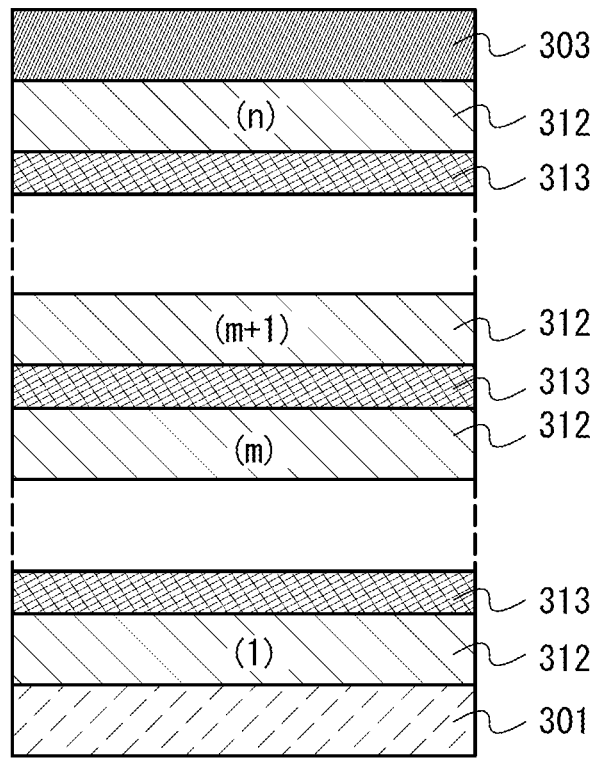

In this embodiment, the light-emitting element having two light-emitting units is described, and one embodiment of the present invention can be similarly applied to a light-emitting element having a stack of three or more light-emitting units as illustrated in FIG. 2B. A plurality of light-emitting units which are partitioned by a charge generating layer is arranged between a pair of electrodes, as in the light-emitting element according to this embodiment, whereby it is possible to achieve an element having a long lifetime which can emit light with a high luminance while current density is kept low.

The light-emitting units emit light having different colors from each other, thereby obtaining light emission of a desired color in the whole light-emitting element. For example, in a light-emitting element having two light-emitting units, the emission colors of a first light-emitting unit and a second light-emitting unit are made complementary, so that the light-emitting element which emits white light as the whole element can be obtained. Note that the word "complementary" means color relationship in which an achromatic color is obtained when colors are mixed. That is, when complementary colored light emitted from substances is mixed, white light can be emitted. Further, the same can be applied to a light-emitting element having three light-emitting units. For example, when a first light-emitting unit emits red light, a second light-emitting unit emits green light, and a third light-emitting unit emits blue light, white light can be emitted from the whole light-emitting element.

This embodiment can be implemented in appropriate combination with the other embodiments and examples below.

Embodiment 4

This embodiment will show, as one embodiment of the present invention, a light-emitting element whose light-emitting layer contains a compound in which a dibenzo[f,h]quinoline ring and a hole-transport skeleton are bonded through an arylene group as a host material and other two or more kinds of organic compounds.

Figure 3:
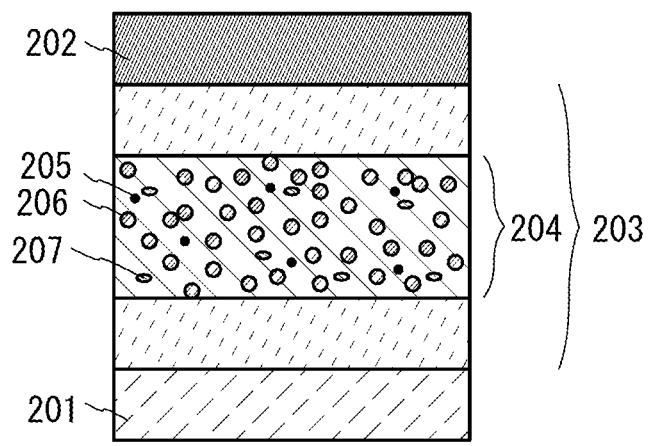
FIG. 3 illustrates a light-emitting device according to one embodiment of the present invention.

A light-emitting element described in this embodiment includes an EL layer 203 between a pair of electrodes (a first electrode 201 and a second electrode 202) as illustrated in FIG. 3. Note that the EL layer 203 includes at least a light-emitting layer 204 and may include a hole-injection layer, a hole-transport layer, an electron-transport layer, an electron-injection layer, a charge generating layer, and the like. Note that substances for the hole-injection layer, the hole-transport layer, the electron-transport layer, the electron-injection layer, and the charge generating layer can be similar to the substances for the hole-injection layer 111, the hole-transport layer 112, the electron-transport layer 114, the electron-injection layer 115, and the charge generating layer 313, respectively, which are described in Embodiments 2 and 3.

In this embodiment, the first electrode 201 functions as an anode, and the second electrode 202 functions as a cathode. Note that structures of the first electrode 201 and the second electrode 202 can be similar to those of the first electrode 101 and the second electrode 103 described in Embodiment 2.

The light-emitting layer 204 described in this embodiment contains a phosphorescent compound 205, a first organic compound 206, and a second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204. In this embodiment, as the first organic compound 206 or the second organic compound 207, it is possible to use the compound according to one embodiment of the present invention, in which a dibenzo[f,h]quinoline ring and a hole-transport skeleton are bonded through an arylene group.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

Note that it is preferable that a triplet excitation energy level ($T_1$ level) of each of the first organic compound 206 and the second organic compound 207 be higher than that of the phosphorescent compound 205. This is because, when the $T_1$ level of the first organic compound 206 (or the second organic compound 207) is lower than that of the phosphorescent compound 205, the triplet excitation energy of the phosphorescent compound 205, which is to contribute to light emission, is quenched by the first organic compound 206 (or the second organic compound 207) and accordingly the emission efficiency is decreased.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (fluorescence spectrum in energy transfer from a singlet excited state, phosphorescence spectrum in energy transfer from a triplet excited state) largely overlap with an absorption spectrum of a guest material (specifically, spectrum in an absorption band on the longest wavelength (lowest energy) side). However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, in this embodiment, a combination of the first organic compound 206 and the second organic compound 207 preferably forms an exciplex (also referred to as excited complex). In that case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex which is located on a longer wavelength side. Moreover, when the first organic compound 206 and the second organic compound 207 are selected in such a manner that the emission spectrum of the exciplex largely overlaps with the absorption spectrum of the guest material, energy transfer from a singlet excited state can be maximized. Note that also in the case of a triplet excited state, energy transfer from the exciplex, not the host material, is assumed to occur.

As the phosphorescent compound 205, a phosphorescent organometallic iridium complex or the like can be used. Although the combination of the first organic compound 206 and the second organic compound 207 can be determined such that an exciplex is formed, a combination of a compound which is likely to accept electrons (compound having an electron-trapping property) and a compound which is likely to accept holes (compound having a hole-trapping property) is preferably employed.

As a compound which is likely to accept electrons, it is possible to use the compound according to one embodiment of the present invention, in which a dibenzo[f,h]quinoline ring and a hole-transport skeleton are bonded through an arylene group.

As a compound which is likely to accept holes, it is possible to use, for example, 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 4,4',4''-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-diphenylamino-9H-fluoren-7-yl)diphenylamine (abbreviation: DPNF), N,N',N''-triphenyl-N,N',N''-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-[9,9-dimethyl-2-{N'-phenyl-N'-(9,9-dimethyl-9H-fluoren-2-yl)}amino-9H-fluoren-7-yl]phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), 3,6-bis[N-(9-phenylcarbazol-3-yl)-N-phenylamino]-9-phenylcarbazole (abbreviation: PCzPCA2), or the like.

The above-described first and second organic compounds 206 and 207 are not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio of the first organic compound 206 to the second organic compound 207 is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of a light-emitting element.

Note that in another structure of the present invention, the light-emitting layer 204 can be formed using a host molecule having a hole-trapping property and a host molecule having an electron-trapping property as the two kinds of organic compounds other than the phosphorescent compound 205 which is the guest material, so that a phenomenon in which holes and electrons are introduced to guest molecules existing in the two kinds of host molecules and the guest molecules are brought into an excited state (i.e., guest coupled with complementary hosts: GCCH) occurs.

At this time, the host molecule having a hole-trapping property and the host molecule having an electron-trapping property can be respectively selected from the above-described compounds which are likely to accept holes and the above-described compounds which are likely to accept electrons.

Note that although the light-emitting element described in this embodiment is one structural example of a light-emitting element, a light-emitting element having another structure which is described in another embodiment can also be applied to a light-emitting device according to one embodiment of the present invention. Further, as a light-emitting device including the above light-emitting element, a passive matrix light-emitting device and an active matrix light-emitting device can be manufactured. It is also possible to manufacture a light-emitting device with a microcavity structure including a light-emitting element which is different from the above light-emitting elements as described in another embodiment. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed using both an n-channel TFT and a p-channel TFT or only either an n-channel TFT or a p-channel TFT. Furthermore, there is no particular limitation on the crystallinity of a semiconductor film used for the TFT. For example, an amorphous semiconductor film, a crystalline semiconductor film, an oxide semiconductor film, or the like can be used.

The structure described in this embodiment can be used in appropriate combination with any of the structures described in the other embodiments and examples below.

Embodiment 5

In this embodiment, a light-emitting device formed using a compound according to one embodiment of the present invention, in which a dibenzo[f,h]quinoline ring and a hole-transport skeleton are bonded through an arylene group, will be described with reference to FIG. 4.

A light-emitting device described in this embodiment has a micro optical resonator (microcavity) structure in which a light resonant effect between a pair of electrodes is utilized. The light-emitting device includes a plurality of light-emitting elements each of which has at least an EL layer 455 between a pair of electrodes (a reflective electrode 451 and a semi-transmissive and semi-reflective electrode 452) as illustrated in FIG. 4. Further, the EL layer 455 includes at least a first light-emitting layer 454B, a second light-emitting layer 454G, and a third light-emitting layer 454R, each of which serves as a light-emitting region. The EL layer 455 may further include a hole-injection layer, a hole-transport layer, an electron-transport layer, an electron-injection layer, a charge generating layer, and the like. Note that at least one of the first light-emitting layer 454B, the second light-emitting layer 454G and the third light-emitting layer 454R contains the compound according to one embodiment of the present invention, in which a dibenzo[f,h]quinoline ring and a hole-transport skeleton are bonded through an arylene group.

Figure 4:
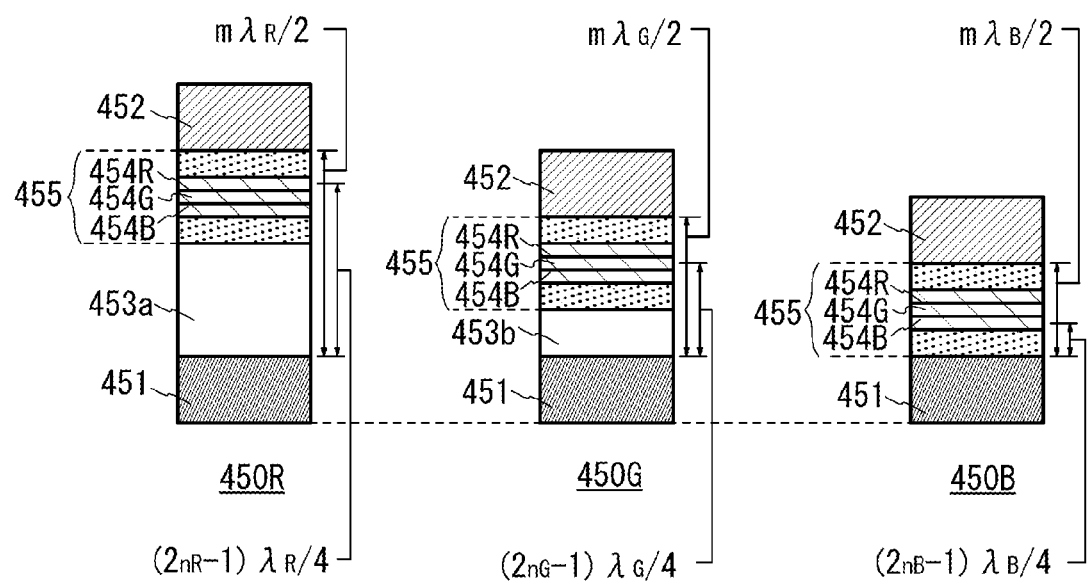
FIG. 4 illustrates a light-emitting device according to one embodiment of the present invention.

This embodiment will show a light-emitting device which includes light-emitting elements (a first light-emitting element 450R, a second light-emitting element 450G and a third light-emitting element 450B) having different structures as illustrated in FIG. 4.

The first light-emitting element 450R has a structure in which a first transparent conductive layer 453a, the EL layer 455, the semi-transmissive and semi-reflective electrode 452 are sequentially stacked over the reflective electrode 451. The second light-emitting element 450G has a structure in which a second transparent conductive layer 453b, the EL layer 455, and the semi-transmissive and semi-reflective electrode 452 are sequentially stacked over the reflective electrode 451. The third light-emitting element 450B has a structure in which the EL layer 455 and the semi-transmissive and semi-reflective electrode 452 are sequentially stacked over the reflective electrode 451.

Note that the reflective electrode 451, the EL layer 455, and the semi-transmissive and semi-reflective electrode 452 are common to the light-emitting elements (the first light-emitting element 450R, the second light-emitting element 450G, and the third light-emitting element 450B).

The EL layer 455 includes the first light-emitting layer 454B, the second light-emitting layer 454G, and the third light-emitting layer 454R. The first light-emitting layer 454B, the second light-emitting layer 454G, and the third light-emitting layer 454R emit a light ($\lambda_B$) having a peak in a wavelength range from 420 nm to 480 nm, a light ($\lambda_G$) having a peak in a wavelength range from 500 nm to 550 nm, and a light ($\lambda_R$) having a peak in a wavelength range from 600 nm to 760 nm, respectively. Thus, in each of the light-emitting elements (the first light-emitting element 450R, the second light-emitting element 450G, and the third light-emitting element 450B), the lights emitted from the first light-emitting layer 454B, the second light-emitting layer 454G, and the third light-emitting layer 454R overlap with each other; accordingly, light having a broad emission spectrum that covers a visible light range can be emitted. Note that the above wavelengths satisfy the relation of $\lambda_B<\lambda_G<\lambda_R$.

Each of the light-emitting elements described in this embodiment has a structure in which the EL layer 455 is interposed between the reflective electrode 451 and the semi-transmissive and semi-reflective electrode 452. The lights emitted in all directions from the light-emitting layers included in the EL layer 455 are resonated by the reflective electrode 451 and the semi-transmissive and semi-reflective electrode 452 which function as a micro optical resonator (microcavity). Note that the reflective electrode 451 is formed using a conductive material having reflectivity, and a film whose visible light reflectivity is 40% to 100%, preferably 70% to 100%, and whose resistivity is $1\times10^{-2}$ Ω·cm or lower is used. In addition, the semi-transmissive and semi-reflective electrode 452 is formed using a conductive material having reflectivity and a conductive material having a light-transmitting property, and a film whose visible light reflectivity is 20% to 80%, preferably 40% to 70%, and whose resistivity is $1\times10^{-2}$ Ω·cm or lower is used.

In this embodiment, the thicknesses of the transparent conductive layers (the first transparent conductive layer 453a and the second transparent conductive layer 453b) provided in the first light-emitting element 450R and the second light-emitting element 450G, respectively, are varied between the light-emitting elements, whereby the light-emitting elements differ in the optical path length from the reflective electrode 451 to the semi-transmissive and semi-reflective electrode 452. In other words, in light having a broad emission spectrum, which is emitted from the light-emitting layers of each of the light-emitting elements, light with a wavelength that is resonated between the reflective electrode 451 and the semi-transmissive and semi-reflective electrode 452 can be enhanced while light with a wavelength that is not resonated therebetween can be attenuated. Thus, when the elements differ in the optical path length from the reflective electrode 451 to the semi-transmissive and semi-reflective electrode 452, light with different wavelengths can be extracted.

Note that the optical path length (also referred to as optical distance) is expressed as a product of an actual distance and a refractive index, and in this embodiment, is a product of an actual thickness and n (refractive index). That is, the following relation is satisfied: an optical path length=actual thickness×n.

Further, the optical path length from the reflective electrode 451 to the semi-transmissive and semi-reflective electrode 452 is set to $m\lambda_R/2$ (m is a natural number of 1 or more) in the first light-emitting element 450R; the optical path length from the reflective electrode 451 to the semi-transmissive and semi-reflective electrode 452 is set to $m\lambda_G/2$ (m is a natural number of 1 or more) in the second light-emitting element 450G; and the optical path length from the reflective electrode 451 to the semi-transmissive and semi-reflective electrode 452 is set to $m\lambda_B/2$ (m is a natural number of 1 or more) in the third light-emitting element 450B.

In this manner, the light ($\lambda_R$) emitted from the third light-emitting layer 454R included in the EL layer 455 is mainly extracted from the first light-emitting element 450R, the light ($\lambda_G$) emitted from the second light-emitting layer 454G included in the EL layer 455 is mainly extracted from the second light-emitting element 450G, and the light ($\lambda_B$) emitted from the first light-emitting layer 454B included in the EL layer 455 is mainly extracted from the third light-emitting element 450B. Note that the light extracted from each of the light-emitting elements is emitted through the semi-transmissive and semi-reflective electrode 452 side.

Further, strictly speaking, the optical path length from the reflective electrode 451 to the semi-transmissive and semi-reflective electrode 452 can be the distance from a reflection region in the reflective electrode 451 to a reflection region in the semi-transmissive and semi-reflective electrode 452. However, it is difficult to precisely determine the positions of the reflection regions in the reflective electrode 451 and the semi-transmissive and semi-reflective electrode 452; therefore, it is assumed that the above effect can be sufficiently obtained wherever the reflection regions may be set in the reflective electrode 451 and the semi-transmissive and semi-reflective electrode 452.

Next, the optical path length from the reflective electrode 451 to the third light-emitting layer 454R is adjusted to $(2n_R-1)\lambda_R/4$ ($n_R$ is a natural number of 1 or more) because in the first light-emitting element 450R, light (first reflected light) that is reflected by the reflective electrode 451 of the light emitted from the third light-emitting layer 454R interferes with light (first incident light) that directly enters the semi-transmissive and semi-reflective electrode 452 from the third light-emitting layer 454R. By adjusting the optical path length, the phases of the first reflected light and the first incident light can be aligned with each other and the light emitted from the third light-emitting layer 454R can be amplified.

Note that, strictly speaking, the optical path length from the reflective electrode 451 to the third light-emitting layer 454R can be the optical path length from a reflection region in the reflective electrode 451 to a light-emitting region in the third light-emitting layer 454R. However, it is difficult to precisely determine the positions of the reflection region in the reflective electrode 451 and the light-emitting region in the third light-emitting layer 454R; therefore, it is assumed that the above effect can be sufficiently obtained wherever the reflection region and the light-emitting region may be set in the reflective electrode 451 and the third light-emitting layer 454R, respectively.

Next, the optical path length from the reflective electrode 451 to the second light-emitting layer 454G is adjusted to $(2n_G-1)\lambda_G/4$ ($n_G$ is a natural number of 1 or more) because in the second light-emitting element 450G light (second reflected light) that is reflected by the reflective electrode 451 of the light emitted from the second light-emitting layer 454G interferes with light (second incident light) that directly enters the semi-transmissive and semi-reflective electrode 452 from the second light-emitting layer 454G By adjusting the optical path length, the phases of the second reflected light and the second incident light can be aligned with each other and the light emitted from the second light-emitting layer 454G can be amplified.

Note that, strictly speaking, the optical path length from the reflective electrode 451 to the second light-emitting layer 454G can be the optical path length from a reflection region in the reflective electrode 451 to a light-emitting region in the second light-emitting layer 454G. However, it is difficult to precisely determine the positions of the reflection region in the reflective electrode 451 and the light-emitting region in the second light-emitting layer 454G; therefore, it is assumed that the above effect can be sufficiently obtained wherever the reflection region and the light-emitting region may be set in the reflective electrode 451 and the second light-emitting layer 454G, respectively.

Next, the optical path length from the reflective electrode 451 to the first light-emitting layer 454B is adjusted to $(2n_B-1)\lambda_B/4$ ($n_B$ is a natural number of 1 or more) because in the third light-emitting element 450B, light (third reflected light) that is reflected by the reflective electrode 451 of the light emitted from the first light-emitting layer 454B interferes with light (third incident light) that directly enters the semi-transmissive and semi-reflective electrode 452 from the first light-emitting layer 454B. By adjusting the optical path length, the phases of the third reflected light and the third incident light can be aligned with each other and the light emitted from the first light-emitting layer 454B can be amplified.

Note that, strictly speaking, the optical path length from the reflective electrode 451 to the first light-emitting layer 454B can be the optical path length from a reflection region in the reflective electrode 451 to a light-emitting region in the first light-emitting layer 454B. However, it is difficult to precisely determine the positions of the reflection region in the reflective electrode 451 and the light-emitting region in the first light-emitting layer 454B; therefore, it is assumed that the above effect can be sufficiently obtained wherever the reflection region and the light-emitting region may be set in the reflective electrode 451 and the first light-emitting layer 454B, respectively.

Note that although each of the light-emitting elements in the above-described structure includes a plurality of light-emitting layers in the EL layer, the present invention is not limited thereto; for example, the structure of the tandem (stacked type) light-emitting element which is described in Embodiment 3 can be combined, in which case a plurality of EL layers is provided so that a charge generating layer is interposed therebetween in one light-emitting element and one or more light-emitting layers are formed in each of the EL layers.

The light-emitting device described in this embodiment has a microcavity structure, in which light with wavelengths which differ depending on the light-emitting elements can be extracted even when they include the same EL layers, so that it is not needed to form light-emitting elements for the colors of R, G, and B. Therefore, the above structure is advantageous for full color display owing to easiness in achieving higher resolution display or the like. In addition, emission intensity with a predetermined wavelength in the front direction can be increased, whereby power consumption can be reduced. The above structure is particularly useful in the case of being applied to a color display (image display device) including pixels of three or more colors but may also be applied to lighting or the like.

The structure described in this embodiment can be used in appropriate combination with any of the structures described in the other embodiments and examples below.

Embodiment 6

In this embodiment, a light-emitting device having a light-emitting element according to one embodiment of the present invention will be described with reference to FIGS. 5A and 5B. Note that FIG. 5A is a top view of a light-emitting device, and FIG. 5B is a cross-sectional view taken along lines A-B and C-D of FIG. 5A.

Figure 5A:
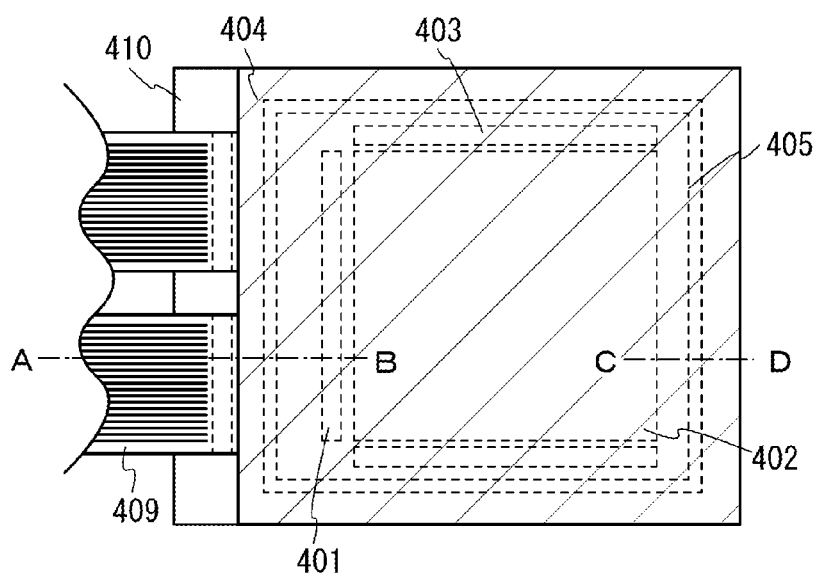
FIGS. 5A and 5B illustrate a light-emitting device according to one embodiment of the present invention.
Figure 5B:
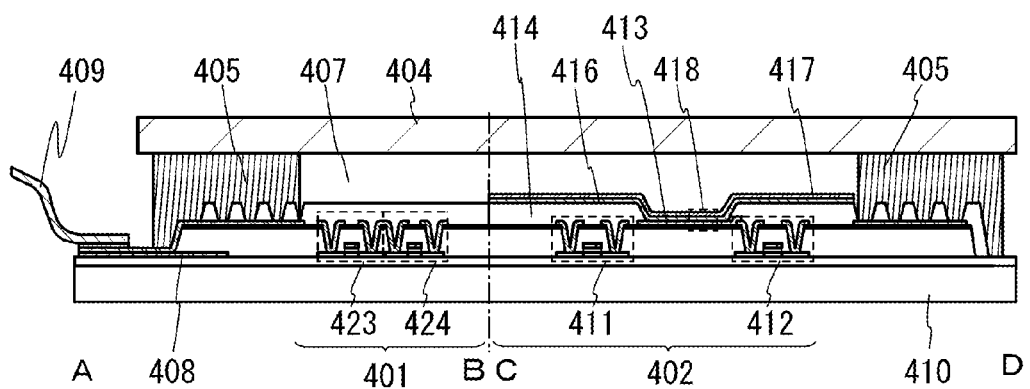

In FIG. 5A, reference numerals 401, 402 and 403 which are shown by dotted lines denote a driver circuit portion (source side driver circuit), a pixel portion, and a driver circuit portion (gate side driver circuit), respectively. Reference numeral 404 denotes a sealing substrate, reference numeral 405 denotes a sealant, and a portion enclosed by the sealant 405 is a space.

Note that a lead wiring 408 is a wiring for transmitting signals that are to be inputted to the source side driver circuit 401 and the gate side driver circuit 403, and receives a video signal, a clock signal, a start signal, a reset signal, and the like from a flexible printed circuit (FPC) 409 which serves as an external input terminal. Note that although only an FPC is illustrated here, a printed wiring board (PWB) may be attached thereto. The light-emitting device in this specification includes, in its category, not only the light-emitting device itself but also the light-emitting device provided with the FPC or the PWB.

Next, a cross-sectional structure is described with reference to FIG. 5B. The driver circuit portion and the pixel portion are formed over an element substrate 410. In this case, one pixel in the pixel portion 402 and the source side driver circuit 401 which is the driver circuit portion are illustrated.

Note that as the source side driver circuit 401, a CMOS circuit which is obtained by combining an n-channel TFT 423 and a p-channel TFT 424 is formed. Further, the driver circuit may be formed using any of a variety of CMOS circuits, PMOS circuits, and NMOS circuits. Although this embodiment illustrates a driver-integrated type where the driver circuit is formed over the substrate, the present invention is not limited to this, and the driver circuit may be formed outside the substrate, not over the substrate.

The pixel portion 402 includes a plurality of pixels having a switching TFT 411, a current control TFT 412, and a first electrode 413 electrically connected to a drain of the current control TFT 412. An insulator 414 is formed to cover an end portion of the first electrode 413. Here, the insulator 414 is formed using a positive type photosensitive acrylic resin film.

To improve the coverage, the insulator 414 is provided such that either an upper end portion or a lower end portion of the insulator 414 has a curved surface with a curvature. For example, when positive type photosensitive acrylic resin is used as a material for the insulator 414, the insulator 414 preferably has a curved surface with a curvature radius (0.2 μm to 3 μm) only as the upper end. The insulator 414 can be formed using either a negative type photosensitive resin which becomes insoluble in an etchant by light irradiation or a positive type photosensitive resin which becomes soluble in an etchant by light irradiation.

A light-emitting layer 416 and a second electrode 417 are formed over the first electrode 413. Here, as a material for forming the first electrode 413 functioning as the anode, it is preferable to use a material having a high work function. For example, it is possible to use a single layer of an ITO film, an indium tin oxide film that contains silicon, an indium oxide film that contains 2 wt % to 20 wt % of zinc oxide, a titanium nitride film, a chromium film, a tungsten film, a Zn film, a Pt film, or the like, a stacked layer of a titanium nitride film and a film that mainly contains aluminum, a three-layer structure of a titanium nitride film, a film that mainly contains aluminum and a titanium nitride film, or the like. Note that, when a stacked layer is employed, the resistance of a wiring is low and a favorable ohmic contact is obtained.

In addition, the light-emitting layer 416 is formed by any of various methods such as an evaporation method using an evaporation mask, a droplet discharging method like an inkjet method, a printing method, and a spin coating method. The light-emitting layer 416 contains the heterocyclic compound described in Embodiment 1. Further, another material included in the light-emitting layer 416 may be a low molecular material, an oligomer, a dendrimer, a high molecular material, or the like.

As a material used for the second electrode 417 which is formed over the light-emitting layer 416 and serves as a cathode, it is preferable to use a material having a low work function (e.g., Al, Mg, Li, Ca, or an alloy or compound thereof such as Mg—Ag, Mg—In, or Al—Li). In order that light generated in the light-emitting layer 416 be transmitted through the second electrode 417, a stack of a metal thin film having a reduced thickness and a transparent conductive film (e.g., ITO, indium oxide containing 2 wt % to 20 wt % of zinc oxide, indium oxide-tin oxide that contains silicon or silicon oxide, or zinc oxide) is preferably used for the second electrode 417.

The sealing substrate 404 is attached to the element substrate 410 with the sealant 405; thus, a light-emitting element 418 is provided in the space 407 enclosed by the element substrate 410, the sealing substrate 404, and the sealant 405. Note that the space 407 is filled with a filler such as an inert gas (e.g., nitrogen or argon) or the sealant 405.

Note that as the sealant 405, an epoxy-based resin is preferably used. A material used for these is desirably a material which does not transmit moisture or oxygen as much as possible. As a material for the sealing substrate 404, a glass substrate, a quartz substrate, or a plastic substrate including fiberglass-reinforced plastics (FRP), polyvinyl fluoride (PVF), polyester, acrylic resin, or the like can be used.

As described above, the active matrix light-emitting device having the light-emitting element according to one embodiment of the present invention can be obtained.

Figure 6A:
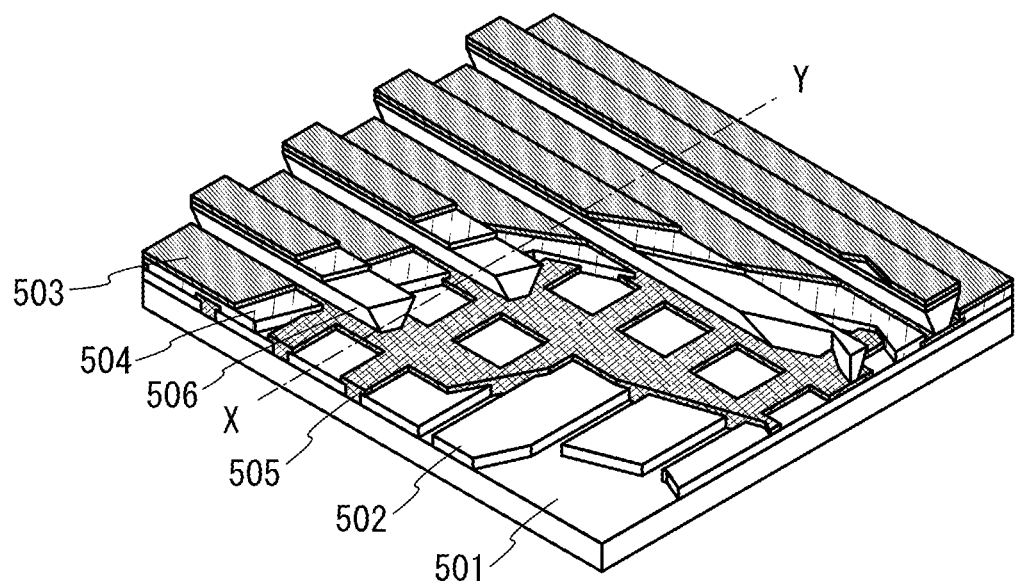
FIGS. 6A and 6B illustrate a light-emitting device according to one embodiment of the present invention.
Figure 6B:
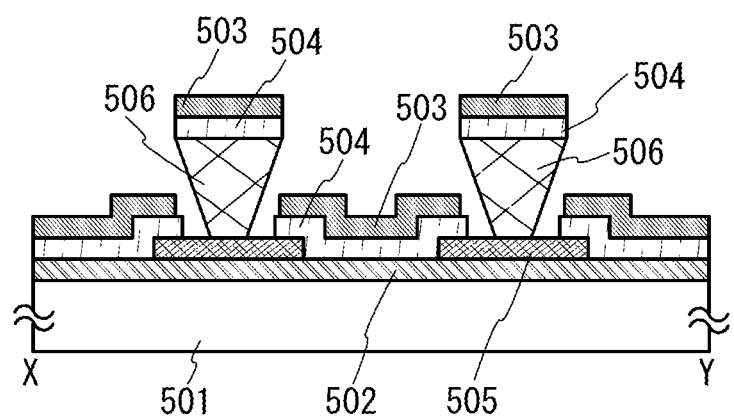

Further, the light-emitting element according to one embodiment of the present invention can be used for a passive matrix light-emitting device instead of the above active matrix light-emitting device. FIGS. 6A and 6B illustrate a perspective view and a cross-sectional view of a passive matrix light-emitting device using the light-emitting element according to one embodiment of the present invention. FIG. 6A is a perspective view of the light-emitting device, and FIG. 6B is a cross-sectional view taken along line X-Y of FIG. 6A.

In FIGS. 6A and 6B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that the distance between one sidewall and the other sidewall gradually decreases toward the surface of the substrate. In other words, a cross section taken along the direction of the short side of the partition layer 506 is trapezoidal, and the base (side parallel to the plane of the insulating layer 505 and in contact with the insulating layer 505) is shorter than the upper side (side parallel to the plane of the insulating layer 505 and not being in contact with the insulating layer 505). By providing the partition layer 506 in such a manner, a defect of the light-emitting element due to static electricity or the like can be prevented.

Thus, the passive matrix light-emitting device having the light-emitting element according to one embodiment of the present invention can be obtained.

The light-emitting devices described in this embodiment (the active matrix light-emitting device and the passive matrix light-emitting device) are both formed using the light-emitting element according to one embodiment of the present invention, thereby having low power consumption.

This embodiment can be implemented in appropriate combination with the other embodiments and examples below.

Embodiment 7

This embodiment will show electronic devices including any of the light-emitting devices according to one embodiment of the present invention described in the above embodiments. Examples of the electronic devices include cameras such as video cameras and digital cameras, goggle type displays, navigation systems, audio reproducing devices (e.g., car audio systems and audio systems), computers, game machines, portable information terminals (e.g., mobile computers, cellular phones, portable game machines, and electronic book readers), image reproducing devices in which a recording medium is provided (specifically, devices that are capable of reproducing recording media such as digital versatile discs (DVDs) and provided with a display device that can display an image), and the like. Specific examples of these electronic devices are illustrated in FIGS. 7A to 7E.

Figure 7A:
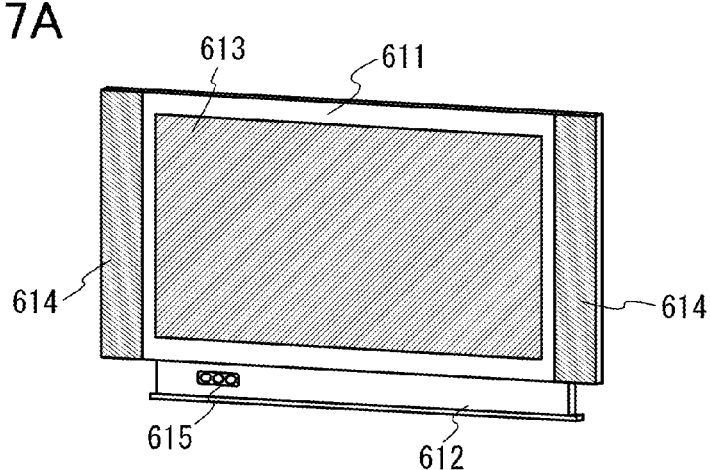
FIGS. 7A to 7D illustrate electronic devices according to embodiments of the present invention.

FIG. 7A illustrates a television set according to one embodiment of the present invention, which includes a housing 611, a supporting base 612, a display portion 613, speaker portions 614, video input terminals 615, and the like. In this television set, the light-emitting device according to one embodiment of the present invention can be applied to the display portion 613. Since the light-emitting device according to one embodiment of the present invention is driven at a low voltage and has high current efficiency, by the application of the light-emitting device according to one embodiment of the present invention, a television set with reduced power consumption can be obtained.

Figure 7B:
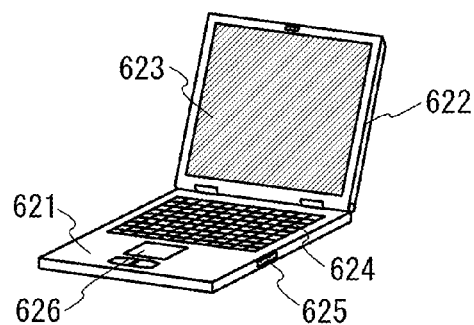

FIG. 7B illustrates a computer according to one embodiment of the present invention, which includes a main body 621, a housing 622, a display portion 623, a keyboard 624, an external connection port 625, a pointing device 626, and the like. In this computer, the light-emitting device according to one embodiment of the present invention can be applied to the display portion 623. Since the light-emitting device according to one embodiment of the present invention is driven at a low voltage and has high current efficiency, by the application of the light-emitting device according to one embodiment of the present invention, a computer with reduced power consumption can be obtained.

Figure 7C:
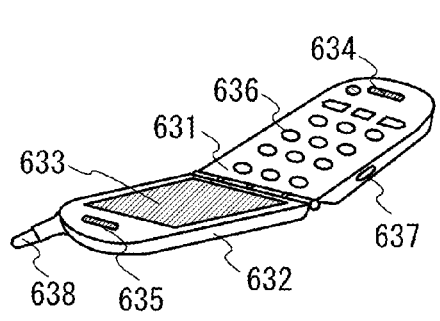

FIG. 7C illustrates a cellular phone according to one embodiment of the present invention, which includes a main body 631, a housing 632, a display portion 633, an audio input portion 634, an audio output portion 635, operation keys 636, an external connection port 637, an antenna 638, and the like. In this cellular phone, the light-emitting device according to one embodiment of the present invention can be applied to the display portion 633. Since the light-emitting device according to one embodiment of the present invention is driven at a low voltage and has high current efficiency, by the application of the light-emitting device according to one embodiment of the present invention, a cellular phone with reduced power consumption can be obtained.

Figure 7D:
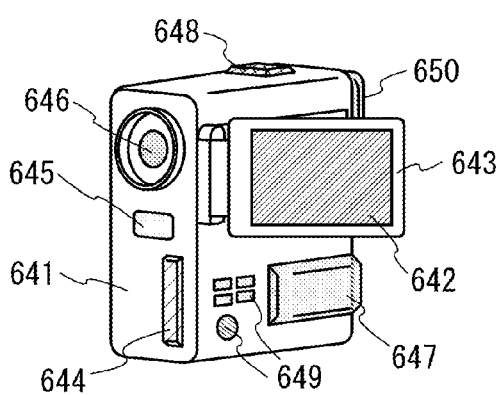

FIG. 7D shows a camera according to one embodiment of the present invention, which includes a main body 641, a display portion 642, a housing 643, an external connection port 644, a remote control receiving portion 645, an image receiving portion 646, a battery 647, an audio input portion 648, operation keys 649, an eyepiece portion 650, and the like. In this camera, the light-emitting device according to one embodiment of the present invention can be applied to the display portion 642. Since the light-emitting device according to one embodiment of the present invention is driven at a low voltage and has high current efficiency, by the application of the light-emitting device according to one embodiment of the present invention, a camera with reduced power consumption can be obtained.

As described above, the applicable range of the light-emitting device according to one embodiment of the present invention is so wide that the light-emitting device can be applied to electronic devices in a variety of fields. With use of the light-emitting device according to one embodiment of the present invention, an electronic device with reduced power consumption can be obtained.

Figure 8A:
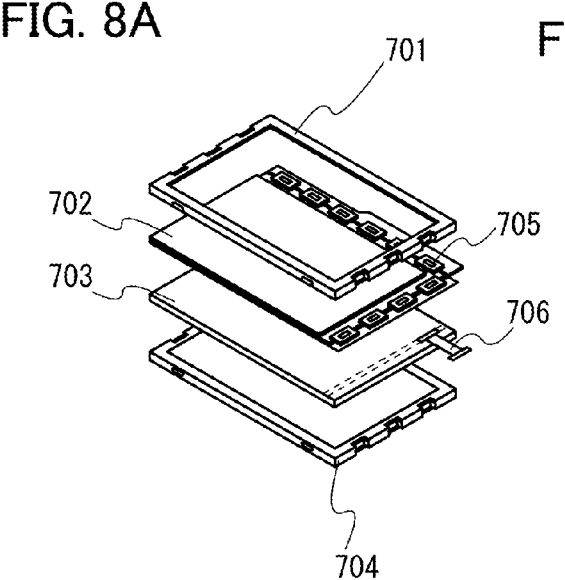
FIGS. 8A to 8C illustrate lighting devices and light-emitting devices according to embodiments of the present invention.

The light-emitting device according to one embodiment of the present invention can also be used as a lighting device. FIG. 8A illustrates an example of a liquid crystal display device using the light-emitting device according to one embodiment of the present invention as a backlight. The liquid crystal display device illustrated in FIG. 8A includes a housing 701, a liquid crystal layer 702, a backlight 703, and a housing 704. The liquid crystal layer 702 is connected to a driver IC 705. The light-emitting device according to one embodiment of the present invention is used as the backlight 703, and current is supplied through a terminal 706.

By using the light-emitting device according to one embodiment of the present invention as a backlight of a liquid crystal display device as described above, a backlight with low power consumption can be obtained. Moreover, since the light-emitting device according to one embodiment of the present invention is a lighting device for surface light emission and the enlargement of the light-emitting device is possible, the backlight can be made larger. Accordingly, a larger-area liquid crystal display device with low power consumption can be obtained.

Figure 8B:
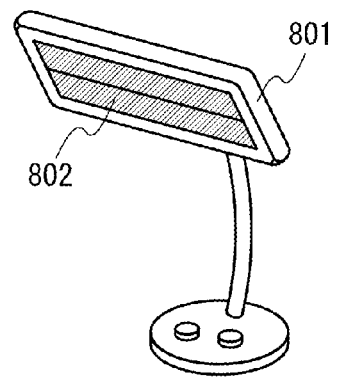

Next, FIG. 8B illustrates an example in which the light-emitting device according to one embodiment of the present invention is used for a desk lamp which is a lighting device. The desk lamp illustrated in FIG. 8B has a housing 801 and a light source 802, and the light-emitting device according to one embodiment of the present invention is used as the light source 802. Since the light-emitting device according to one embodiment of the present invention is driven at a low voltage and has high current efficiency, by the application of the light-emitting device according to one embodiment of the present invention, a desk lamp with reduced power consumption can be obtained.

Figure 8C:
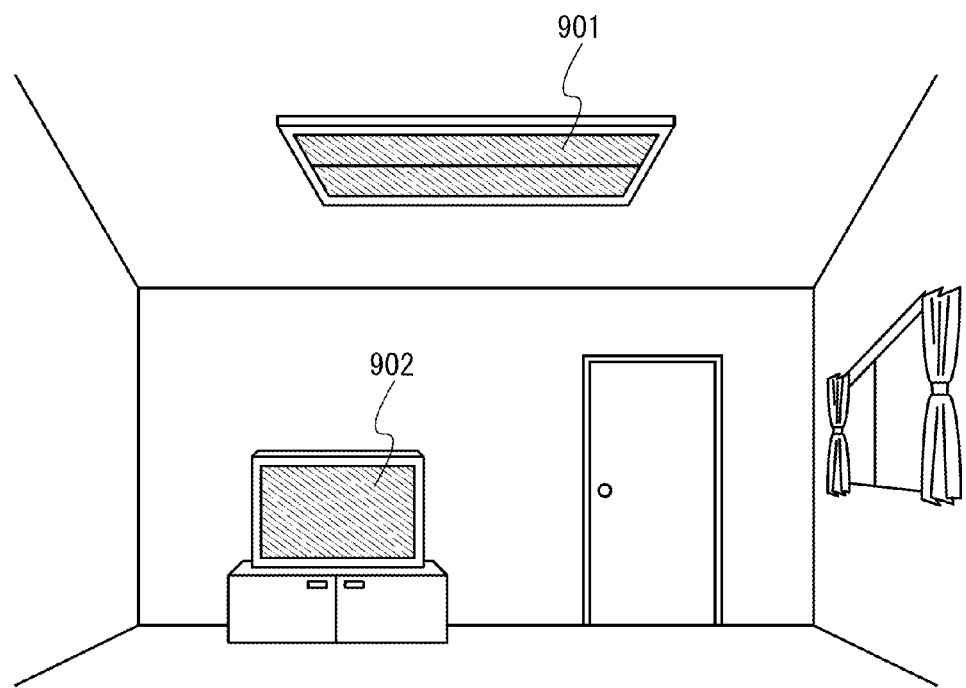

Next, FIG. 8C illustrates an example in which the light-emitting device according to one embodiment of the present invention is used for an indoor lighting device 901. Since the light-emitting device according to one embodiment of the present invention can also have a larger area, the light-emitting device according to one embodiment of the present invention can be used as a lighting system having a large area. Since the light-emitting device according to one embodiment of the present invention is driven at a low voltage and has high current efficiency, by the application of the light-emitting device according to one embodiment of the present invention, a lighting device with reduced power consumption can be obtained. In a room where the light-emitting device according to one embodiment of the present invention is used as the indoor lighting device 901 as described above, a television set 902 according to one embodiment of the present invention as described referring to FIG. 7A can be installed so that pubic broadcasting and movies can be watched.

This embodiment can be implemented in appropriate combination with the other embodiments and examples below.

Example 1

This example will show a method of synthesizing 2-[3-(dibenzothiophen-4-yl)phenyl]dibenzo[f,h]quinoline (abbreviation: 2mDBTPDBQu-II) represented by the following structural formula (101).

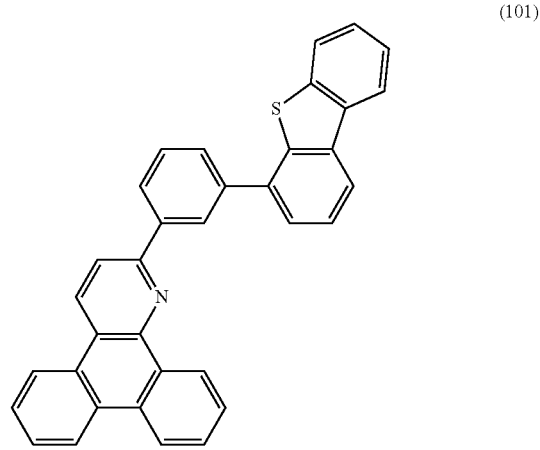 [SMILES: c1ccc(-c2cc3c4ccccc4c4ccccc4c3nc2-c2cccc(-c3cccc4c3oc3ccccc34)c2)cc1]

2mDBTPDBQu-II (101)

Synthesis of 2-[3-(dibenzothiophen-4-yl)phenyl]dibenzo[f,h]quinoline (abbreviation: 2mDBTPDBQu-II)

A synthesis scheme of 2-[3-(dibenzothiophen-4-yl)phenyl]dibenzo[f,h]quinoline (abbreviation: 2mDBTPDBQu-II) is shown in (C-1).

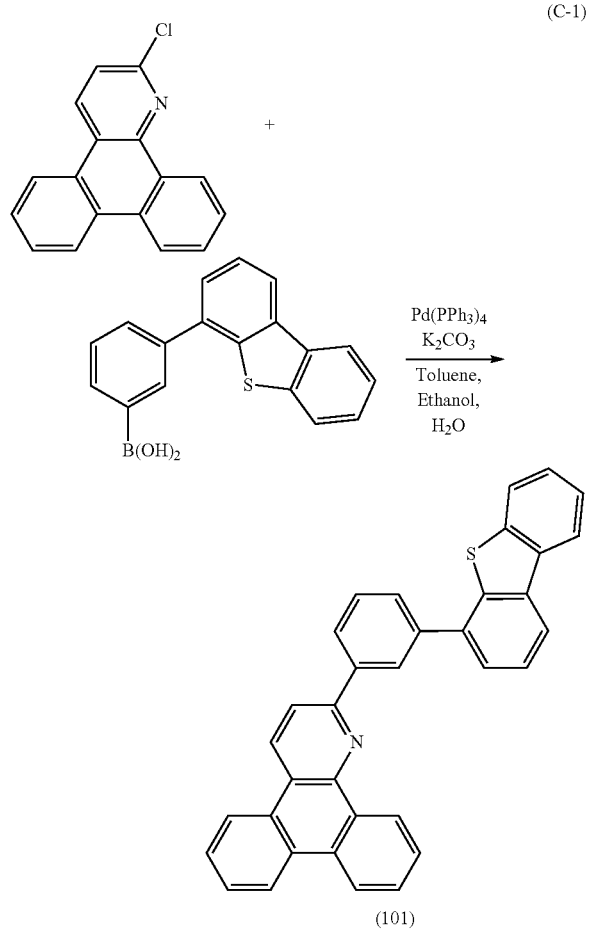

In a 100-mL three-neck flask, 0.46 g (1.7 mmol) of 2-chlorodibenzo[f,h]quinoline, 0.62 g (2.0 mmol) of 3-(dibenzothiophen-4-yl)phenylboronic acid, 20 mL of toluene, 2 mL of ethanol, and 2 mL of a 2M aqueous solution of potassium carbonate were put. The mixture was degassed by being stirred under reduced pressure, and the air in the flask was replaced with nitrogen. To the mixture, 65 mg (56 μmol) of tetrakis(triphenylphosphine)palladium(0) was added, and the mixture was stirred under nitrogen stream at 80° C. for 7 hours. After a predetermined time, water was added to the mixture, and an aqueous layer was extracted with toluene. The obtained extract combined with the organic layer was washed with a saturated aqueous solution of sodium carbonate and a saturated solution of sodium chloride, and the resulting organic layer was dried with magnesium sulfate. The obtained mixture was gravity filtered, and the filtrate was condensed to give an oily substance. The obtained oily substance was purified by silica gel column chromatography (toluene:hexane=1:1), so that a solid was obtained. The solid was purified by high performance liquid column chromatography. The high performance liquid column chromatography was performed using chloroform as a developing solvent. The obtained fraction was condensed to obtain a solid. A methanol suspension of the obtained solid was irradiated with ultrasonic waves, and a solid was collected by suction filtration, so that the objective substance was obtained as 0.68 g of white powder in 79% yield.

Then, 0.66 g of the obtained white powder of 2-[3-(dibenzothiophen-4-yl)phenyl]dibenzo[f,h]quinoline was purified by a train sublimation method. The purification was performed under such conditions that the pressure was 2.7 Pa, the argon flow rate was 5.0 mL/min, so that 2-[3-(dibenzothiophen-4-yl)phenyl]dibenzo[f,h]quinoline was heated at 280° C. for 14 hours. After the purification, 0.60 g of a white solid of 2-[3-(dibenzothiophen-4-yl)phenyl]dibenzo[f,h]quinoline was obtained in 90% yield.

A nuclear magnetic resonance ($^1$H NMR) method identified this compound as 2-[3-(dibenzothiophen-4-yl)phenyl]dibenzo[f,h]quinoline (abbreviation: 2mDBTPDBQu-II), which was the objective substance.

$^1$H NMR data of the obtained substance are as follows:

$^1$H NMR (CDCl$_3$, 300 MHz): δ=7.48-7.51 (m, 2H), 7.61-7.89 (m, 9H), 8.16 (d, J=8.4 Hz, 1H), 8.22-8.25 (m, 2H), 8.44 (d, J=7.8 Hz, 1H), 8.60-8.72 (m, 3H), 8.79 (s, 1H), 8.97 (d, J=8.7 Hz, 1H), 9.57-9.60 (m, 1H).

Figure 9A:
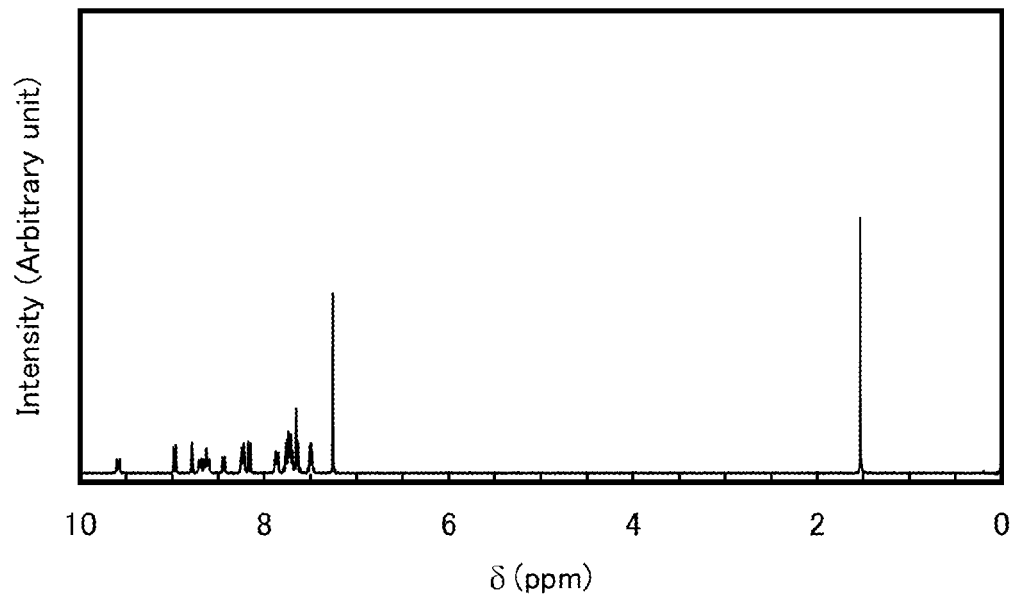
FIGS. 9A and 9B show $^1$H NMR charts of 2-[3-(dibenzothiophen-4-yl)phenyl]dibenzo[f,h]quinoline.
Figure 9B:
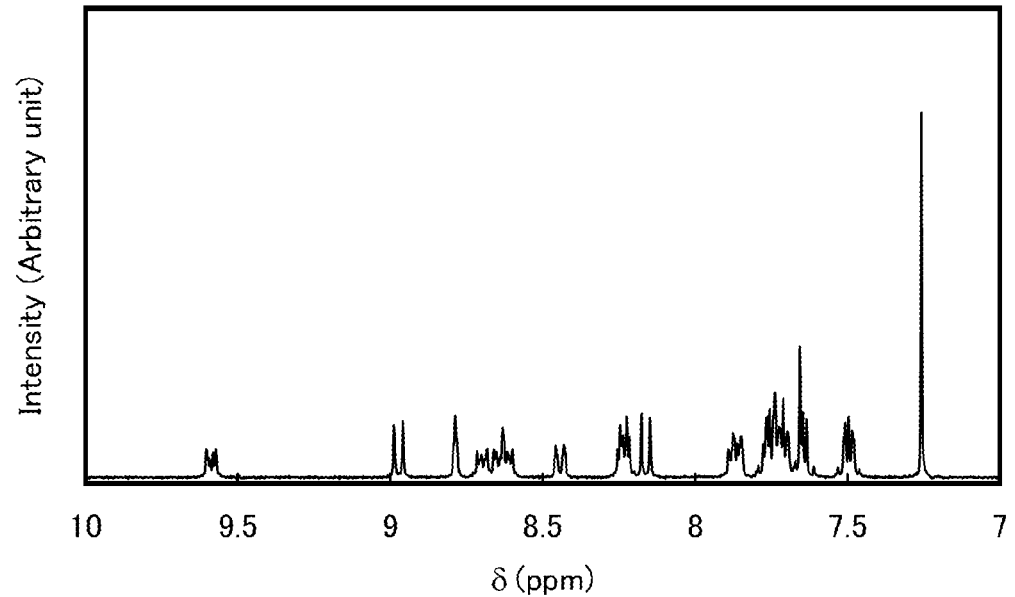

$^1$H NMR charts are shown in FIGS. 9A and 9B. Note that FIG. 9B is a chart showing an enlarged part of FIG. 9A in the range of 7.0 ppm to 10.0 ppm.

Figure 10A:
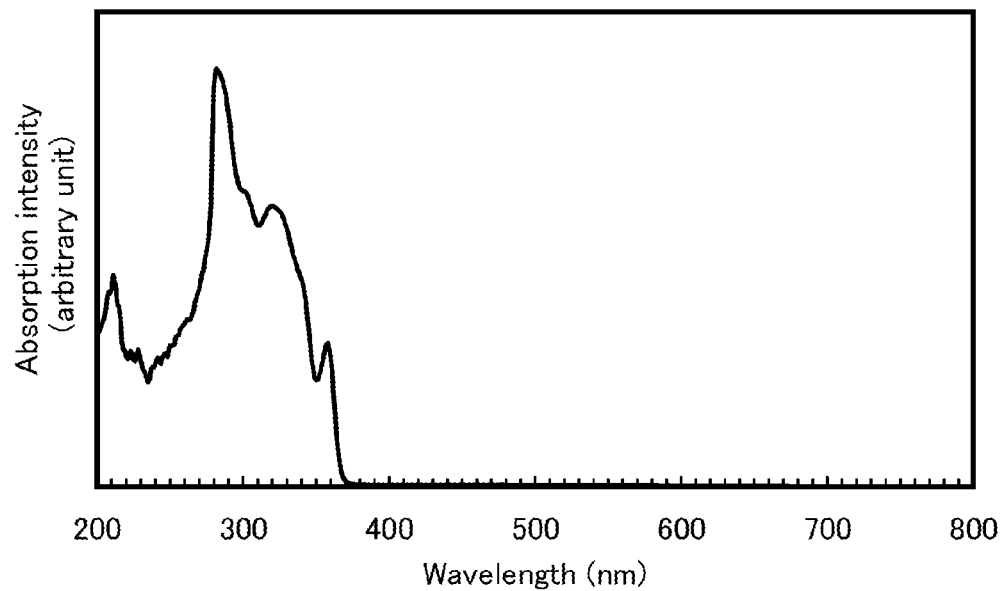
FIGS. 10A and 10B show absorption and emission spectra of a toluene solution of 2-[3-(dibenzothiophen-4-yl)phenyl]dibenzo[f,h]quinoline.
Figure 10B:
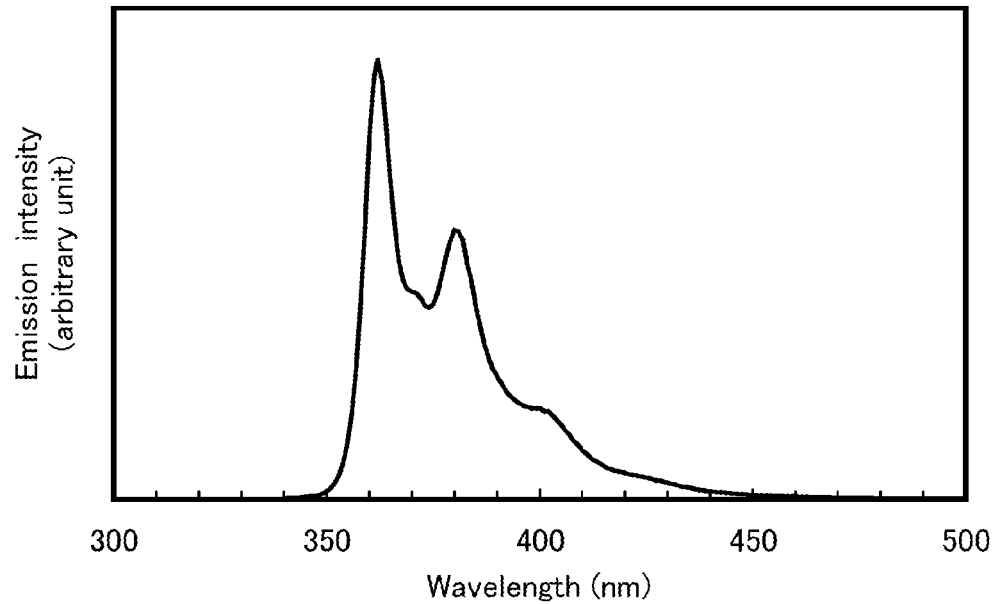
Figure 11A:
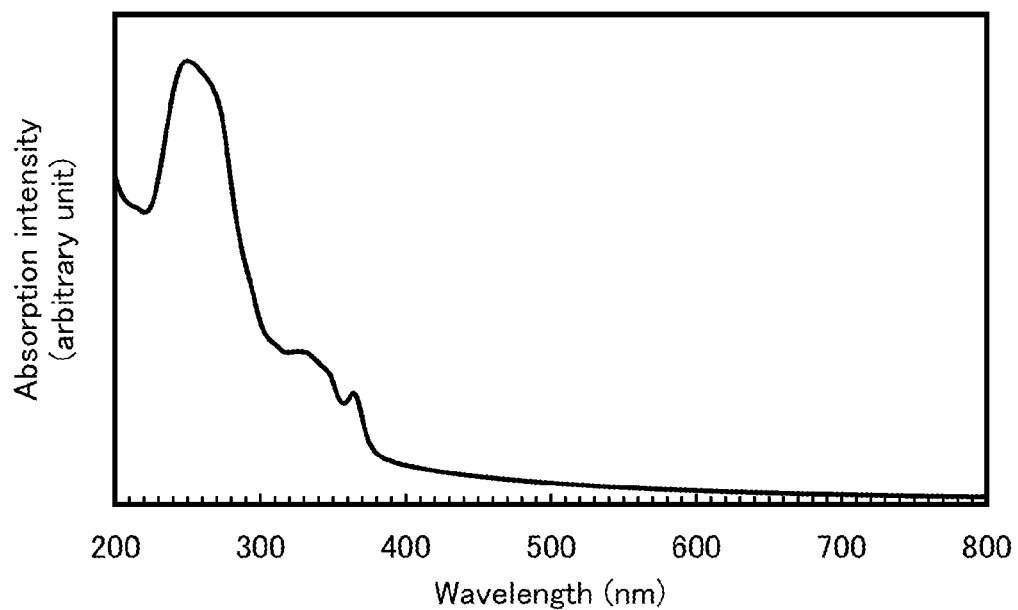
FIGS. 11A and 11B show absorption and emission spectra of a thin film of 2-[3-(dibenzothiophen-4-yl)phenyl]dibenzo[f,h]quinoline.
Figure 11B:
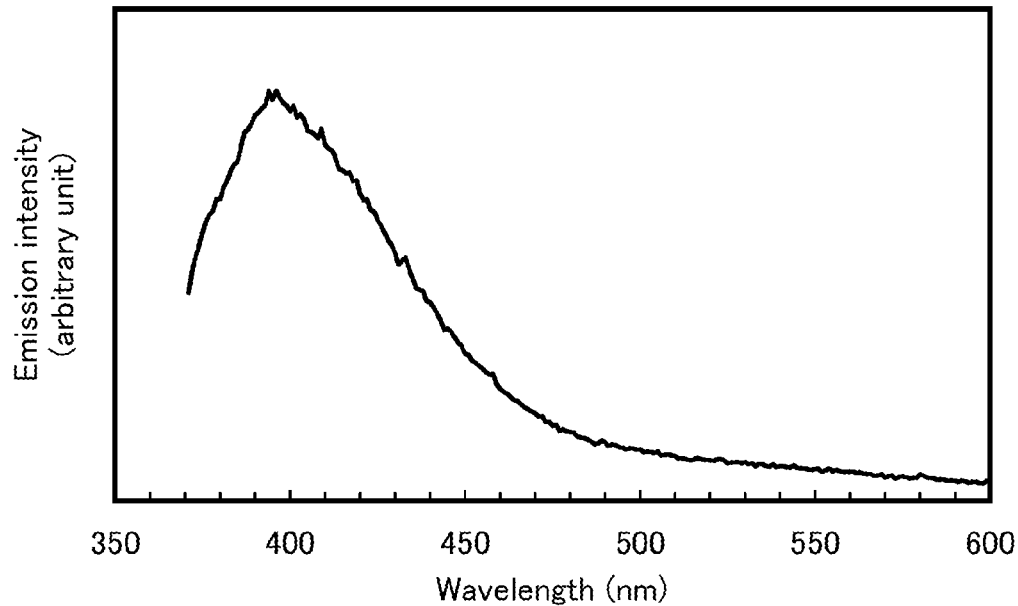

Further, FIG. 10A shows an absorption spectrum of a toluene solution of 2mDBTPDBQu-II (abbreviation), and FIG. 10B shows an emission spectrum thereof. Furthermore, FIG. 11A shows an absorption spectrum of a thin film of 2mDBTPDBQu-II, and FIG. 11B shows an emission spectrum thereof. The measurement of the absorption spectrum was conducted by using a UV-visible spectrophotometer (V-550, manufactured by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 10A and 10B and FIGS. 11A and 11B, the horizontal axis represents wavelength (nm) and the vertical axis represents intensity (arbitrary unit). With the toluene solution, absorption peaks were at around 282 nm, 320 nm, and 358 nm, and emission wavelength peaks were at 362 nm, 380 nm, and 402 nm (at an excitation wavelength of 327 nm). With the thin film, absorption peaks were at around 250 nm, 264 nm, 325 nm, 344 nm, and 364 nm, and a peak of the emission wavelength was at 395 nm (at an excitation wavelength of 365 nm).

Example 2

Figure 12:
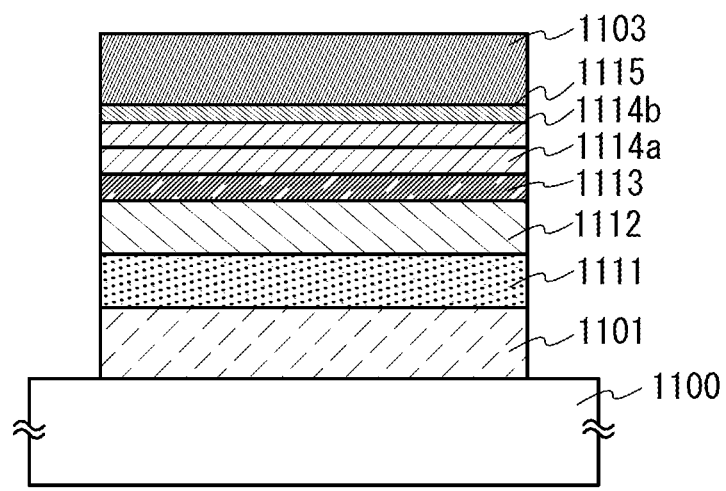
FIG. 12 illustrates a light-emitting element of examples.

In this example, light-emitting elements according to embodiments of the present invention (a light-emitting element 1 and a light-emitting element 3), and a light-emitting element for comparison (a comparative light-emitting element 2) will be described with reference to FIG. 12. Chemical formulas of materials used in this example are shown below.

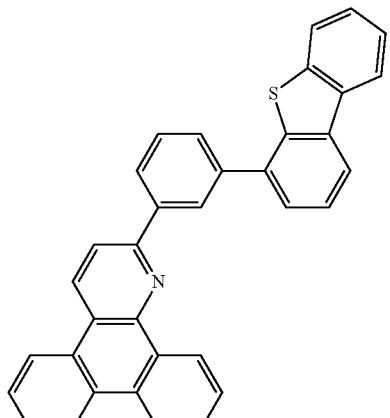
2mDBTPDBQu-II
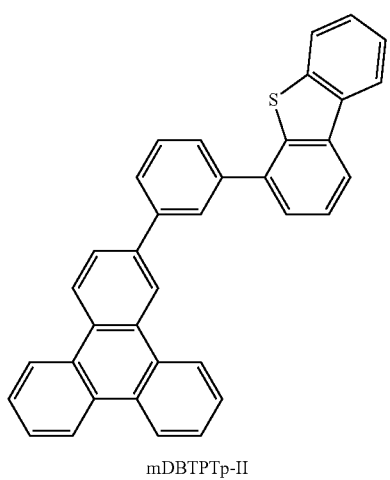
mDBTPTp-II
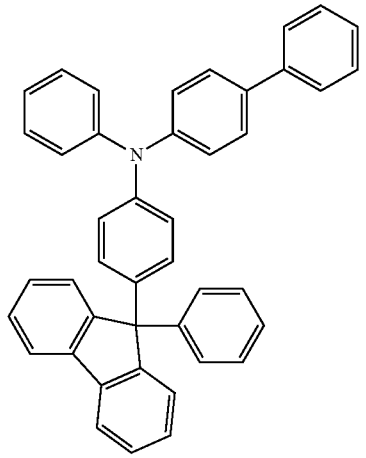
BPAFLP
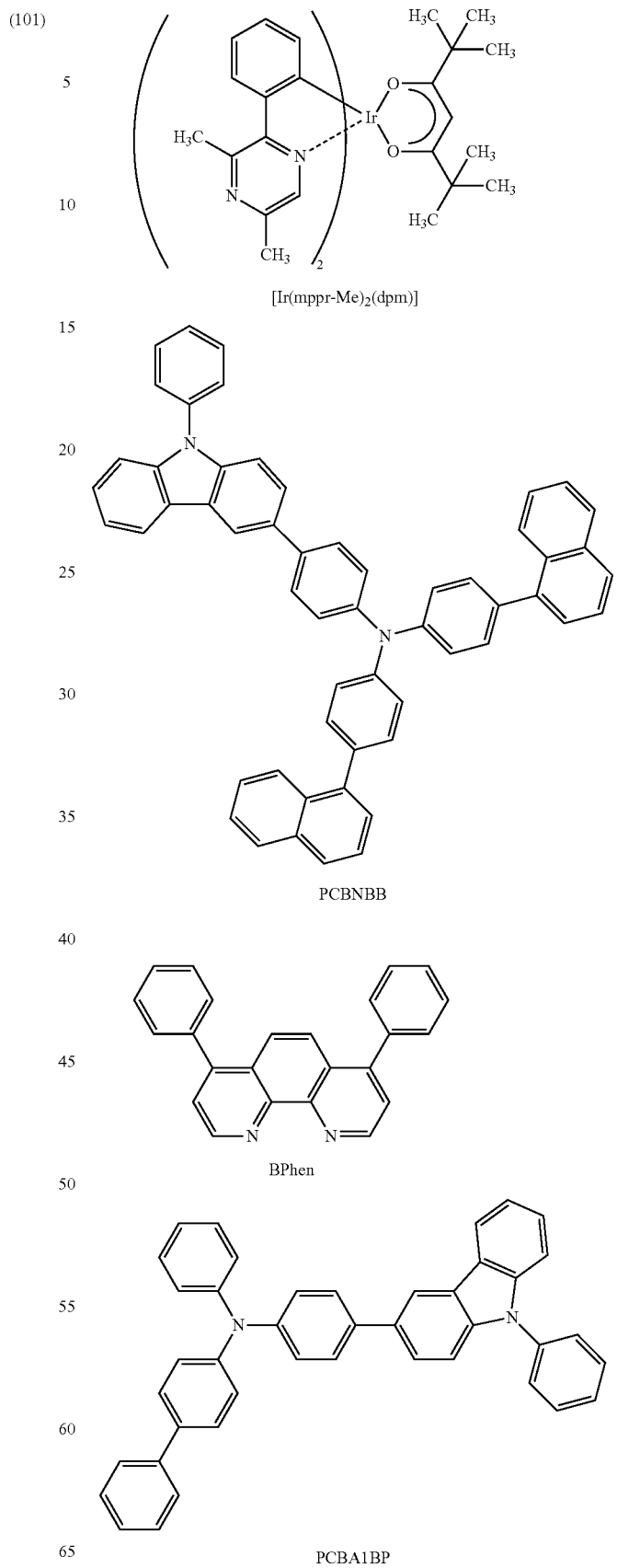
[Ir(mppr-Me)₂(dpm)]
PCBNBB
BPhen
PCBA1BP

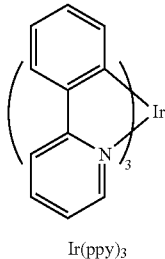

Ir(ppy)₃

The following shows methods of fabricating the light-emitting element 1, the comparative light-emitting element 2, and the light-emitting element 3 in this example.

(Light-Emitting Element 1)

First, over a substrate 1100, an indium oxide-tin oxide compound containing silicon or silicon oxide (ITO—SiO₂, hereinafter abbreviated to ITSO) was deposited by a sputtering method, so that a first electrode 1101 was formed. The composition ratio of a target used was In₂O₃:SnO₂:SiO₂=85:10:5 [wt %]. The thickness of the first electrode 1101 was 110 nm and the electrode area was 2 mm×2 mm. Here, the first electrode 1101 is an electrode that functions as an anode of the light-emitting element.

Next, as pretreatment for forming the light-emitting element over the substrate 1100, the surface of the substrate was washed, baked at 200° C. for one hour, and subjected to UV ozone treatment for 370 seconds.

After that, the substrate 1100 was transferred into a vacuum evaporation apparatus where the pressure had been reduced to approximately 10⁻⁴ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a substrate holder in a vacuum evaporation apparatus so that a surface of the substrate 1100 on which the first electrode 1101 was formed faced downward. The pressure in the vacuum evaporation apparatus was reduced to about 10⁻⁴ Pa. Then, by an evaporation method using resistance heating, 4-phenyl-4'-(9-phenylfluoren-9-yl)triphenylamine (abbreviation: BPAFLP) and molybdenum oxide were co-evaporated over the first electrode 1101, so that a hole-injection layer 1111 was formed. The thickness of the hole-injection layer 1111 was set to 40 nm, and the weight ratio of BPAFLP (abbreviation) to molybdenum oxide was adjusted to 4:2 (=BPAFLP:molybdenum oxide). Note that the co-evaporation method refers to an evaporation method in which evaporation is carried out from a plurality of evaporation sources at the same time in one treatment chamber.

Next, over the hole-injection layer 1111, a film of BPAFLP (abbreviation) was formed to a thickness of 20 nm, so that a hole-transport layer 1112 was formed.

Further, 2-[3-(dibenzothiophen-4-yl)phenyl]dibenzo[f,h]quinoline (abbreviation: 2mDBTPDBQu-II) synthesized in Example 1, 4,4'-di(1-naphthyl)-4''-(9-phenyl-9H-carbazol-3-yl)triphenylamine (abbreviation: PCBNBB), and bis(3,5-dimethyl-2-phenylpyrazinato)(dipivaloylmethanato)iridium(III) (abbreviation: [Ir(mppr-Me)₂(dpm)]) were co-evaporated, so that a light-emitting layer 1113 was formed over the hole-transport layer 1112. Here, the weight ratio of 2mDBTPDBQu-II (abbreviation) to PCBNBB (abbreviation) and [Ir(mppr-Me)₂(dpm)] (abbreviation) was adjusted to 0.8:0.2:0.05 (=2mDBTPDBQu-II:PCBNBB:[Ir(mppr-Me)₂(dpm)]). The thickness of the light-emitting layer 1113 was set to 40 nm.

Further, a 2mDBTPDBQu-II (abbreviation) film was deposited to a thickness of 10 nm over the light-emitting layer 1113, so that a first electron-transport layer 1114a was formed.

Then, a bathophenanthroline (abbreviation: BPhen) film was deposited to a thickness of 20 nm over the first electron-transport layer 1114a, so that a second electron-transport layer 1114b was formed.

Further, a lithium fluoride (LiF) film was formed to a thickness of 1 nm over the second electron-transport layer 1114b by evaporation, so that an electron-injection layer 1115 was formed.

Lastly, an aluminum film was formed to a thickness of 200 nm by evaporation, so that a second electrode 1103 functioning as a cathode was formed. Thus, the light-emitting element 1 in this example was fabricated.

Note that, in the above evaporation process, evaporation was all performed by a resistance heating method.

(Comparative Light-Emitting Element 2)

The light-emitting layer 1113 of the comparative light-emitting element 2, which corresponds to the light-emitting layer 1113 of the light-emitting element 1, was formed by co-evaporation of 4-[3-(triphenylene-2-yl)phenyl]dibenzothiophene (abbreviation: mDBTPTp-II), 4,4'-di(1-naphthyl)-4''-(9-phenyl-9H-carbazol-3-yl)triphenylamine (abbreviation: PCBNBB), and bis(3,5-dimethyl-2-phenylpyrazinato)(dipivaloylmethanato)iridium(III) (abbreviation: [Ir(mppr-Me)₂dpm]). The weight ratio of mDBTPTp-II (abbreviation) to PCBNBB (abbreviation) and [Ir(mppr-Me)₂(dpm)] (abbreviation) was adjusted to 0.8:0.2:0.05 (=mDBTPTp-II:PCBNBB:[Ir(mppr-Me)₂(dpm)]). The thickness of the light-emitting layer 1113 was set to 40 nm.

Further, the first electron-transport layer 1114a of the comparative light-emitting element 2, which corresponds to the first electron-transport layer 1114a of the light-emitting element 1, was formed by depositing mDBTPTp-II (abbreviation) to a thickness of 10 nm. The components other than the light-emitting layer 1113 and the first electron-transport layer 1114a were formed in the same manner as those of light-emitting element 1.

(Light-Emitting Element 3)

The light-emitting layer 1113 of the light-emitting element 3, which corresponds to the light-emitting layer 1113 of the light-emitting element 1, was formed by co-evaporation of 2-[3-(dibenzothiophen-4-yl)phenyl]dibenzo[f,h]quinoline (abbreviation: 2mDBTPDBQu-II), 4-phenyl-4'-(9-phenyl-9H-carbazol-3-yl)triphenylamine (abbreviation: PCBA1BP), and tris(2-phenylpyridinato-N,C²')iridium(III) (abbreviation: [Ir(ppy)₃]). The weight ratio of 2mDBTPDBQu-II (abbreviation) to PCBA1BP (abbreviation) and [Ir (ppy)₃] (abbreviation) was adjusted to 0.8:0.2:0.06 (=2mDBTPDBQu-II:PCBA1BP:[Ir(ppy)₃]). The thickness of the light-emitting layer 1113 was set to 30 nm.

The components of the light-emitting element 3 other than the light-emitting layer 1113 were formed in the same manner as those of light-emitting element 1.

Table 1 shows element structures of the light-emitting element 1, the comparative light-emitting element 2, and the light-emitting element 3 obtained as described above.

TABLE 1

| | First electrode | Hole-injection layer | Hole-transport layer | Light-emitting layer | First electron-transport layer | Second electron-transport layer | Electron-injection layer | Second Electrode | Note |
|---|---|---|---|---|---|---|---|---|---|
| Light-emitting element 1 | ITSO 110 nm | BPAFLP:MoOx (=4:2) 40 nm | BPAFLP 20 nm | 2mDBTPDBQu-II: PCBNBB: [Ir(mppr-Me)$_2$(dpm)] (=0.8:0.2:0.05) 40 nm | 2mDBTPDBQu-II 10 nm | BPhen 20 nm | LiF 1 nm | Al 200 nm | Orange element |
| Comparative light-emitting element 2 | ITSO 110 nm | BPAFLP:MoOx (=4:2) 40 nm | BPAFLP 20 nm | mDBTPTp-II: PCBNBB: [Ir(mppr-Me)$_2$(dpm)] (=0.8:0.2:0.05) 40 nm | mDBTPTp-II 10 nm | BPhen 20 nm | LiF 1 nm | Al 200 nm | Orange element |
| Light-emitting element 3 | ITSO 110 nm | BPAFLP:MoOx (=4:2) 40 nm | BPAFLP 20 nm | 2mDBTPDBQu-II: PCBA1BP: [Ir(ppy)$_3$] (=0.8:0.2:0.06) 30 nm | 2mDBTPDBQu-II 10 nm | BPhen 20 nm | LiF 1 nm | Al 200 nm | Green element |

The light-emitting element 1, the comparative light-emitting element 2, and the light-emitting element 3 were sealed with a glass substrate in a glove box containing a nitrogen atmosphere so as not to be exposed to the air (a sealant was applied onto an outer edge of each element and heat treatment was performed at 80° C. for 1 hour at the time of sealing). Then, the operating characteristics of these light-emitting elements were measured. Note that the measurement was carried out at room temperature (in an atmosphere kept at 25° C.).

Figure 13:
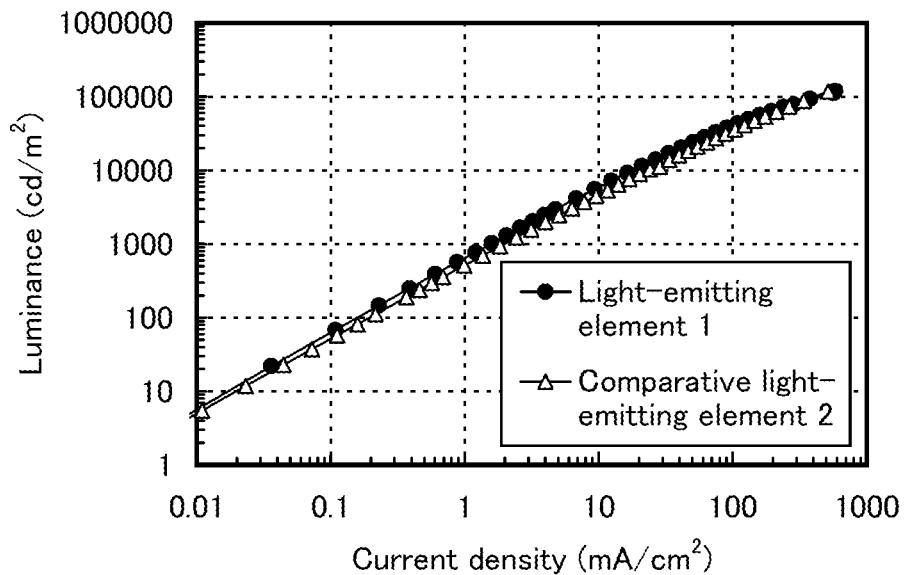
FIG. 13 shows current density-luminance characteristics of a light-emitting element 1 and a comparative light-emitting element 2.
Figure 14:
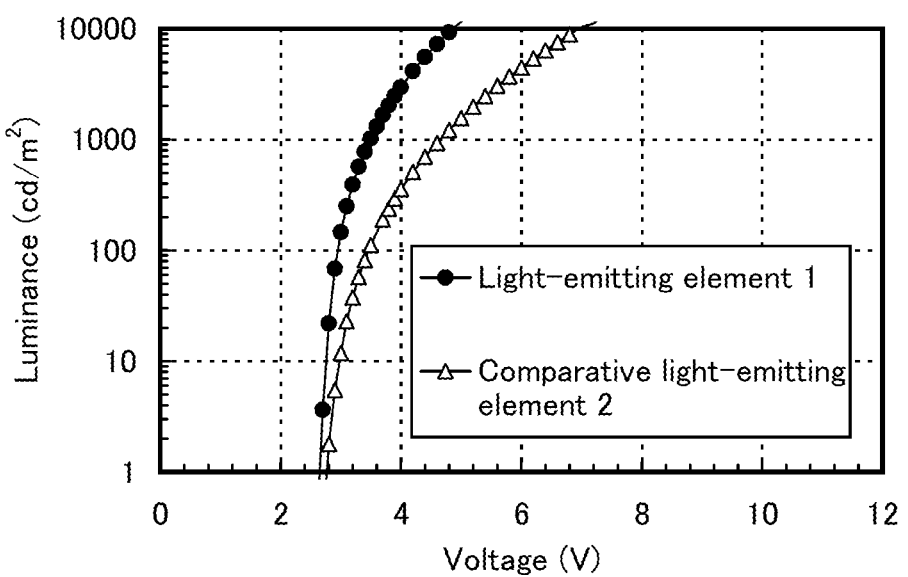
FIG. 14 shows voltage-luminance characteristics of the light-emitting element 1 and the comparative light-emitting element 2.
Figure 15:
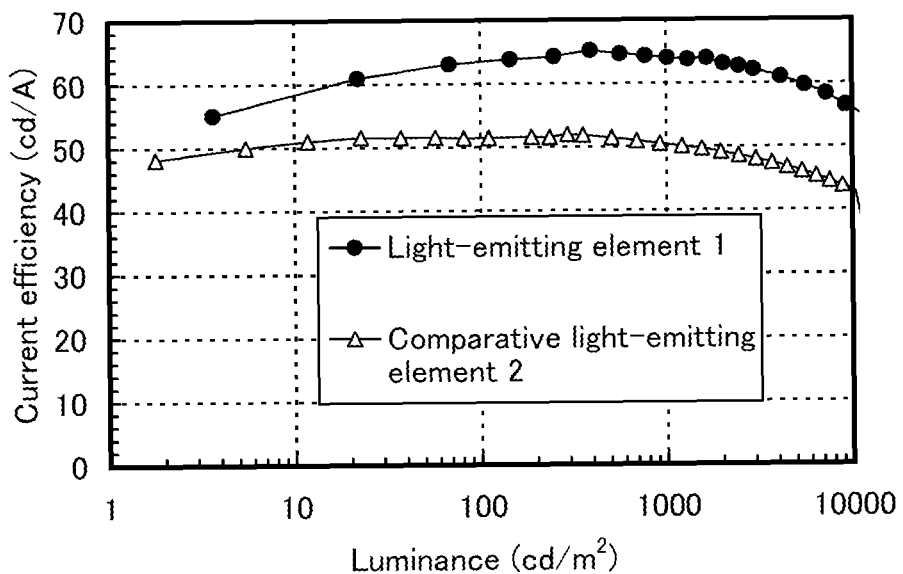
FIG. 15 shows luminance-current efficiency characteristics of the light-emitting element 1 and the comparative light-emitting element 2.
Figure 16:
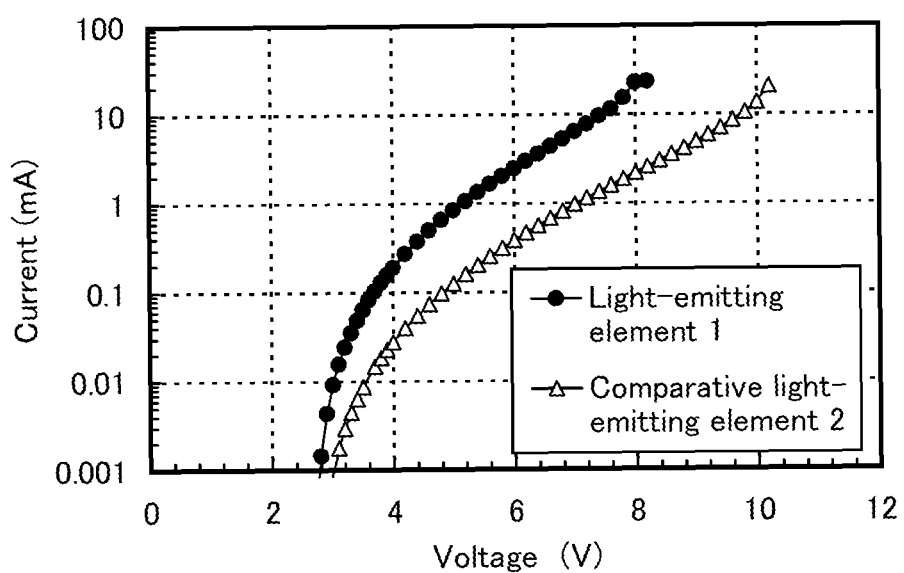
FIG. 16 shows voltage-current characteristics of the light-emitting element 1 and the comparative light-emitting element 2.

FIG. 13 shows current density-luminance characteristics of the light-emitting element 1 and the comparative light-emitting element 2. In FIG. 13, the horizontal axis represents current density (mA/cm$^2$), and the vertical axis represents luminance (cd/m$^2$). FIG. 14 shows voltage-luminance characteristics of the light-emitting element 1 and the comparative light-emitting element 2. In FIG. 14, the horizontal axis represents voltage (V) and the vertical axis represents luminance (cd/m$^2$). FIG. 15 shows luminance-current efficiency characteristics of the light-emitting element 1 and the comparative light-emitting element 2. In FIG. 15, the horizontal axis represents luminance (cd/m$^2$), and the vertical axis represents current efficiency (cd/A). FIG. 16 shows voltage-current characteristics of the light-emitting element 1 and the comparative light-emitting element 2. In FIG. 16, the horizontal axis represents voltage (V) and the vertical axis represents current (mA).

Figure 17:
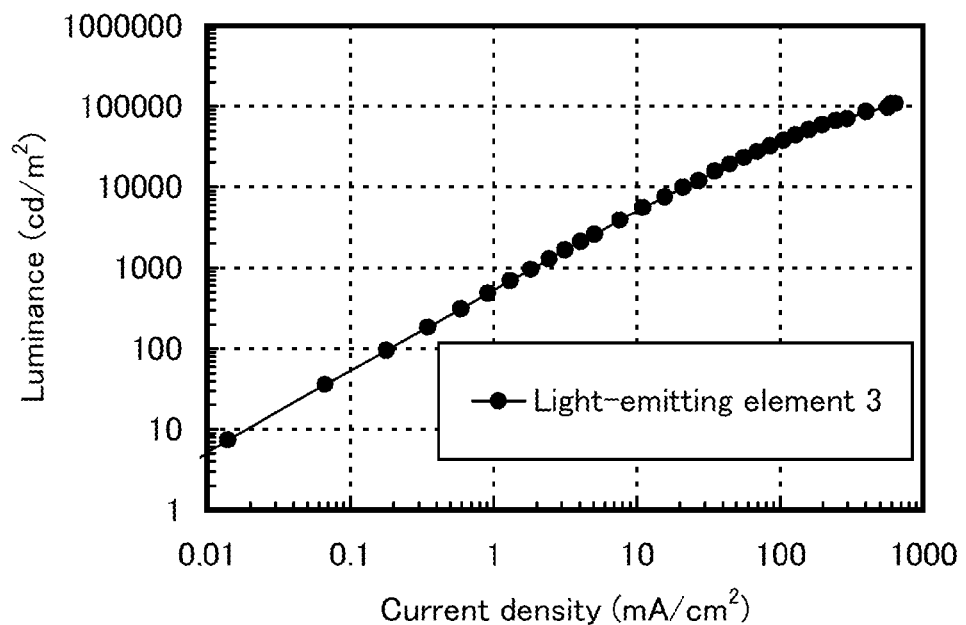
FIG. 17 shows current density-luminance characteristics of a light-emitting element 3.
Figure 18:
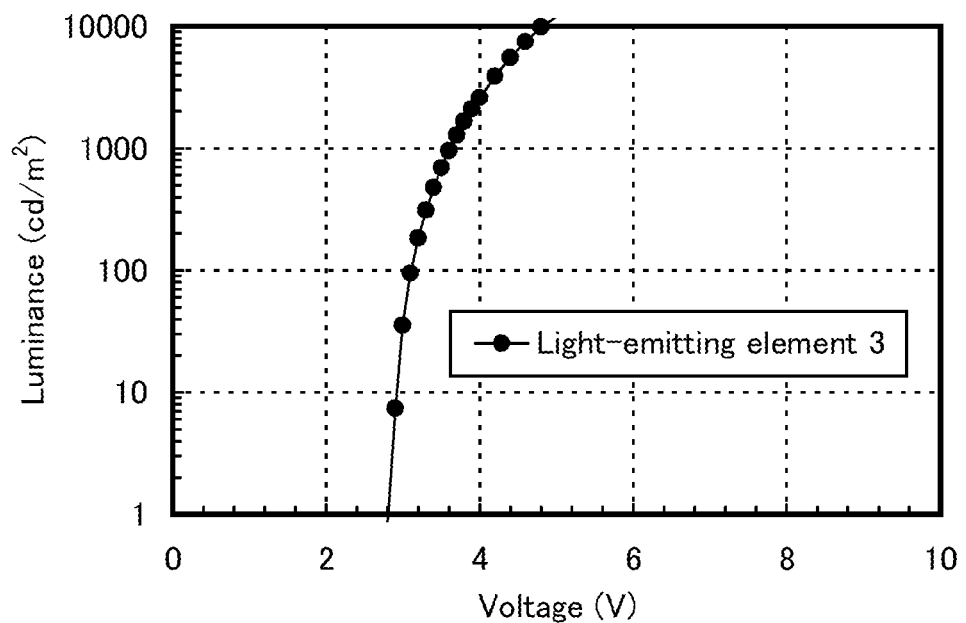
FIG. 18 shows voltage-luminance characteristics of the light-emitting element 3.
Figure 19:
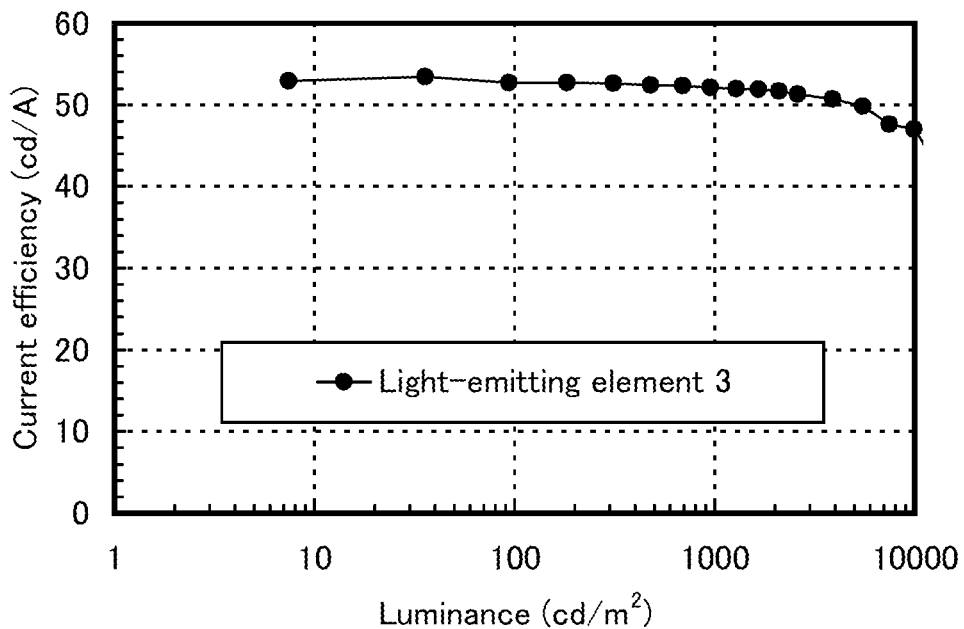
FIG. 19 shows luminance-current efficiency characteristics of the light-emitting element 3.
Figure 20:
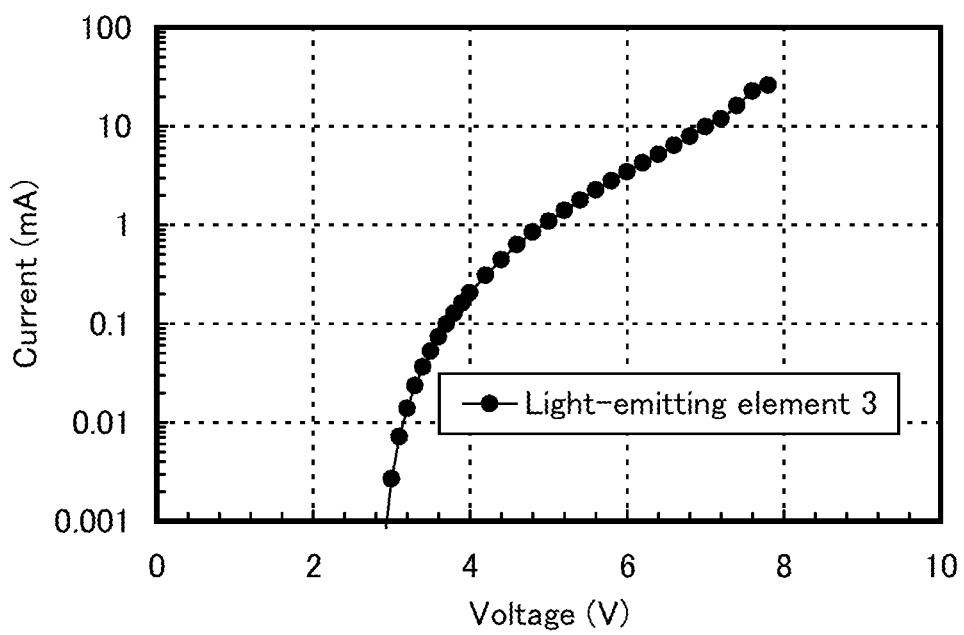
FIG. 20 shows voltage-current characteristics of the light-emitting element 3.

FIG. 17 shows current density-luminance characteristics of the light-emitting element 3. In FIG. 17, the horizontal axis represents current density (mA/cm$^2$), and the vertical axis represents luminance (cd/m$^2$). FIG. 18 shows voltage-luminance characteristics of the light-emitting element 3. In FIG. 18, the horizontal axis represents voltage (V), and the vertical axis represents luminance (cd/m$^2$). FIG. 19 shows luminance-current efficiency characteristics of the light-emitting element 3. In FIG. 19, the horizontal axis represents luminance (cd/m$^2$) and the vertical axis represents current efficiency (cd/A). FIG. 20 shows voltage-current characteristics of the light-emitting element 3. In FIG. 20, the horizontal axis represents voltage (V) and the vertical axis represents current (mA).

Further, Table 2 shows the voltage (V), current density (mA/cm$^2$), CIE chromaticity coordinates (x, y), current efficiency (cd/A), and external quantum efficiency (%) of each light-emitting element at a luminance of around 1000 cd/m$^2$.

TABLE 2

| | Voltage (V) | Current density (mA/cm$^2$) | Chromaticity (x, y) | | Luminance (cd/m$^2$) | Current efficiency (cd/A) | External quantum efficiency (%) |
|---|---|---|---|---|---|---|---|
| Light-emitting element 1 | 3.5 | 1.6 | 0.54 | 0.46 | 1020 | 64 | 24 |
| Comparative light-emitting element 2 | 4.6 | 1.8 | 0.53 | 0.46 | 930 | 50 | 19 |
| Light-emitting element 3 | 3.6 | 1.8 | 0.34 | 0.61 | 950 | 52 | 15 |

As shown in Table 2, the CIE chromaticity coordinates (x, y) of the light-emitting element 1 were (0.54, 0.46) at a luminance of 1020 cd/m$^2$. The CIE chromaticity coordinates (x, y) of the comparative light-emitting element 2 were (0.53, 0.46) at a luminance of 930 cd/m$^2$. The CIE chromaticity coordinates (x, y) of the light-emitting element 3 were (0.34, 0.61) at a luminance of 950 cd/m$^2$.

From Table 2, it is found that current efficiencies of the light-emitting element 1 at a luminance of 1020 cd/m$^2$, of the comparative light-emitting element 2 at a luminance of 930 cd/m$^2$, and of the light-emitting element 3 at a luminance of 950 cd/m$^2$ were 64 cd/A, 50 cd/A, and 52 cd/A, respectively. Further, external quantum efficiencies of the light-emitting element 1 at a luminance of 1020 cd/m$^2$, of the comparative light-emitting element 2 at a luminance of 930 cd/m$^2$, and of the light-emitting element 3 at a luminance of 950 cd/m$^2$ were 24%, 19%, and 15%, respectively.

FIGS. 14 to 16 show that voltage-luminance characteristics, luminance-current efficiency characteristics, and voltage-current characteristics differ between the light-emitting element 1 according to one embodiment of the present invention and the comparative light-emitting element 2. It is found that the light-emitting element 1 is driven at a lower voltage and has higher current efficiency than the comparative light-emitting element 2. A structural difference between the compounds used as host materials in light-emitting layers is that the light-emitting element 1 includes a dibenzo[f,h]quinoline skeleton while the comparative light-emitting element 2 includes a triphenylene skeleton. It is thus confirmed that a compound having a dibenzo[f,h]quinoline skeleton, such as the heterocyclic compound according to one embodiment of the present invention, is highly effective in voltage-luminance characteristics, luminance-current efficiency characteristics, and voltage-current characteristics.

From Table 2, it is also found that the light-emitting element 1 has higher current efficiency and external quantum efficiency than the comparative light-emitting element 2. It is thus confirmed that a compound having a dibenzo[f,h]quinoline skeleton, such as the heterocyclic compound according to one embodiment of the present invention, is effective in achieving high current efficiency and high external quantum efficiency.

Reference Example 1

A method of synthesizing 4-phenyl-4'-(9-phenylfluoren-9-yl)triphenylamine (abbreviation: BPAFLP) used in Example 2 above will be specifically described. A structure of BPAFLP is shown below.

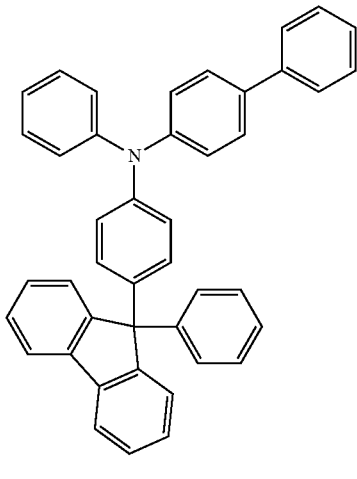

BPAFLP

Step 1: Method of synthesizing 9-(4-bromophenyl)-9-phenylfluorene

In a 100-mL three-neck flask, 1.2 g (50 mmol) of magnesium was heated and stirred under reduced pressure for 30 minutes to be activated. After the flask was cooled to room temperature and was made to have a nitrogen atmosphere, several drops of dibromoethane were added, so that foam formation and heat generation were confirmed. After 12 g (50 mmol) of 2-bromobiphenyl dissolved in 10 mL of diethyl ether was slowly dropped into this mixture, the mixture was heated and stirred under reflux for 2.5 hours and made into a Grignard reagent.

In a 500-mL three-neck flask, 10 g (40 mmol) of 4-bromobenzophenone and 100 mL of diethyl ether were put. After the Grignard reagent which was synthesized in advance was slowly dropped into this mixture, the mixture was stirred and heated under reflux for 9 hours.

After the reaction, this mixture was filtered to obtain a residue. The residue was dissolved in 150 mL of ethyl acetate, and hydrochloric acid was added to the mixture, and the mixture was stirred for 2 hours. An organic layer of this liquid was washed with water. Then, magnesium sulfate was added to remove moisture. This suspension was filtered, and the obtained filtrate was concentrated to give a highly viscous oily substance.

In a 500-mL recovery flask, this highly viscous oily substance, 50 mL of glacial acetic acid, and 1.0 mL of hydrochloric acid were put. The mixture was heated and stirred under a nitrogen atmosphere at 130° C. for 1.5 hours to be reacted.

After the reaction, this reaction mixture solution was filtered to give a residue. The residue was washed with water, an aqueous solution of sodium hydroxide, water, and methanol in this order, and then dried, so that 11 g of white powder of the object of the synthesis was obtained in 69% yield. The reaction scheme of the synthesis method is illustrated in the following (D-1).

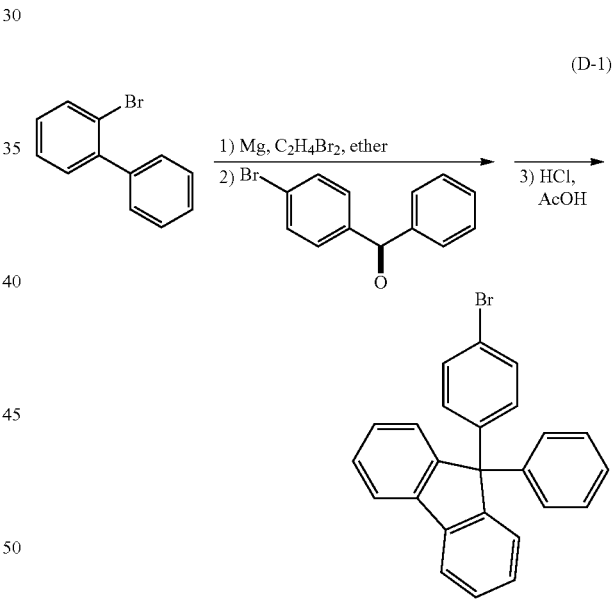

(D-1)

Step 2: Method of synthesizing 4-phenyl-4'-(9-phenylfluoren-9-yl)triphenylamine (abbreviation: BPAFLP)

In a 100-mL three-neck flask, 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0) were put, and the air in the flask was replaced with nitrogen. Then, 20 mL of dehydrated xylene was added to this mixture. After the mixture was deaerated while being stirred under reduced pressure, 0.2 mL (0.1 mmol) of tri(tert-butyl)phosphine (10 wt % hexane solution) was added thereto. This mixture was heated and stirred at 110° C. for 2 hours in a nitrogen atmosphere to be reacted.

After the reaction, 200 mL of toluene was added to the reaction mixture solution, and this suspension was filtered through Florisil (produced by Wako Pure Chemical Industries, Ltd., Catalog No. 540-00135) and Celite (produced by Wako Pure Chemical Industries, Ltd., Catalog No. 531-16855). The filtrate was concentrated, and the resulting substance was purified by silica gel column chromatography (a developing solvent of toluene and hexane in a ratio of 1:4 was used). The obtained fraction was concentrated, and acetone and methanol were added thereto. The mixture was irradiated with ultrasonic wave and then recrystallized to obtain 4.1 g of white powder of the object of the synthesis in 92% yield. The reaction scheme of the synthesis method is illustrated in the following (D-2).

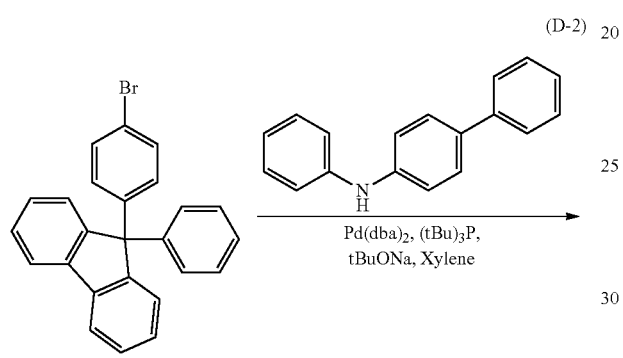

An Rf value of the object of the synthesis by a silica gel thin layer chromatography (TLC) (a developing solvent of ethyl acetate and hexane in a ratio of 1:10 was used) was 0.41, that of 9-(4-bromophenyl)-9-phenylfluorene was 0.51, and that of 4-phenyl-diphenylamine was 0.27.

A compound obtained through the above Step 2 was measured by a nuclear magnetic resonance method ($^1$H NMR). The measurement data are shown below. The measurement results indicate that the obtained compound was BPAFLP (abbreviation), which is a fluorene derivative.

$^1$H NMR data of the obtained substance are as follows:

$^1$H NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, J=6.9, 2H).

Reference Example 2

A method of synthesizing 4-phenyl-4'-(9-phenyl-9H-carbazol-3-yl)triphenylamine (abbreviation: PCBA1BP) used in Example 2 will be specifically described. A structure of PCBA1BP is shown below.

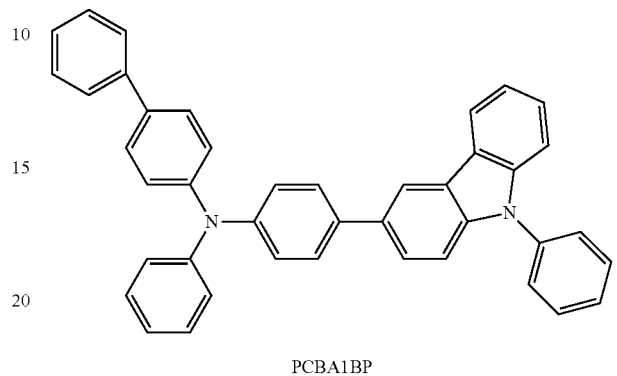

PCBA1BP

Step 1: Synthesis of 4-bromodiphenylamine

A synthesis scheme of 4-bromodiphenylamine in Step 1 is shown in the following (E-1).

In a 1-L conical flask, 51 g (0.3 mol) of diphenylamine was dissolved in 700 mL of ethyl acetate, and then 54 g (0.3 mol) of N-bromosuccinimide (abbreviation: NBS) was added to this solution. About 300 hours later, this mixture solution was washed with water, and then magnesium sulfate was added thereto to remove moisture. This mixture solution was filtered, and the filtrate was concentrated and collected. The object of the synthesis was obtained as 70 g of a dark brown oily substance in 94% yield.

Step 2-1: Synthesis of 3-bromo-9-phenyl-9H-carbazole

A synthesis scheme of 3-bromo-9-phenyl-9H-carbazole in Step 2-1 is shown in the following (E-2-1).

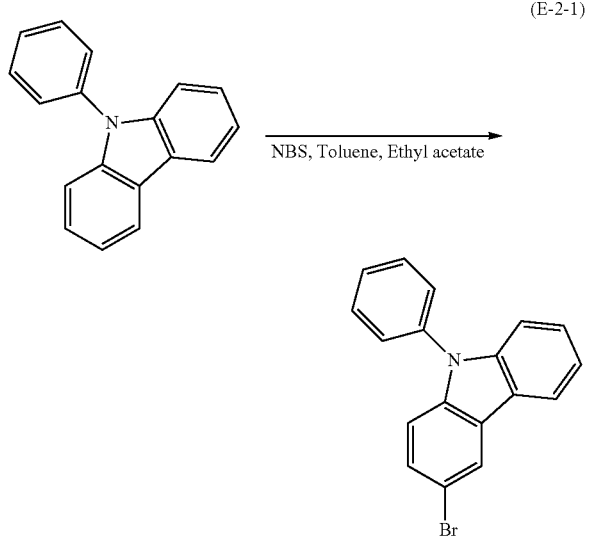

(E-2-1)

In a 1-L conical flask, 24 g (100 mmol) of 9-phenyl-9H-carbazole, 18 g (100 mmol) of N-bromosuccinimide, 450 mL of toluene, and 200 mL of ethyl acetate were stirred at room temperature for 45 hours. This suspension was washed with water, and then magnesium sulfate was added thereto to remove moisture. This suspension was filtered, and the obtained filtrate was concentrated and dried. The objective substance was obtained as 32 g of a highly viscous oily substance in 99% yield.

Step 2-2: Synthesis of
9-phenyl-9H-carbazol-3-boronic acid

A synthesis scheme of 9-phenyl-9H-carbazol-3-boronic acid in Step 2-2 is shown in the following (E-2-2).

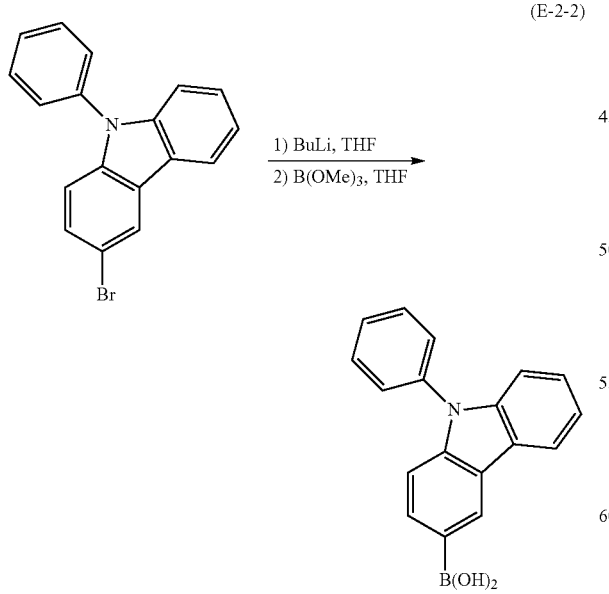

(E-2-2)

In a 500-mL conical flask, 29 g (90 mmol) of 3-bromo-9-phenyl-9H-carbazole and 200 mL of tetrahydrofuran (abbreviation: THF) were stirred at −78° C. to obtain a solution. After that, 110 mL (69 mmol) of n-butyllithium (1.57 mol/L hexane solution) was dripped into this solution. The mixture was stirred at the same temperature for 2 hours. Furthermore, 13 mL (140 mmol) of trimethyl borate was added to the mixture, and the mixture was stirred at room temperature for 24 hours.

After the reaction, 200 mL of 1.0 mol/L hydrochloric acid was added to the mixture, and the mixture was stirred at room temperature for 1 hour. This mixture was washed with water, an aqueous solution of sodium hydroxide, and water in this order, and magnesium sulfate was added thereto to remove moisture. This suspension was filtered, and the obtained filtrate was concentrated and chloroform and hexane were added thereto. The mixture was irradiated with ultrasonic waves and then recrystallized. Then, the object of the synthesis was obtained as 21 g of white powder in 80% yield.

Step 3: Synthesis of
4-(9-phenyl-9H-carbazol-3-yl)diphenylamine
(abbreviation: PCBA)

A synthesis scheme of 4-(9-phenyl-9H-carbazol-3-yl)diphenylamine (abbreviation: PCBA) in Step 3 is shown in the following (E-3).

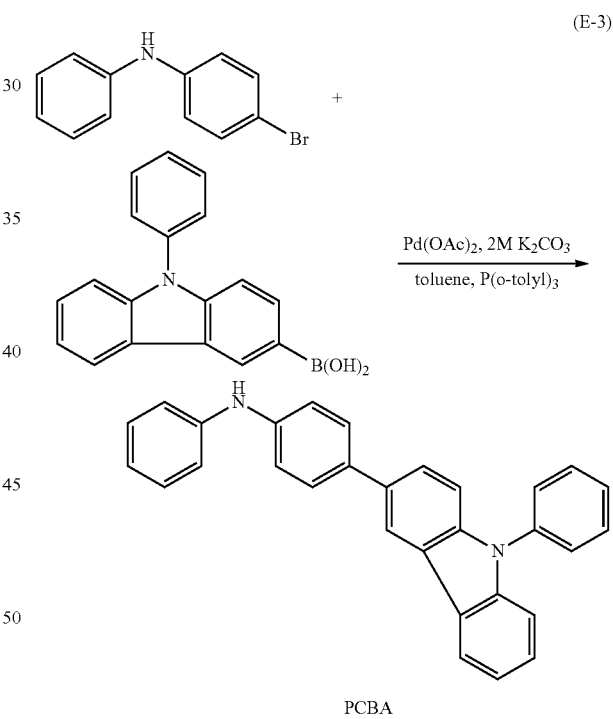

(E-3)

PCBA

Into a 500-mL three-neck flask, 6.5 g (26 mmol) of 4-bromo-diphenylamine, 7.5 g (26 mmol) of 9-phenyl-9H-carbazole-3-boronic acid, and 400 mg (1.3 mmol) of tri(o-tolyl)phosphine were put, and the air in the flask was replaced with nitrogen. To the mixture, 100 mL of toluene, 50 mL of ethanol, and 14 mL (0.2 mol/L) of an aqueous solution of potassium carbonate were added. Under reduced pressure, this mixture was degassed while being stirred. After the degassing, 67 mg (30 mmol) of palladium(II) acetate were added to the mixture.

This mixture was refluxed at 100° C. for 10 hours. After the reflux, an aqueous layer of the mixture was extracted with toluene, and the extract was combined with an organic layer and then washed with a saturated solution of sodium chloride. After magnesium sulfate was added to remove moisture of the organic layer, this mixture was gravity filtered. The obtained filtrate was concentrated to give a pale brown oily substance. The oily substance was purified by silica gel column chromatography (a developing solvent of hexane and toluene in a ratio of 4:6 was used), and a white solid obtained after the purification was recrystallized with a mixed solvent of dichloromethane and hexane to give a white solid which was the object of the synthesis. The yield was 4.9 g and 45%.

Step 4: Synthesis of 4-phenyl-4'-(9-phenyl-9H-carbazol-3-yl)triphenylamine (abbreviation: PCBA1BP)

A synthesis scheme of 4-phenyl-4'-(9-phenyl-9H-carbazol-3-yl)triphenylamine (abbreviation: PCBA1BP) in Step 4 is shown in the following (E-4).

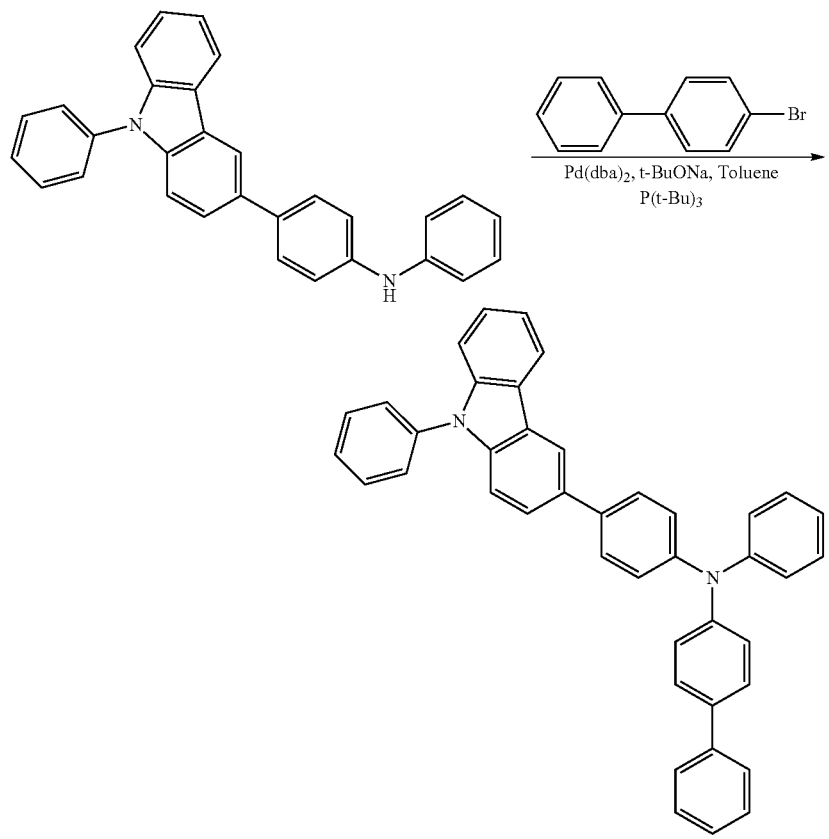

(E-4)

In a 100-mL three-neck flask, 2.0 g (4.9 mmol) of 4-(9-phenyl-9H-carbazol-3-yl)diphenylamine, 1.1 g (4.9 mmol) of 4-bromobiphenyl, and 2.0 g (20 mmol) of sodium tert-butoxide were put, and the air in the flask was replaced with nitrogen. Then, 50 mL of toluene and 0.30 mL of tri(tert-butyl)phosphine (10 wt % hexane solution) were added to this mixture.

This mixture was deaerated while being stirred under low pressure. After the deaeration, 0.10 g of bis(dibenzylideneacetone)palladium(0) was added to the mixture. Next, this mixture was stirred at 80° C. for 5 hours to be reacted. After the reaction, toluene was added to this reaction mixture. This suspension was suction filtered through Celite (produced by Wako Pure Chemical Industries, Ltd., Catalog No. 531-16855), alumina, and Florisil (produced by Wako Pure Chemical Industries, Ltd., Catalog No. 540-00135), and thus the filtrate was obtained. The resulting filtrate was washed with a saturated aqueous solution of sodium carbonate and a saturated solution of sodium chloride in this order. The organic layer was dried by addition of magnesium sulfate thereto. After the drying, this mixture was suction filtered to remove the magnesium sulfate, and thus the filtrate was obtained.

The resulting filtrate was concentrated, followed by purification using silica gel column chromatography. The silica gel column chromatography was performed by, first, using a mixed solvent of toluene and hexane in a ratio of 1:9 as a developing solvent, and then using a mixed solvent of toluene and hexane in a ratio of 3:7 as another developing solvent. A solid which was obtained by concentrating the obtained fraction was recrystallized with a mixed solvent of chloroform and hexane to obtain 2.3 g of a white powder-like solid in 84% yield.

Sublimation purification of 1.2 g of the white solid was performed by a train sublimation method. The sublimation purification was performed under a reduced pressure of 7.0 Pa, with a flow rate of argon at 3 mL/min, at 280° C. for 20 hours. The yield was 1.1 g and 89%.

A compound obtained through the above Step 4 was measured by a nuclear magnetic resonance method ($^1$H NMR). The measurement data are shown below. The measurement results indicate that 4-phenyl-4'-(9-phenyl-9H-carbazol-3-yl)triphenylamine (abbreviation: PCBA1BP) was obtained.

¹H NMR data of the obtained substance are as follows:

¹H NMR (DMSO-d₆, 300 MHz): δ (ppm)=7.05-7.20 (m, 7H), 7.28-7.78 (m, 21H), 8.34 (d, J=7.8 Hz, 1H), 8.57 (s, 1H).

Example 3

This example will show a method of synthesizing 2-{3-[3-(dibenzothiophen-4-yl)phenyl]phenyl}dibenzo[f,h]quinoline (abbreviation: 2mDBTBPDBQu-II) represented by the following structural formula (109).

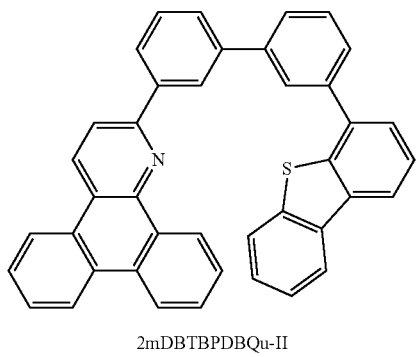

2mDBTBPDBQu-II

Synthesis of 2-{3-[3-(dibenzothiophen-4-yl)phenyl]phenyl}dibenzo[f,h]quinoline (abbreviation: 2mDBTBPDBQu-II)

A synthesis scheme of 2-{3-[3-(dibenzothiophen-4-yl)phenyl]phenyl}dibenzo[f,h]quinoline (abbreviation: 2mDBTBPDBQu-II) is shown in (F-1).

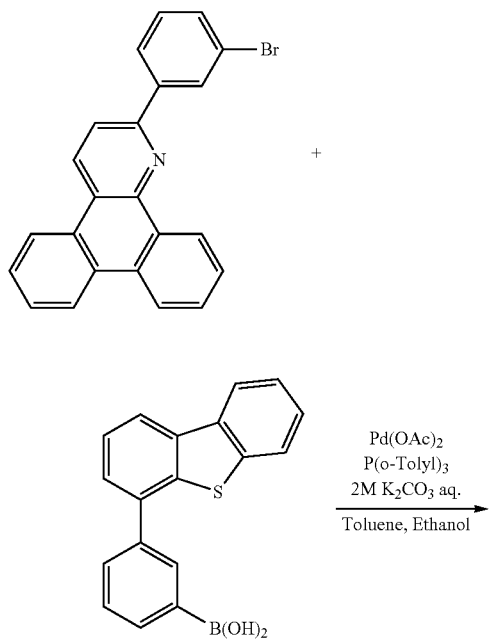

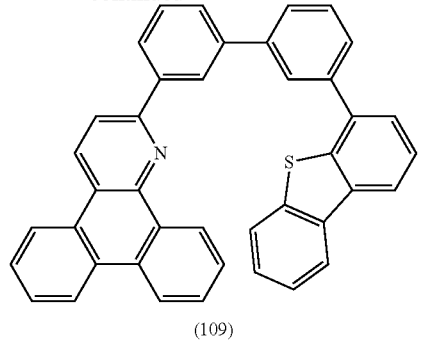

(109)

In a 50-mL three-neck flask, 0.56 g (1.5 mmol) of 2-(3-bromophenyl)dibenzo[f,h]quinoline, 0.46 g (1.5 mmol) of 3-(dibenzothiophen-4-yl)phenylboronic acid, 58 mg (0.19 mmol) of tri(ortho-tolyl)phosphine, 15 mL of toluene, 1.5 mL of ethanol, and 1.5 mL of a 2M aqueous solution of potassium carbonate were put. The mixture was degassed by being stirred under reduced pressure, and the air in the flask was replaced with nitrogen. Then, 17 mg (77 μmol) of palladium (II) acetate was added to this mixture, and the mixture was stirred at 80° C. for 9 hours under a nitrogen stream. After a predetermined time, water and toluene were added to this mixture, and the resulting solid was collected by suction filtration. A toluene solution of the obtained solid was suction-filtered through alumina and Celite, and the filtrate was concentrated to give a yellow solid. A methanol suspension of the obtained solid was irradiated with ultrasonic waves, and a solid was collected by suction filtration, so that the object of the synthesis was obtained as 0.52 g of white powder in 63% yield.

Then, 0.53 g of the obtained white powder of 2-{3-[3-(dibenzothiophen-4-yl)phenyl]phenyl}dibenzo[f,h]quinoline was purified by a train sublimation method. The purification was performed under such conditions that the pressure was 3.2 Pa, the argon flow rate was 5.0 mL/min, so that 2-{3-[3-(dibenzothiophen-4-yl)phenyl]phenyl}dibenzo[f,h]quinoline was heated at 280° C. for 15 hours. After the purification, 0.43 g of a white powder of 2-{3-[3-(dibenzothiophen-4-yl)phenyl]phenyl}dibenzo[f,h]quinoline was obtained in 80% yield.

A nuclear magnetic resonance (¹H NMR) method identified this compound as 2-{3-[3-(dibenzothiophen-4-yl)phenyl]phenyl}dibenzo[f,h]quinoline (abbreviation: 2mDBTBPDBQu-II), which was the object of the synthesis.

¹H NMR data of the obtained substance are as follows:

¹H NMR (CDCl₃, 300 MHz): δ=7.43-7.51 (m, 2H), 7.60-7.85 (m, 12H), 8.13 (d, J=8.7 Hz, 1H), 8.18-8.23 (m, 3H), 8.35 (d, J=7.8 Hz, 1H), 8.59-8.71 (m, 4H), 8.94 (d, J=8.7 Hz, 1H), 9.58 (dd, J=1.5 Hz, 8.4 Hz, 1H).

Figure 21A:
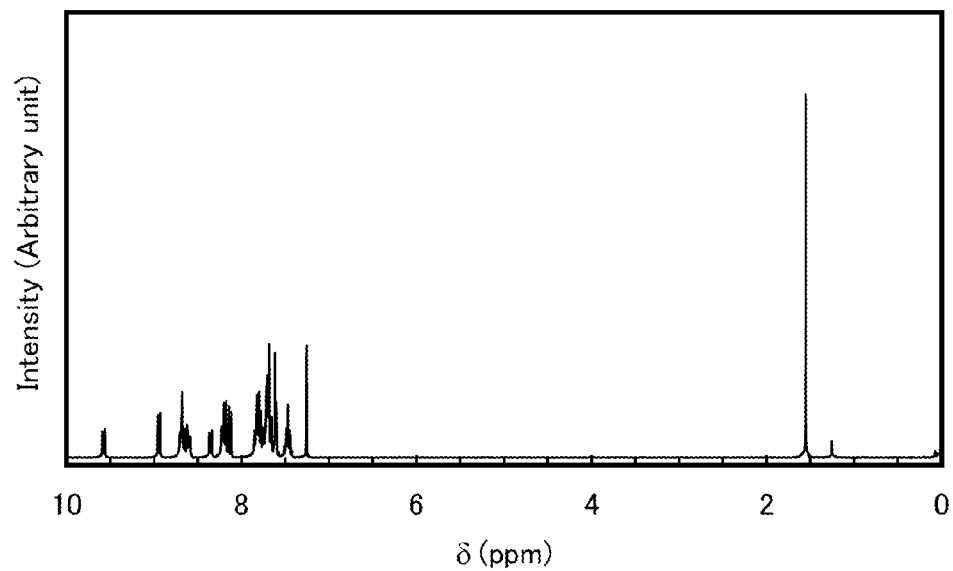
FIGS. 21A and 21B show $^1$H NMR charts of 2-{3-[3-(dibenzothiophen-4-yl)phenyl]phenyl}dibenzo[f,h]quinoline.
Figure 21B:
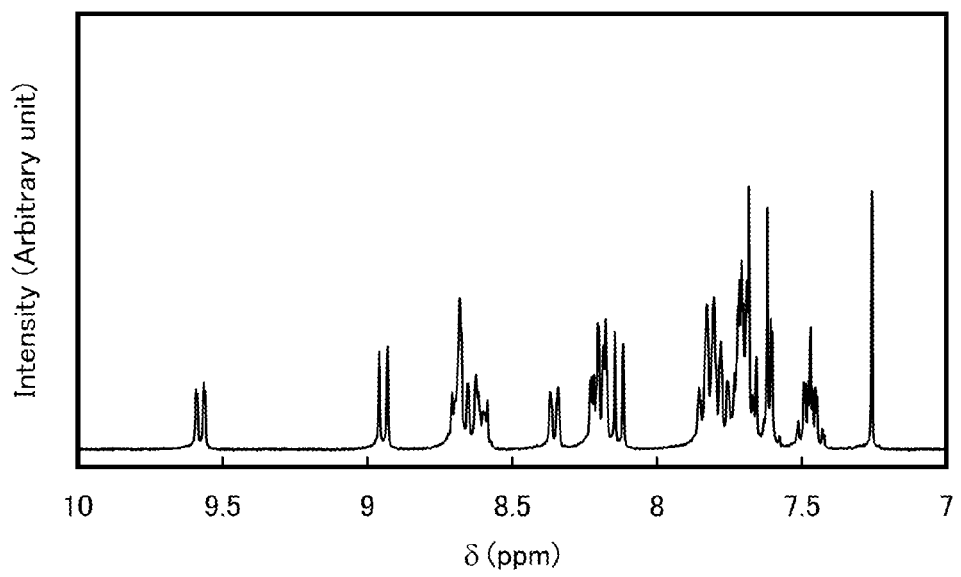

¹H NMR charts are shown in FIGS. 21A and 21B. Note that FIG. 21B shows an enlarged chart showing the range from 7.0 ppm to 10.0 ppm in FIG. 21A.

Figure 22A:
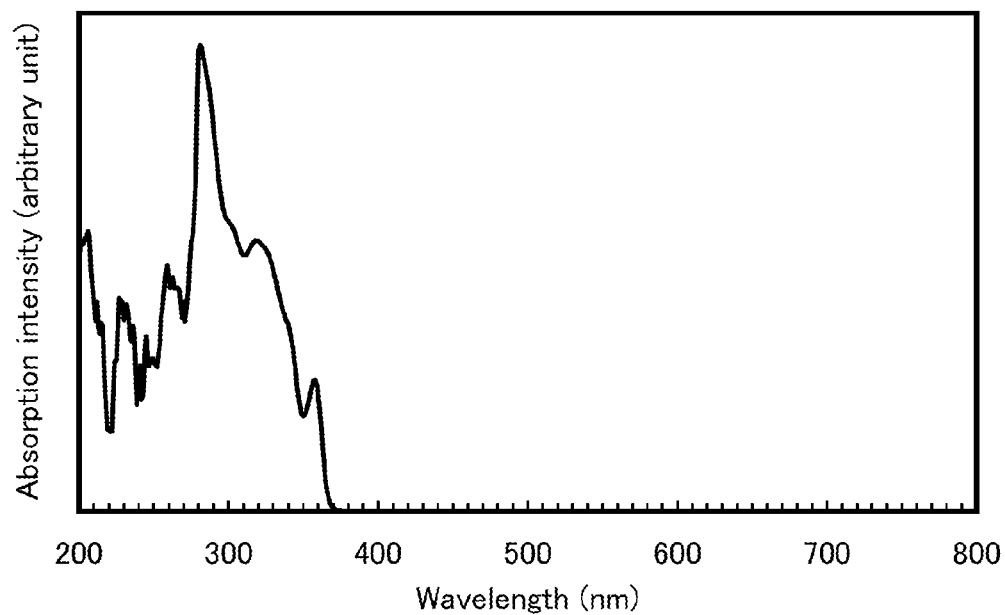
FIGS. 22A and 22B show absorption and emission spectra of a toluene solution of 2-{3-[3-(dibenzothiophen-4-yl)phenyl]phenyl}dibenzo[f,h]quinoline.
Figure 22B:
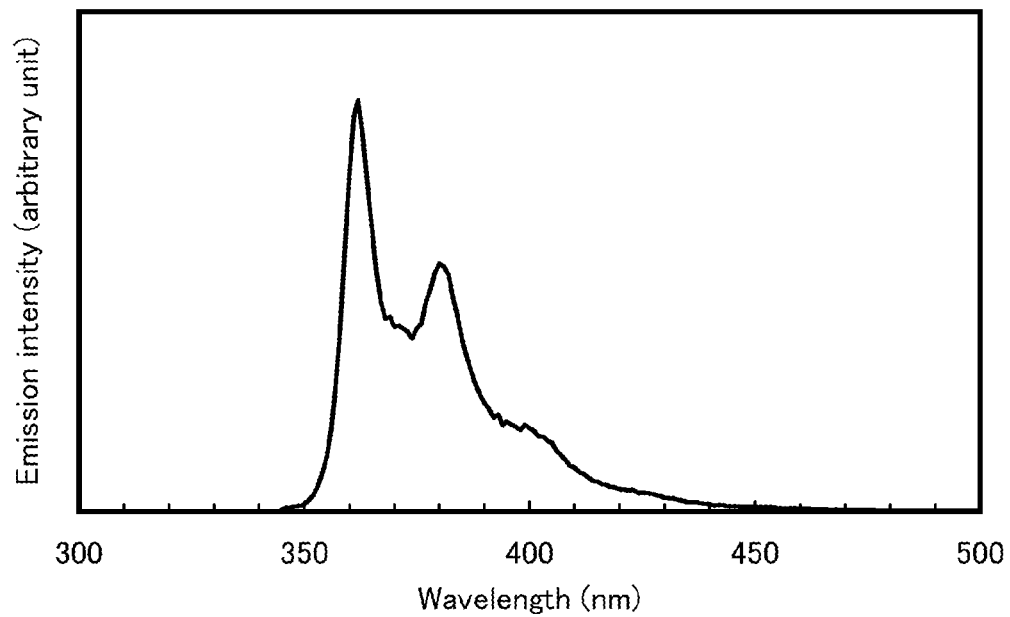
Figure 23A:
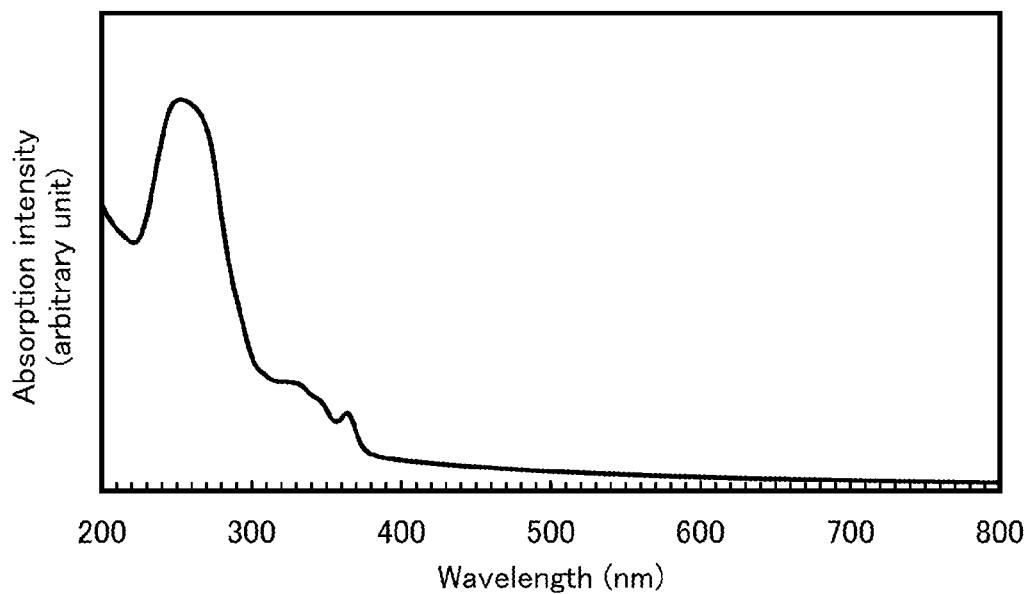
FIGS. 23A and 23B show absorption and emission spectra of a thin film of 2-{3-[3-(dibenzothiophen-4-yl)phenyl]phenyl}dibenzo[f,h]quinoline.
Figure 23B:
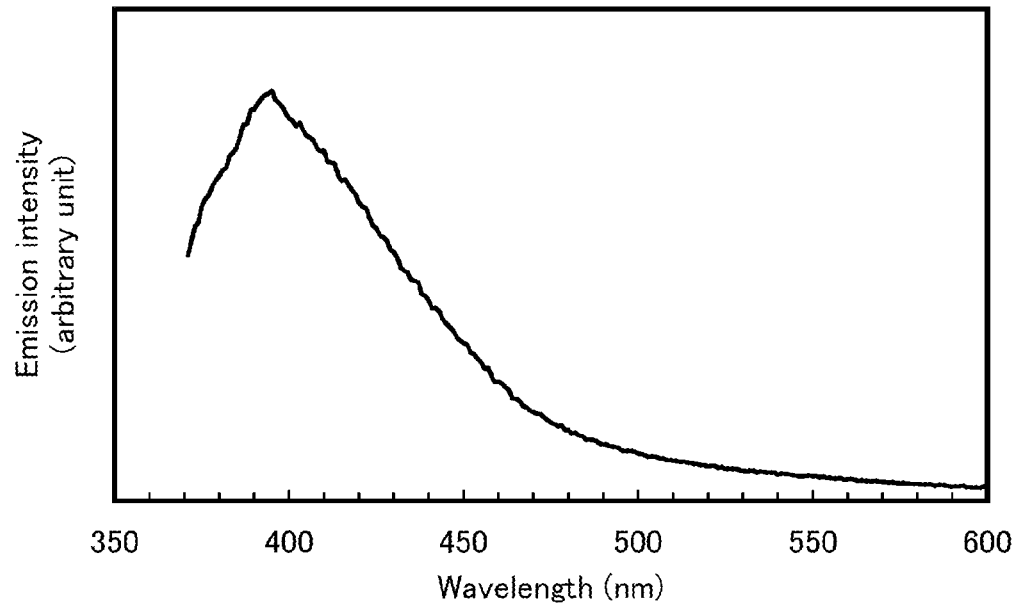

Further, FIG. 22A shows an absorption spectrum of a toluene solution of 2mDBTBPDBQu-II (abbreviation), and FIG. 22B shows an emission spectrum thereof. FIG. 23A shows an absorption spectrum of a thin film of 2mDBTBPDBQu-II, and FIG. 23B shows an emission spectrum thereof. The measurement of the absorption spectrum was conducted by using a UV-visible spectrophotometer (V-550, manufactured by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 22A and 22B and FIGS. 23A and 23B, the horizontal axis represents wavelength (nm) and the vertical axis represents intensity (arbitrary unit). With the toluene solution, absorption peaks were at around 281 nm, 319 nm, and 358 nm, and emission wavelength peaks were at 362 nm, 380 nm, and 399 nm (at an excitation wavelength of 339 nm). With the thin film, absorption peaks were at around 253 nm, 321 nm, and 364 nm, and an emission wavelength peak was at 395 nm (at an excitation wavelength of 365 nm).

Example 4

In this example, a light-emitting element according to one embodiment of the present invention (a light-emitting element 4) and a light-emitting element for comparison (a comparative light-emitting element 5), which are different from the light-emitting elements described in Example 2, will be described with reference to FIG. 12. Chemical formulas of materials used in this example are shown below.

(109)

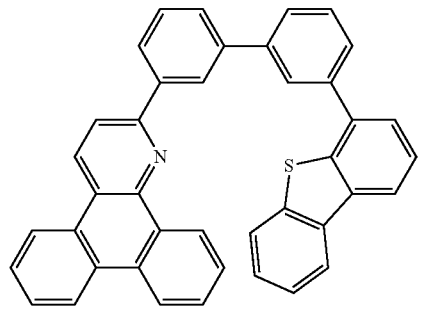

2mDBTBPDBQu-II

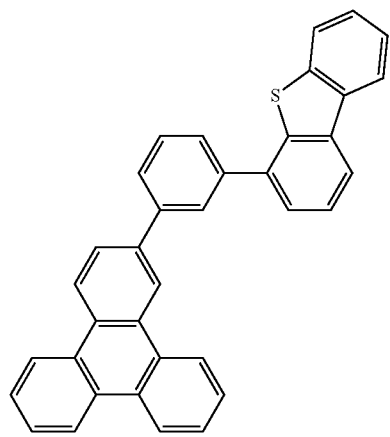

mDBTPTp-II

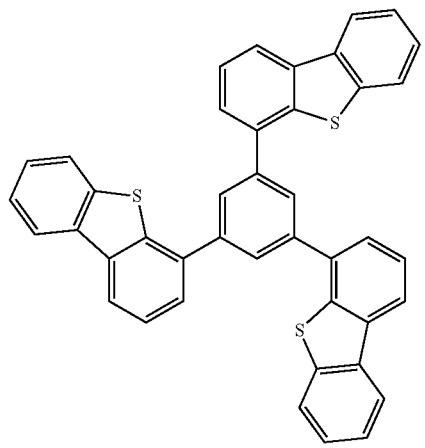

DBT3P-II

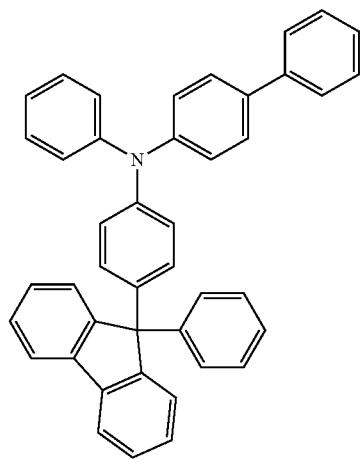

BPAFLP

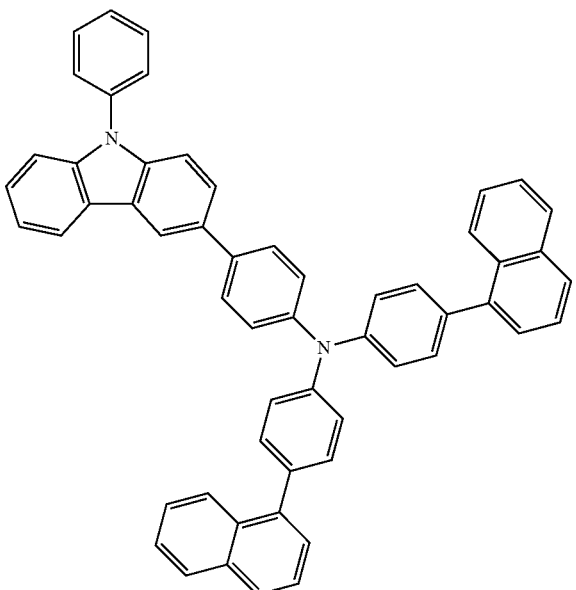

PCBNBB

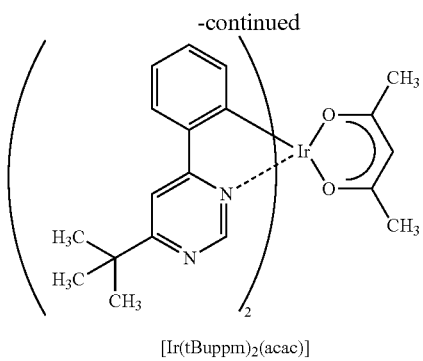

[Ir(tBuppm)₂(acac)]

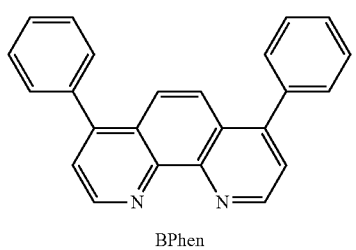

BPhen

The following shows methods of fabricating the light-emitting element 4 and the comparative light-emitting element 5 in this example.

(Light-Emitting Element 4)

First, over the substrate 1100, an indium oxide-tin oxide compound containing silicon or silicon oxide (ITO—SiO₂, hereinafter abbreviated to ITSO) was deposited by a sputtering method, so that the first electrode 1101 was formed. The composition ratio of a target used was $In_2O_3:SnO_2:SiO_2=85:10:5$ [wt %]. The thickness of the first electrode 1101 was 110 nm and the electrode area was 2 mm×2 mm. Here, the first electrode 1101 is an electrode that functions as an anode of the light-emitting element.

Next, as pretreatment for forming the light-emitting element over the substrate 1100, the surface of the substrate was washed, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a substrate holder in a vacuum evaporation apparatus so that a surface of the substrate 1100 on which the first electrode 1101 was formed faced downward. The pressure in the vacuum evaporation apparatus was reduced to about $10^{-4}$ Pa. Then, by an evaporation method using resistance heating, 1,3,5-tri(dibenzothiophen-4-yl)-benzene (abbreviation: DBT3P-II) and molybdenum oxide were co-evaporated over the first electrode 1101, so that the hole-injection layer 1111 was formed. The thickness of the hole-injection layer 1111 was set to 40 nm, and the weight ratio of DBT3P-II (abbreviation) to molybdenum oxide was adjusted to 4:2 (=DBT3P-II:molybdenum oxide).

Next, over the hole-injection layer 1111, a film of BPAFLP (abbreviation) was formed to a thickness of 20 nm, so that the hole-transport layer 1112 was formed.

Further, 2-{3-[3-(dibenzothiophen-4-yl)phenyl]phenyl}dibenzo[f,h]quinoline (abbreviation: 2mDBTBPDBQu-II) synthesized in Example 3, 4,4'-di(1-naphthyl)-4"-(9-phenyl-9H-carbazol-3-yl)triphenylamine (abbreviation: PCBNBB), and (acetylacetonato)bis(6-tert-butyl-4-phenylpyrimidinato)iridium(III) (abbreviation:[Ir(tBuppm)₂(acac)]) were co-evaporated, so that the light-emitting layer 1113 was formed over the hole-transport layer 1112. Here, the weight ratio of 2mDBTBPDBQu-II (abbreviation) to PCBNBB (abbreviation) and [Ir(tBuppm)₂(acac)] (abbreviation) was adjusted to 0.8:0.2:0.05 (=2mDBTBPDBQu-II:PCBNBB:[Ir(tBuppm)₂(acac)]). The thickness of the light-emitting layer 1113 was set to 40 nm.

Further, a 2mDBTBPDBQu-II (abbreviation) film was deposited to a thickness of 10 nm over the light-emitting layer 1113, so that the first electron-transport layer 1114a was formed.

Then, a bathophenanthroline (abbreviation: BPhen) film was deposited to a thickness of 20 nm over the first electron-transport layer 1114a, so that a second electron-transport layer 1114b was formed.

Further, a lithium fluoride (LiF) film was formed to a thickness of 1 nm over the second electron-transport layer 1114b by evaporation, so that the electron-injection layer 1115 was formed.

Lastly, an aluminum film was formed to a thickness of 200 nm by evaporation, so that a second electrode 1103 functioning as a cathode was formed. Thus, the light-emitting element 4 in this example was fabricated.

Note that, in the above evaporation process, evaporation was all performed by a resistance heating method.

(Comparative Light-Emitting Element 5)

The light-emitting layer 1113 of the comparative light-emitting element 5, which corresponds to the light-emitting layer 1113 of the light-emitting element 4, was formed by co-evaporation of 4-[3-(triphenylene-2-yl)phenyl]dibenzothiophene (abbreviation: mDBTPTp-II), 4,4'-di(1-naphthyl)-4"-(9-phenyl-9H-carbazol-3-yl)triphenylamine (abbreviation: PCBNBB), and (acetylacetonato)bis(6-tert-butyl-4-phenylpyrimidinato)iridium(III) (abbreviation: [Ir(tBuppm)₂(acac)]). The weight ratio of mDBTPTp-II (abbreviation) to PCBNBB (abbreviation) and [Ir(tBuppm)₂(acac)] (abbreviation) was adjusted to 0.8:0.2:0.05 (=mDBTPTp-II:PCBNBB:[Ir(tBuppm)₂(acac)]). The thickness of the light-emitting layer 1113 was set to 40 nm.

Further, the first electron-transport layer 1114a of the comparative light-emitting element 5, which corresponds to the first electron-transport layer 1114a of the light-emitting element 4, was formed by depositing mDBTPTp-II (abbreviation) to a thickness of 10 nm. The components of the comparative light-emitting element 5 other than the light-emitting layer 1113 and the first electron-transport layer 1114a were formed in the same manner as those of light-emitting element 4.

Table 3 shows element structures of the light-emitting element 4 and the comparative light-emitting element 5 obtained as described above.

TABLE 3

| | First electrode | Hole-injection layer | Hole-transport layer | Light-emitting layer | First electron-transport layer | Second electron-transport layer | Electron-injection layer | Second Electrode | Note |
|---|---|---|---|---|---|---|---|---|---|
| Light-emitting element 4 | ITSO 110 nm | DBT3P-II: MoOx (=4:2) 40 nm | BPAFLP 20 nm | 2mDBTBPDBQu-II: PCBNBB: Ir(tBuppm)$_2$(acac) (=0.8:0.2:0.05) 40 nm | 2mDBTBPDBQu-II 10 nm | BPhen 20 nm | LiF 1 nm | Al 200 nm | Yellow green element |
| Comparative light-emitting element 5 | ITSO 110 nm | DBT3P-II: MoOx (=4:2) 40 nm | BPAFLP 20 nm | mDBTPTp-II: PCBNBB: Ir(tBuppm)$_2$(acac) (=0.8:0.2:0.05) 40 nm | mDBTPTp-II 10 nm | BPhen 20 nm | LiF 1 nm | Al 200 nm | Yellow green element |

The light-emitting element 4 and the comparative light-emitting element 5 were sealed with a glass substrate in a glove box containing a nitrogen atmosphere so as not to be exposed to the air (a sealant was applied onto an outer edge of each element and heat treatment was performed at 80° C. for 1 hour at the time of sealing). Then, the operating characteristics of these light-emitting elements were measured. Note that the measurement was carried out at room temperature (in an atmosphere kept at 25° C.).

Figure 24:
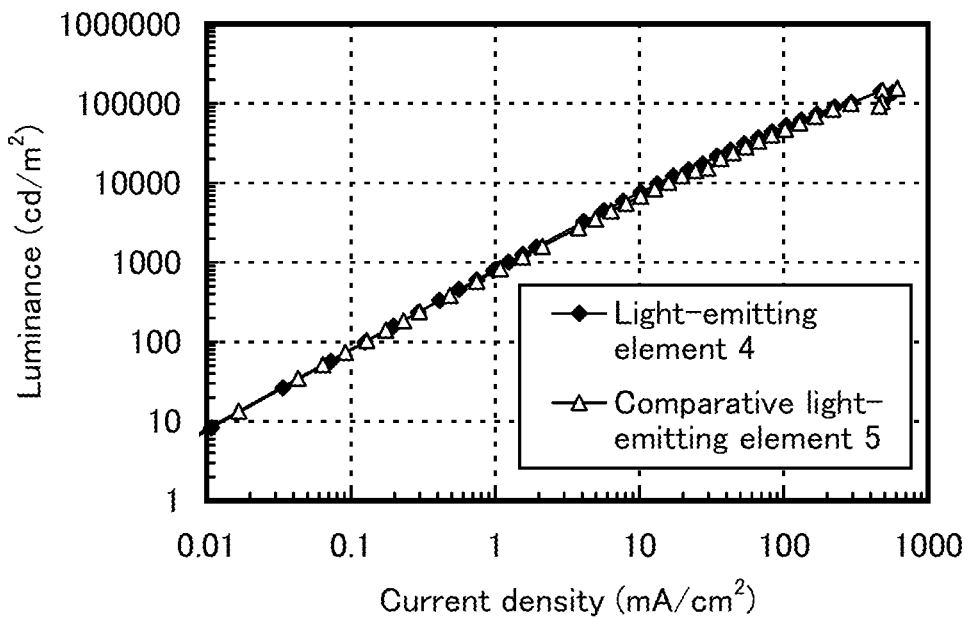
FIG. 24 shows current density-luminance characteristics of a light-emitting element 4 and a comparative light-emitting element 5.
Figure 25:
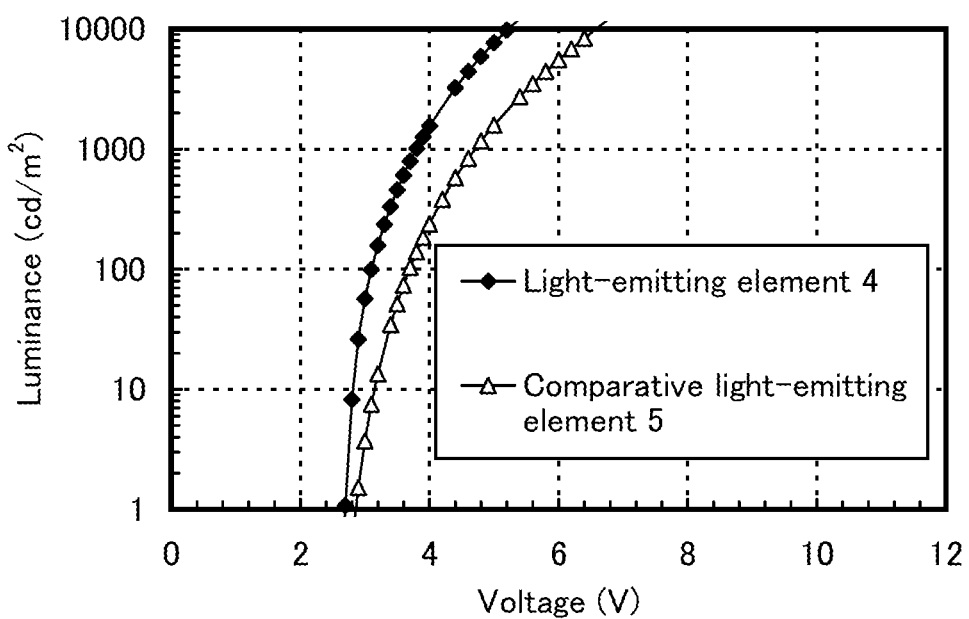
FIG. 25 shows voltage-luminance characteristics of the light-emitting element 4 and the comparative light-emitting element 5.
Figure 26:
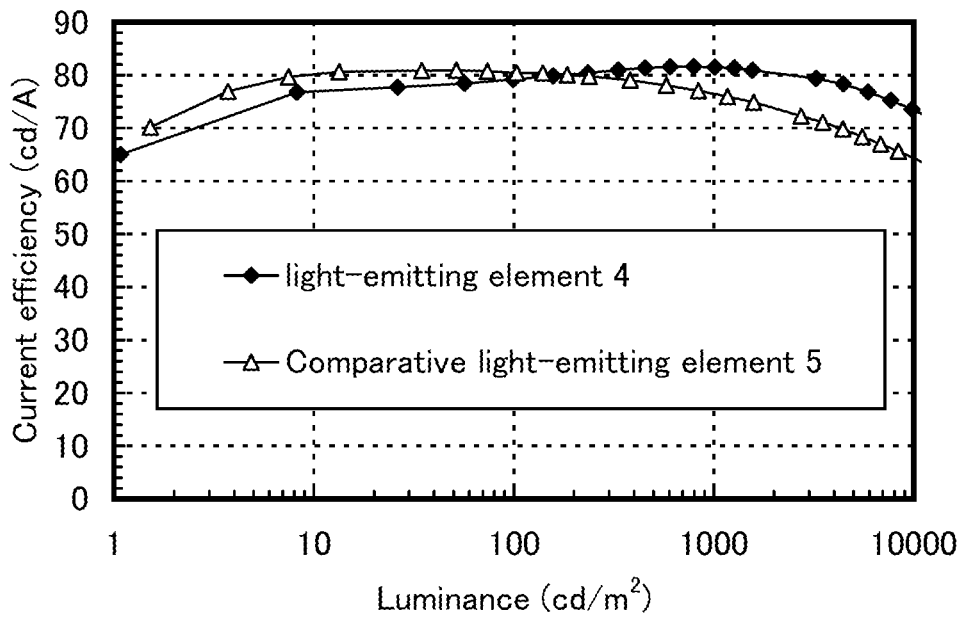
FIG. 26 shows luminance-current efficiency characteristics of the light-emitting element 4 and the comparative light-emitting element 5.
Figure 27:
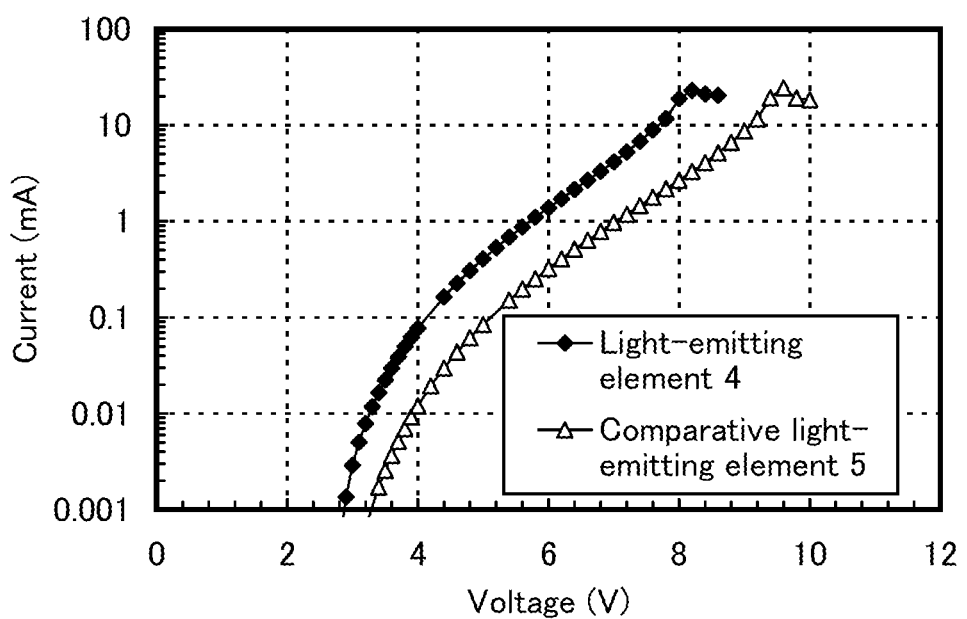
FIG. 27 shows voltage-current characteristics of the light-emitting element 4 and the comparative light-emitting element 5.

FIG. 24 shows current density-luminance characteristics of the light-emitting element 4 and the comparative light-emitting element 5. In FIG. 24, the horizontal axis represents current density (mA/cm$^2$), and the vertical axis represents luminance (cd/m$^2$). FIG. 25 shows voltage-luminance characteristics of the light-emitting element 4 and the comparative light-emitting element 5. In FIG. 25, the horizontal axis represents voltage (V) and the vertical axis represents luminance (cd/m$^2$). FIG. 26 shows luminance-current efficiency characteristics of the light-emitting element 4 and the comparative light-emitting element 5. In FIG. 26, the horizontal axis represents luminance (cd/m$^2$), and the vertical axis represents current efficiency (cd/A). FIG. 27 shows voltage-current characteristics of the light-emitting element 4 and the comparative light-emitting element 5. In FIG. 27, the horizontal axis represents voltage (V) and the vertical axis represents current (mA).

Further, Table 4 shows the voltage (V), current density (mA/cm$^2$), CIE chromaticity coordinates (x, y), current efficiency (cd/A), and external quantum efficiency (%) of each light-emitting element at a luminance of around 1000 cd/m$^2$.

TABLE 4

| | Voltage (V) | Current density (mA/cm$^2$) | Chromaticity (x, y) | | Luminance (cd/m$^2$) | Current efficiency (cd/A) | External quantum efficiency (%) |
|---|---|---|---|---|---|---|---|
| Light-emitting element 4 | 3.8 | 1.2 | 0.42 | 0.57 | 1009 | 82 | 23 |
| Comparative light-emitting element 5 | 4.6 | 1.1 | 0.41 | 0.58 | 836 | 77 | 22 |

As shown in Table 4, the CIE chromaticity coordinates (x, y) of the light-emitting element 1 were (0.42, 0.57) at a luminance of 1009 cd/m$^2$. The CIE chromaticity coordinates (x, y) of the comparative light-emitting element 5 were (0.41, 0.58) at a luminance of 836 cd/m$^2$.

From Table 4, it is found that current efficiencies of the light-emitting element 4 at a luminance of 1009 cd/m$^2$ and of the comparative light-emitting element 5 at a luminance of 836 cd/m$^2$ were 82 cd/A and 77 cd/A, respectively. Further, external quantum efficiencies of the light-emitting element 4 at a luminance of 1009 cd/m$^2$ and of the comparative light-emitting element 5 at a luminance of 836 cd/m$^2$ were 23% and 22%, respectively.

FIGS. 25 to 27 show that voltage-luminance characteristics, luminance-current efficiency characteristics, and voltage-current characteristics differ between the light-emitting element 4 according to one embodiment of the present invention and the comparative light-emitting element 5. It is found that the light-emitting element 4 is driven at a lower voltage and has higher current efficiency than the comparative light-emitting element 5. A structural difference between the compounds used as host materials in light-emitting layers is that the light-emitting element 4 includes a dibenzo[f,h]quinoline skeleton while the comparative light-emitting element 5 includes a triphenylene skeleton. It is thus confirmed that a compound having a dibenzo[f,h]quinoline skeleton, such as the heterocyclic compound according to one embodiment of the present invention, is highly effective in voltage-luminance characteristics, luminance-current efficiency characteristics, and voltage-current characteristics.

From Table 4, it is also found that the light-emitting element 4 has higher current efficiency and external quantum efficiency than the comparative light-emitting element 5. It is thus confirmed that a compound having a dibenzo[f,h]quinoline skeleton, such as the heterocyclic compound according to one embodiment of the present invention, is effective in achieving high current efficiency and high external quantum efficiency.

Next, reliability tests of the light-emitting element 4 and the comparative light-emitting element 5 were carried out. Results of the reliability tests are shown in FIG. 28.

In the reliability tests, the light-emitting element 4 and the comparative light-emitting element 5 were driven under the conditions where the initial luminance was set to 5000 cd/m$^2$ and the current density was constant. The results are shown in FIG. 28. The horizontal axis represents driving time (h) of the elements, and the vertical axis represents normalized luminance (%) on the assumption that an initial luminance is 100%. As shown in FIG. 28, it took about 678 hours of driving time for the normalized luminance of the light-emitting element 4 to decline 70% or lower, whereas it took about 291 hours of driving time for the normalized luminance of the comparative light-emitting element 5 to decline 70% or lower.

Figure 28:
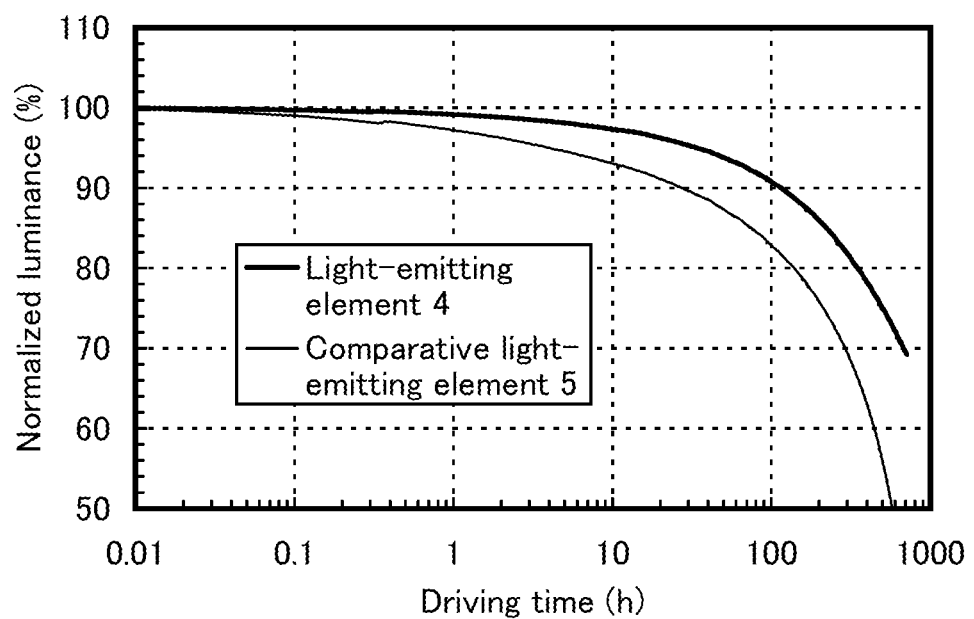
FIG. 28 shows results obtained by reliability tests of the light-emitting element 4 and the comparative light-emitting element 5.

From FIG. 28, it is found that the light-emitting element 4 according to one embodiment of the present invention has a longer lifetime than the comparative light-emitting element 5.

The above results show that the light-emitting element 4 in which 2mDBTBPDBQu-II (abbreviation) which is the heterocyclic compound according to one embodiment of the present invention is used for the light-emitting layer is driven at a low voltage and has high efficiency, low power consumption, and a long lifetime.

This application is based on Japanese Patent Application serial no. 2011-151717 filed with Japan Patent Office on Jul. 8, 2011, the entire contents of which are hereby incorporated by reference.

What is claimed is:

1. A compound comprising the following structure:

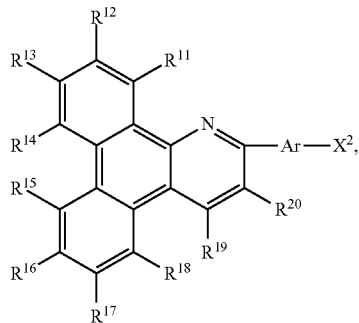

wherein:
$X^2$ represents halogen or a triflate group,
Ar represents an arylene group having 6 to 13 carbon atoms,
$R^{11}$ to $R^{20}$ separately represent any of hydrogen, an alkyl group having 1 to 4 carbon atoms, and a substituted or unsubstituted aryl group having 6 to 13 carbon atoms.

2. The compound according to claim 1, wherein the halogen is iodine or bromine.

3. A compound comprising the following structure:

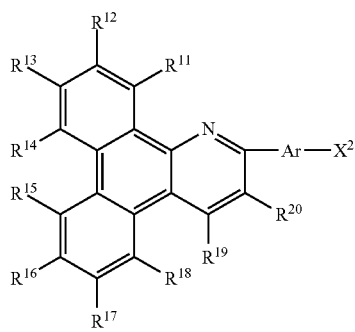

wherein:
$X^2$ represents halogen or a triflate group,
Ar represents an arylene group having 6 to 13 carbon atoms, and
$R^{11}$ to $R^{20}$ separately represent hydrogen.

4. The compound according to claim 3, wherein $X^2$ represents the triflate group.

5. The compound according to claim 3, wherein Ar represents a phenylene group.

6. The compound according to claim 3, wherein Ar represents a biphenyldiyl group.

7. A method for synthesizing a compound represented by a formula (G1), the method including:
performing a reaction according to the following scheme:

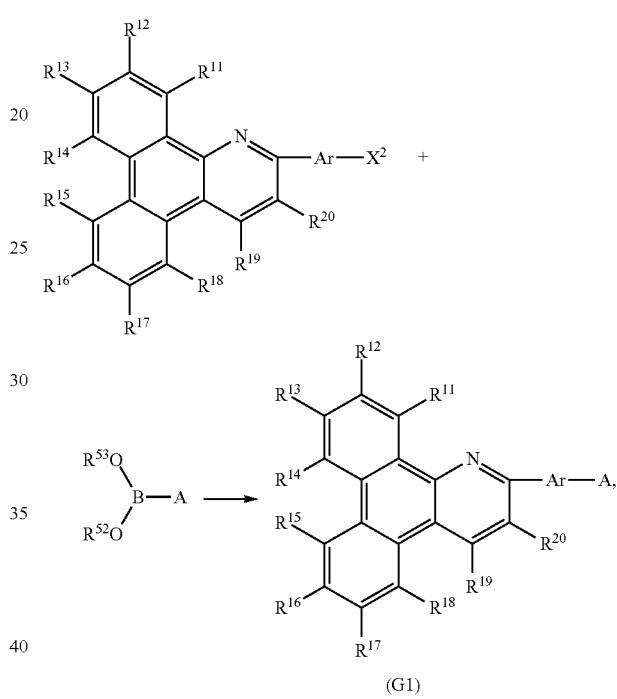

(G1)

wherein:
$X^2$ represents halogen or a triflate group,
Ar represents an arylene group having 6 to 13 carbon atoms,
$R^{11}$ to $R^{20}$ separately represent any of hydrogen, an alkyl group having 1 to 4 carbon atoms, and a substituted or unsubstituted aryl group having 6 to 13 carbon atoms,
$R^{52}$ and $R^{53}$ separately represent any of hydrogen and an alkyl group having 1 to 6 carbon atoms,
A represents any of a substituted or unsubstituted carbazolyl group, a substituted or unsubstituted dibenzothiophenyl group, and a substituted or unsubstituted dibenzofuranyl group, and
B represents boron.

8. The method according to claim 7, wherein the halogen is iodine or bromine.

9. The method according to claim 7, wherein $X^2$ represents the triflate group.

10. The method according to claim 7, wherein $R^{11}$ to $R^{20}$ separately represent hydrogen.

11. The method according to claim 7, wherein Ar represents a phenylene group.

12. The method according to claim 7, wherein Ar represents a biphenyldiyl group.

13. The method according to claim 7, wherein A represents the unsubstituted dibenzothiophenyl group.

14. The method according to claim 7, wherein a palladium catalyst is used in the reaction.

15. The method according to claim 14, wherein the palladium catalyst is selected from the group of palladium(II) acetate, tetrakis(triphenylphosphine)palladium(0), and bis(triphenylphosphine)palladium(II) dichloride.

16. The method according to claim 14, wherein a ligand of the palladium catalyst is selected from the group of tri(ortho-tolyl)phosphine, triphenylphosphine, and tricyclohexylphosphine.

17. A method of fabricating a light-emitting device comprising:
  forming a light-emitting layer using the compound represented by the formula (G1) obtained by the method according to claim 7 over a first electrode, and
  forming a second electrode over the light-emitting layer.

* * * * *